US012658285B2

(12) United States Patent
Tsumura et al.

(10) Patent No.: US 12,658,285 B2
(45) Date of Patent: Jun. 16, 2026

(54) FEATURE QUANTITY CALCULATING METHOD, SCREENING METHOD, AND COMPOUND CREATING METHOD

(71) Applicant: FUJIFILM Corporation, Tokyo (JP)

(72) Inventors: Kyosuke Tsumura, Ashigarakami-gun (JP); Hiroshi Yamashita, Ashigarakami-gun (JP); Jun Nakabayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 452 days.

(21) Appl. No.: 18/192,001

(22) Filed: Mar. 29, 2023

(65) Prior Publication Data

US 2023/0238084 A1    Jul. 27, 2023

Related U.S. Application Data

(63) Continuation of application No. PCT/JP2021/035520, filed on Sep. 28, 2021.

(30) Foreign Application Priority Data

Sep. 30, 2020    (JP) ................................. 2020-164800

(51) Int. Cl.
G16C 20/20        (2019.01)
G16C 20/50        (2019.01)
(52) U.S. Cl.
CPC ............. G16C 20/20 (2019.02); G16C 20/50 (2019.02)
(58) Field of Classification Search
CPC ........ G16C 20/20; G16C 20/30; G16C 20/50; G16C 20/70; G16C 20/80; G16B 15/30;
(Continued)

(56) References Cited

U.S. PATENT DOCUMENTS 9,373,059 B1    6/2016   Heifets et al.
2001/0018682 A1    8/2001   Itai et al.
(Continued)

FOREIGN PATENT DOCUMENTS

CA        2247820 C    *   2/2009    ............... B82B 1/00
CN    111279419 A        6/2020
(Continued)

OTHER PUBLICATIONS

Ikebata et al., "Bayesian molecular design with a chemical language model," J Comput Aided Mol Des, vol. 31, 2017 (Published online Mar. 9, 2017), pp. 379-391.
(Continued)

*Primary Examiner* — Jeffrey P Aiello
(74) *Attorney, Agent, or Firm* — Birch, Stewart, Kolasch & Birch, LLP

(57)        ABSTRACT

According to one embodiment of the present invention, provided are a feature quantity calculating method which enables calculation of a feature quantity accurately showing chemical properties of a target structure, a screening method which enables efficient screening of a pharmaceutical candidate compound using a feature quantity, and a compound creating method which enable efficient creation of a three-dimensional structure of a pharmaceutical candidate compound using a feature quantity. In one aspect of the present invention, the feature quantity calculating method is a method including a target structure designating step of designating a target structure formed of a plurality of unit structures having chemical properties, a three-dimensional structure acquiring step of acquiring a three-dimensional structure from the plurality of unit structures for the target structure, and a probe feature quantity calculating step of calculating a feature quantity showing a cross-sectional area of one or more kinds of probes for the target structure, in
(Continued)

START

INPUT STRUCTURAL FORMULA OF COMPOUND — S100

THREE-DIMENSIONALIZE INPUT STRUCTURAL FORMULA AND SET CENTROID AT $r = 0$ ($r = (x, y, z)$) — S102

CALCULATE INTERACTION ENERGY $V_{a\mu}(r)$ FELT BY EACH ATOM "$\mu$" OF AMINO ACID "a" — S104

CALCULATE INTERACTION ENERGY $V_a(r)$ FELT BY CENTROID OF AMINO ACID FROM $V_{a\mu}(r)$ — S106

CALCULATE $V_a(r)$ BY AVERAGING ANGLES WITH $r = 0$ AT CENTER WITH RESPECT TO $V_a(r)$ ($r = |r|$) — S108

CALCULATE CLOSEST CONTACT DISTANCE $r_{min,a}$ AND SCATTERING ANGLE $\theta_a$ AS FUNCTIONS OF INCIDENT ENERGY E AND IMPACT PARAMETER b FROM $V_a(r)$ — S110

CALCULATE DIFFERENTIAL SCATTERING CROSS-SECTIONAL AREA $d\sigma/d\Omega$ AS FUNCTIONS OF E AND b FROM $r_{min,a}$ AND SCATTERING ANGLE $\theta_a$ — S112

END which the probe is a structure in which a plurality of points having a real electric charge and generating a van der Waals force are disposed to be separated from each other.

26 Claims, 28 Drawing Sheets

(58) Field of Classification Search
CPC ........ G16B 15/20; G16B 15/10; G16B 35/20; G16B 35/10; G16B 40/20; G16B 40/30; G16B 25/20; G16B 25/30; G16B 25/10; G16B 20/00; G16B 20/30; G16B 20/20; G06N 3/045; G06N 3/0464; G06N 3/0475; G06N 3/08; G06N 3/09; G06N 3/088; G06N 3/096; G06N 3/042; C07K 2299/00; G01N 33/6803; G01N 33/68; G01N 2500/00; B01J 2219/00725; B01J 2219/00722; B01J 2219/00659
USPC ........ 382/128; 702/22, 19, 20, 27, 179, 182; 703/1, 2, 11
See application file for complete search history.

(56) References Cited

U.S. PATENT DOCUMENTS

| | | | |
|---|---|---|---|
| 2002/0038184 A1 | 3/2002 | Waldman et al. | |
| 2002/0062155 A1 | 5/2002 | Itai et al. | |
| 2010/0312538 A1 | 12/2010 | Umeyama et al. | |
| 2015/0310162 A1 | 10/2015 | Okuno et al. | |
| 2020/0243166 A1* | 7/2020 | Tsumura ................ | G16B 15/30 |
| 2020/0320355 A1 | 10/2020 | Heifets et al. | |

FOREIGN PATENT DOCUMENTS

| | | | | | |
|---|---|---|---|---|---|
| JP | 2011-4621 | A | 1/2003 | | |
| JP | 2005-122750 | A | 5/2005 | | |
| JP | 4564097 | B2 | 10/2010 | | |
| JP | 2012-13502 | A | 1/2012 | | |
| JP | 5946045 | B2 | 7/2016 | | |
| JP | 2017-520868 | A | 7/2017 | | |
| KR | 102828920 | B1 * | 7/2025 | ............ | G16C 20/70 |
| WO | WO-9613785 | A1 * | 5/1996 | ............ | G16B 15/30 |
| WO | WO 97/24301 | A1 | 7/1997 | | |
| WO | WO 2005/103994 | A1 | 11/2005 | | |
| WO | WO 2019/078006 | A1 | 4/2019 | | |
| WO | WO-2020203551 | A1 * | 10/2020 | ............ | G16C 20/64 |
| WO | WO-2022071268 | A1 * | 4/2022 | ............ | G06N 3/045 |

OTHER PUBLICATIONS

International Preliminary Report on Patentability and English translation of the Written Opinion of the International Searching Authority (Forms PCT/IB/326, PCT/IB/373 and PCT/ISA/237) for International Application No. PCT/JP2021/035520, dated Apr. 13, 2023.
International Search Report (Form PCT/ISA/210) for International Application No. PCT/JP2021/035520 dated Nov. 2, 2021, with English translation.
Extended European Search Report for corresponding European Application No. 21875569.2, dated Feb. 20, 2024.
Chinese Office Action and Search Report for corresponding Chinese Application No. 202180063534.7, dated Dec. 28, 2024, with an English translation.

* cited by examiner

FIG. 6

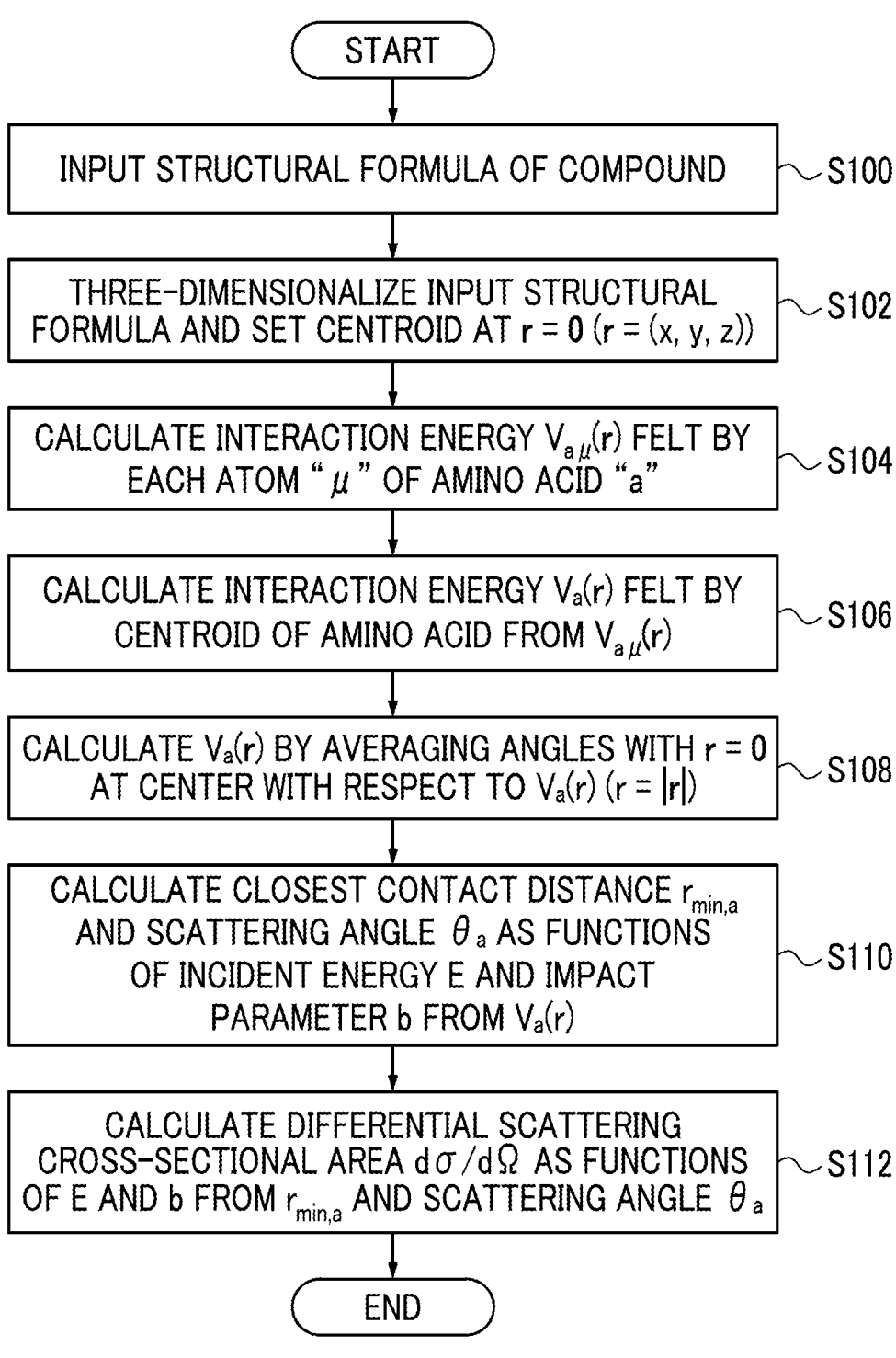

START

INPUT STRUCTURAL FORMULA OF COMPOUND — S100

THREE-DIMENSIONALIZE INPUT STRUCTURAL FORMULA AND SET CENTROID AT r = 0 (r = (x, y, z)) — S102

CALCULATE INTERACTION ENERGY $V_{a\mu}(r)$ FELT BY EACH ATOM "$\mu$" OF AMINO ACID "a" — S104

CALCULATE INTERACTION ENERGY $V_a(r)$ FELT BY CENTROID OF AMINO ACID FROM $V_{a\mu}(r)$ — S106

CALCULATE $V_a(r)$ BY AVERAGING ANGLES WITH r = 0 AT CENTER WITH RESPECT TO $V_a(r)$ (r = |r|) — S108

CALCULATE CLOSEST CONTACT DISTANCE $r_{min,a}$ AND SCATTERING ANGLE $\theta_a$ AS FUNCTIONS OF INCIDENT ENERGY E AND IMPACT PARAMETER b FROM $V_a(r)$ — S110

CALCULATE DIFFERENTIAL SCATTERING CROSS-SECTIONAL AREA $d\sigma/d\Omega$ AS FUNCTIONS OF E AND b FROM $r_{min,a}$ AND SCATTERING ANGLE $\theta_a$ — S112

END

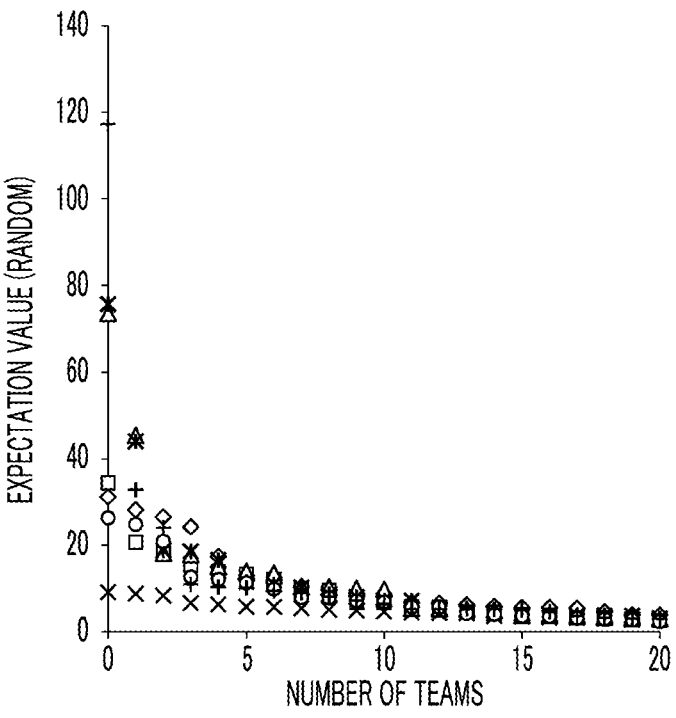

◇ (1) INVARIANT AAS DESCRIPTOR

▫ (2) INVARIANT PLURAL IONS
(Na$^+$, Cl$^-$)

△ (3) INVARIANT AAS DESCRIPTOR
AND IONS (Na$^+$, Cl$^-$)

✕ (4) INVARIANT DIPOLE

✳ (5) INVARIANT AAS DESCRIPTOR
AND DIPOLE

○ (6) INVARIANT PLURAL IONS
(Na$^+$, Cl$^-$) AND DIPOLE

+ (7) INVARIANT AAS DESCRIPTOR,
PLURAL IONS (Na$^+$, Cl$^-$),
AND DIPOLE

FIG. 12B

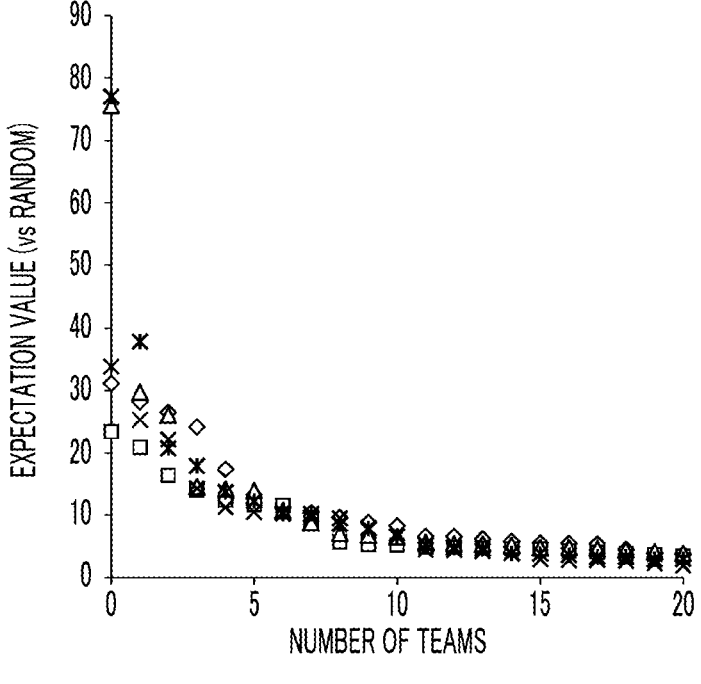

◇ (1) INVARIANT AAS DESCRIPTOR

▫ (8) INVARIANT MONOATOMIC ION
(Na$^+$)

△ (9) INVARIANT AAS DESCRIPTOR
AND MONOATOMIC ION (Na$^+$)

✕ (10) INVARIANT MONOATOMIC ION
(Na$^+$) AND DIPOLE

✳ (11) INVARIANT AAS DESCRIPTOR,
MONOATOMIC ION (Na$^+$),
AND DIPOLE

FIG. 15A

| LIGAND | | COMPOUND | | SIMILARITY | EXTRACTION RESULT |
|---|---|---|---|---|---|
| IDENTIFICATION INFORMATION | AAS DESCRIPTOR | IDENTIFICATION INFORMATION | AAS DESCRIPTOR | | |
| L00001 | L00001_$V_1(r)$ | C00001 | C00001_$V_1(r)$ | 85% | EXTRACTED |
| | | C00002 | C00002_$V_1(r)$ | 73% | NOT EXTRACTED |
| | | ... | ... | ... | ... |
| | | C00100 | C00100_$V_1(r)$ | 91% | EXTRACTED |
| | | ... | ... | ... | ... |
| | | C01000 | C01000_$V_1(r)$ | 80% | EXTRACTED |
| | | ... | ... | ... | ... |

FIG. 15B

| LIGAND | | COMPOUND | | SIMILARITY | | EXTRACTION RESULT |
|---|---|---|---|---|---|---|
| IDENTIFICATION INFORMATION | INVARIANT AAS DESCRIPTOR | IDENTIFICATION INFORMATION | INVARIANT AAS DESCRIPTOR | NUMERICAL VALUE | RANK | |
| L00001 | L00001_$V_1(r)$ L00002_$V_2(r)$ | C00100 | C00100_$V_1(r)$ C00100_$V_2(r)$ | 91% | 1 | EXTRACTED |
| | | C00001 | C00001_$V_1(r)$ C00001_$V_2(r)$ | 85% | 2 | EXTRACTED |
| | | ... | ... | ... | ... | ... |
| | | C01000 | C01000_$V_1(r)$ C01000_$V_2(r)$ | 80% | 100 | EXTRACTED |
| | | ... | ... | ... | ... | ... |
| | | C00002 | C00002_$V_1(r)$ C00002_$V_2(r)$ | 73% | 265 | NOT EXTRACTED |
| | | ... | ... | ... | ... | ... |

EXTRACTED

FIG. 17A

| POCKET STRUCTURE | | COMPOUND | | SIMILARITY | EXTRACTION RESULT |
|---|---|---|---|---|---|
| IDENTIFICATION INFORMATION | AAS DESCRIPTOR | IDENTIFICATION INFORMATION | AAS DESCRIPTOR | | |
| P00001 | P00001_$V_i(r)$ | C00001 | C00001_$V_i(r)$ | 85% | EXTRACTED |
| | | C00002 | C00002_$V_i(r)$ | 73% | NOT EXTRACTED |
| | | ... | ... | ... | ... |
| | | C00100 | C00100_$V_i(r)$ | 91% | EXTRACTED |
| | | ... | ... | ... | ... |
| | | C01000 | C01000_$V_i(r)$ | 80% | EXTRACTED |
| | | ... | ... | ... | ... |

FIG. 17B

| POCKET STRUCTURE | | COMPOUND | | SIMILARITY | | EXTRACTION RESULT |
|---|---|---|---|---|---|---|
| IDENTIFICATION INFORMATION | INVARIANT AAS DESCRIPTOR | IDENTIFICATION INFORMATION | INVARIANT AAS DESCRIPTOR | NUMERICAL VALUE | RANK | |
| P00001 | P00001_$V_1(r)$ P00002_$V_2(r)$ | C00100 | C00100_$V_1(r)$ C00100_$V_2(r)$ | 91% | 1 | EXTRACTED |
| | | C00001 | C00001_$V_1(r)$ C00001_$V_2(r)$ | 85% | 2 | EXTRACTED |
| | | ... | ... | ... | ... | ... |
| | | C01000 | C01000_$V_1(r)$ C01000_$V_2(r)$ | 80% | 100 | EXTRACTED |
| | | ... | ... | ... | ... | ... |
| | | C00001 | C00001_$V_1(r)$ C00001_$V_2(r)$ | 73% | 265 | NOT EXTRACTED |
| | | ... | ... | ... | ... | ... |

EXTRACTED

920

922

START

CALCULATE AAS DESCRIPTOR FOR POCKET STRUCTURE OF TARGET PROTEIN — S600

GENERATE GENERATOR THROUGH MACHINE LEARNING — S602

GENERATE THREE-DIMENSIONAL STRUCTURE OF TARGET COMPOUND FROM AAS DESCRIPTOR OF POCKET STRUCTURE USING GENERATOR — S604

END

FEATURE QUANTITY CALCULATING METHOD, SCREENING METHOD, AND COMPOUND CREATING METHOD

CROSS-REFERENCE TO RELATED APPLICATIONS

The present application is a Continuation of PCT International Application No. PCT/JP2021/035520 filed on Sep. 28, 2021 claiming priority under 35 U.S.C § 119(a) to Japanese Patent Application No. 2020-164800 filed on Sep. 30, 2020. Each of the above applications is hereby expressly incorporated by reference, in its entirety, into the present application.

BACKGROUND OF THE INVENTION

1. Field of the Invention

The present invention relates to a drug discovery support technology and particularly relates to calculation of a feature quantity, screening of a pharmaceutical candidate compound, and creation of a three-dimensional structure of a pharmaceutical candidate compound.

2. Description of the Related Art

In the related art, in the drug discovery research using a computer, pharmaceutical candidate compounds (hereinafter, referred to as "hits") have been searched for by preparing a library having tens of thousands to one hundred thousand of existing compounds, providing the structural formulae of the compounds, and examining the binding force with respect to one target protein. For example, U.S. Pat. No. 9,373,059B predicts a binding force by providing the structural formula of a compound. Further, JP5946045B also describes that a compound having a desired binding force is searched for gradually by repeating generation of a structural formula and prediction of a binding force (trial and error).

Further, JP4564097B describes that a search is performed using a descriptor referred to as "compound fingerprint". The term "descriptor" indicates information obtained from the structural formula of a compound, and the term "compound fingerprint" indicates information related to the presence or absence of various functional groups. Such a descriptor has a characteristic in that "in a case where the descriptors of compounds are similar, the skeletons of the compounds are similar".

In addition, the search for the structure of a compound having a desired physical property value has been performed mainly by solving "forward problem" (a molecular structure is provided as a cause of the problem, and the physical property value is acquired as a result) in the related art, but with the development of informatics in recent years, research on a solution of "inverse problem" (a physical property value is provided, and a molecular structure having the physical property value is acquired) is rapidly promoted. For example, U.S. Pat. No. 9,373,059B is known for searching for a structure by solving an inverse problem.

SUMMARY OF THE INVENTION

Recently, since highly required target proteins have been complicated and difficult, it is difficult to find hits simply by screening libraries. Meanwhile, the theoretical number of compounds is (the 60th power of 10) even in a case of being limited to the number of low molecules with a molecular weight of 500 or less. The number thereof is further increased in a case of widening the range to middle molecules with a molecular weight of approximately 1000, and thus there is still a possibility of finding hits, considering that the number of compounds synthesized since the dawn of history is approximately (the ninth power of 10). However, it is almost impossible to examine the binding force with respect to all the astronomical numbers of compounds by experiments or simulations. Even in a case of examination of the binding force with respect to some compounds, the efficiency is low only by repeating trial and error as described in U.S. Pat. No. 9,373,059B and JP5946045B. Further, in the case of a descriptor (feature quantity) in the related art such as the fingerprint described in JP4564097B, the feature quantities of compounds are not necessarily similar even in a case where the compounds exhibit the same drug efficacy. Further, since the feature quantities do not accurately show the chemical properties of the target structure, the efficiency of search using the feature quantities is low.

Further, in an inverse quantitative structure-property relationship (iqspr) described in "Bayesian molecular design with a chemical language model", Hisaki Ikebata et al., [Search on Jul. 17, 2020], Internet (https://www.ncbi. nlm.nih.gov/pubmed/28281211), there is a problem in that the search efficiency is quickly decreased due to the structural update algorithm (particle filter based on Bayesian estimation). Specifically, in the structural update based on the Bayesian estimation, the physical property value approaches the target value, but the diversity of the structure for search is decreased, and the search enters a local minimum state and cannot easily escape from the local minimum state (cannot reach the final structure) even after repeated trials.

As described above, in the related art, feature quantities do not accurately show the chemical properties of the target structures, and thus the efficiency of screening and creation of three-dimensional structures using the feature quantities is low.

The present invention has been conducted in consideration of the above-described circumstances, and an object thereof is to provide a feature quantity calculating method which enables calculation of a feature quantity accurately showing chemical properties of a target structure. Further, another object of the present invention is to provide a screening method which enables efficient screening of a pharmaceutical candidate compound using a feature quantity. Further, still another object of the present invention is to provide a compound creating method which enables efficient creation of a three-dimensional structure of a pharmaceutical candidate compound using a feature quantity.

In order to achieve the above-described object, according to a first aspect of the present invention, there is provided a feature quantity calculating method comprising: a target structure designating step of designating a target structure formed of a plurality of unit structures having chemical properties; a three-dimensional structure acquiring step of acquiring a three-dimensional structure from the plurality of unit structures for the target structure; and a probe feature quantity calculating step of calculating a feature quantity showing a cross-sectional area of one or more kinds of probes for the target structure, in which the probe is a structure in which a plurality of points having a real electric charge and generating a van der Waals force are disposed to be separated from each other.

Since the chemical properties of target structures are exhibited as the result of an interaction between the target structure and one or more kinds of probes in the periphery thereof, the fact that target structures have similar feature quantities showing the cross-sectional areas indicates that the chemical properties of the target structures are similar. That is, target structures having similar feature quantities calculated according to the first aspect exhibit similar chemical properties. Therefore, according to the first aspect, the feature quantity accurately showing the chemical properties of a target structure can be calculated. In addition, in the first aspect and each of the following aspects, the concept of "cross-sectional area" includes a scattering cross-sectional area (differential scattering cross-sectional area), a reaction cross-sectional area, and an absorption cross-sectional area.

In the feature quantity calculating method according to a second aspect, in the first aspect, a cross-sectional area, a closest distance, and a scattering angle are calculated as the feature quantity in the probe feature quantity calculating step. The second aspect specifically defines "feature quantity showing the cross-sectional area" in the first aspect.

In the feature quantity calculating method according to a third aspect, in the first or second aspect, the feature quantity depending on a kind, a number, a combination, an impact parameter, and incident energy of the probe is calculated as the feature quantity in the probe feature quantity calculating step.

In the feature quantity calculating method according to a fourth aspect, in any of the first to third aspects, the three-dimensional structure is acquired by generating a three-dimensional structure of a designated target structure in the three-dimensional structure acquiring step.

In the feature quantity calculating method according to a fifth aspect, in any one of the first to fourth aspects, a compound is designated as the target structure in the target structure designating step, a three-dimensional structure of the compound formed of the plurality of atoms as a plurality of unit structures is acquired in the three-dimensional structure acquiring step, and a first feature quantity of the compound acquired in the three-dimensional structure acquiring step is calculated using an amino acid as the probe in the probe feature quantity calculating step. In the fifth aspect, "probe", "target structure", and "plurality of unit structures" in the first aspect are respectively an amino acid, a compound, and a plurality of atoms. Further, the number of kinds of amino acids used for quantifying the degree of accumulation is not limited to one, and a peptide in which two or more kinds of amino acids are bound may be used.

The feature quantity calculating method according to a sixth aspect, in the fifth aspect, further comprises an invariant conversion step of converting the first feature quantity into an invariant with respect to rotation of the compound to calculate a first invariant feature quantity. In the sixth aspect, since the first feature quantity is converted into an invariant with respect to rotation of the compound, the feature quantity is easily handled and the data capacity can be reduced. The first feature quantity can be converted into an invariant by averaging the angles of the potentials.

In the feature quantity calculating method according to a seventh aspect, in the sixth aspect, the first feature quantity of two different kinds of amino acids is calculated in the probe feature quantity calculating step, and the first invariant feature quantity is calculated using the first feature quantity of the two different kinds of amino acids in the invariant conversion step. According to the seventh aspect, since the conversion into an invariant can be performed while information related to the interaction between the amino acids is maintained using the first feature quantity of two different kinds of amino acids in the calculation of the first invariant feature quantity, the comparison of compounds (determination of the drug efficacy) can be accurately performed based on the feature quantity (first invariant feature quantity).

In the feature quantity calculating method according to an eighth aspect, in any of the first to fourth aspects, a pocket structure bound to a pocket that is an active site of a target protein is designated as the target structure in the target structure designating step, a three-dimensional structure of the pocket structure is acquired with a plurality of virtual spheres in the three-dimensional structure acquiring step, and a second feature quantity of the pocket structure acquired in the three-dimensional structure acquiring step is calculated using an amino acid as a probe in the probe feature quantity calculating step. In the eighth aspect, "probe", "target structure", and "unit structure" in the first aspect are respectively an amino acid, a pocket structure, and a plurality of virtual spheres. The term "active site" of the target protein indicates a site where the activity of the target protein is promoted or suppressed by binding a pocket structure, and the term "virtual sphere" can be considered to have chemical properties such as the van der Waals radius and the electric charge.

The degree of accumulation of amino acids with respect to the provided compound is calculated in the fifth aspect described above, while the feature quantity (second feature quantity) showing the cross-sectional area of amino acids with respect to the pocket structure bound to a pocket of the provided target protein is calculated in the eighth aspect. Since the pocket structures having similar feature quantities according to the eighth aspect exhibit similar chemical properties, the feature quantity accurately showing the chemical properties of the pocket structure can be calculated according to the eighth aspect. Further, the pocket structure corresponds to a compound that is bound to a pocket of the target protein. Further, in the eighth aspect, as the result of actual measurement on the three-dimensional structure of the target protein, simulation based on position information and the like of the pocket can be used for calculation of the second feature quantity. Further, the measuring techniques (for example, an X-ray crystal structure, an NMR structure (NMR: Nuclear Magnetic Resonance), and a cryo-TEM structure (TEM: Transmission Electron Microscopy)) are not limited as long as the three-dimensional structure of the target protein is a three-dimensional structure with a resolution that enables identification of each residue of an amino acid.

The feature quantity calculating method according to the ninth aspect, in the eighth aspect, further comprises: an invariant conversion step of converting the second feature quantity into an invariant with respect to rotation of the pocket structure to calculate a second invariant feature quantity. According to the ninth aspect, similarly to the sixth aspect, the feature quantity can be easily handled and the data capacity can be reduced. The second feature quantity is converted into an invariant by averaging the angles of the potentials in the same manner as in the sixth aspect.

In the feature quantity calculating method according to a tenth aspect, in the ninth aspect, the second feature quantity of two different kinds of amino acids is calculated in the probe feature quantity calculating step, and the second invariant feature quantity is calculated using the second feature quantity of the two different kinds of amino acids in the invariant conversion step. According to the tenth aspect, since the conversion into an invariant can be performed while information related to the interaction between the amino acids is maintained using the second feature quantity of two different kinds of amino acids in the calculation of the second invariant feature quantity, the comparison of compounds (determination of the drug efficacy) can be accurately performed based on the feature quantity (second invariant feature quantity).

In the feature quantity calculating method according to the eleventh aspect, in any of the first to fourth aspects, a compound is designated as the target structure in the target structure designating step, a three-dimensional structure of the compound formed of a plurality of atoms is generated in the three-dimensional structure acquiring step, and a third feature quantity of the three-dimensional structure of the compound acquired in the three-dimensional structure acquiring step is calculated using one or more among one or more kinds of nucleic acid bases, one or more kinds of lipid molecules, one or more kinds of monosaccharide molecules, water, and one or more kinds of ions, as the probes in the probe feature quantity calculating step. In the eleventh aspect, "probe", "target structure", and "plurality of unit structures" in the first aspect are respectively one or more kinds of nucleic acid bases (the kind, the number, and the combination thereof may be optional), a compound, and a plurality of atoms. Further, the ion may be a monoatomic ion or an ion formed of a plurality of atoms.

The feature quantity calculating method according to a twelfth aspect, in the eleventh aspect, further comprises: an invariant conversion step of converting the third feature quantity into an invariant with respect to rotation of the compound to calculate a third invariant feature quantity. According to the twelfth aspect, similar to the sixth and ninth aspects, the feature quantity is easily handled and the data capacity can be reduced. The third feature quantity can be converted into an invariant by averaging the angles of the potentials in the same manner as in the sixth and ninth aspects.

In order to achieve the above-described object, according to a thirteenth aspect of the present invention, there is provided a screening method of extracting a first target compound which is bound to a target protein and/or a second target compound which is not bound to the target protein, from a plurality of compounds, the method comprising: a storing step of storing a three-dimensional structure of a compound formed of a plurality of atoms and the first feature quantity of the three-dimensional structure of the compound which is calculated using the feature quantity calculating method according to the fifth aspect in association with each other for each of the plurality of compounds; a screening feature quantity calculating step of calculating the first feature quantity of a ligand that is a compound whose binding to the target protein has been confirmed; a similarity calculating step of calculating a similarity between the first feature quantity of the plurality of compounds and the first feature quantity of the ligand; and a compound extracting step of extracting the first target compound and the second target compound from the plurality of compounds based on the similarity. As the description for the fifth aspect, in a case where the ligand and the target compound have similar first feature quantities, the drug efficacies of both the ligand and the target compound are similar. Therefore, according to the thirteenth aspect, a target compound (the first target compound and/or the second target compound) having drug efficacy similar to that of the ligand can be extracted based on the first feature quantity so that screening of a pharmaceutical candidate compound can be efficiently performed.

In order to achieve the above-described object, according to a fourteenth aspect of the present invention, there is provided a screening method of extracting a first target compound which is bound to a target protein and/or a second target compound which is not bound to the target protein, from a plurality of compounds, the method comprising: a storing step of storing a three-dimensional structure of a compound formed of a plurality of atoms and the first invariant feature quantity of the three-dimensional structure of the compound calculated using the feature quantity calculating method according to the sixth aspect in association with each other for each of the plurality of compounds; a screening feature quantity calculating step of calculating the first invariant feature quantity of a ligand that is a compound whose binding to the target protein has been confirmed; a similarity calculating step of calculating a similarity between the first invariant feature quantity of the plurality of compounds and the first invariant feature quantity of the ligand; and a compound extracting step of extracting the target compound and/or the second target compound from the plurality of compounds based on the similarity. The fourteenth aspect is common to the thirteenth aspect in terms that the feature quantity of the ligand is calculated. However, in the fourteenth aspect, a target compound (the first target compound and/or the second target compound) having drug efficacy similar to that of the ligand can be extracted based on the similarity of the first invariant feature quantity so that screening of a pharmaceutical candidate compound can be efficiently performed.

In order to achieve the above-described object, according to a fifteenth aspect of the present invention, there is provided a screening method of extracting a first target compound which is bound to a target protein and/or a second target compound which is not bound to the target protein, from a plurality of compounds, the method comprising: a storing step of storing a three-dimensional structure of a compound formed of a plurality of atoms and the first feature quantity calculated by the feature quantity calculating method according to the fifth aspect in association with each other for each of the plurality of compounds; a screening feature quantity calculating step of calculating the second feature quantity of the pocket structure of the target protein using the feature quantity calculating method according to the eighth aspect; a similarity calculating step of calculating a similarity between the first feature quantity of the plurality of compounds and the second feature quantity of the pocket structure; and a compound extracting step of extracting the first target compound and/or the second target compound from the plurality of compounds based on the similarity.

As the description for the eighth aspect, in a case where the pocket structure and the target compound have similar second feature quantities, the chemical properties of both the pocket structure and the target compound are similar. Therefore, according to the fifteenth aspect, a target compound (the first target compound and/or the second target compound) having chemical properties similar to those of the pocket structure is extracted so that screening of a pharmaceutical candidate compound can be efficiently performed. Since the pocket structure corresponds to the compound that is bound to the target protein, the feature quantity (the second feature quantity) of the pocket structure can be compared with the feature quantity (the first feature quantity) of the compound, and the similarity can be calculated.

In order to achieve the above-described object, according to a sixteenth aspect of the present invention, there is provided a screening method of extracting a first target compound which is bound to a target protein and/or a second target compound which is not bound to the target protein, from a plurality of compounds, the method comprising: a storing step of storing a three-dimensional structure of a compound formed of a plurality of atoms and the first invariant feature quantity calculated using the feature quantity calculating method according to the sixth aspect in association with each other for each of the plurality of compounds; a screening feature quantity calculating step of calculating the second invariant feature quantity of the pocket structure of the target protein using the feature quantity calculating method according to the ninth aspect; a similarity calculating step of calculating a similarity between the first invariant feature quantity of the plurality of compounds and the second invariant feature quantity of the pocket structure; and a compound extracting step of extracting the first target compound and/or the second target compound from the plurality of compounds based on the similarity. In the sixteenth aspect, a target compound (the first target compound and/or the second target compound) having chemical properties similar to those of the pocket structure is extracted using the first and second invariant feature quantities so that screening of a pharmaceutical candidate compound can be efficiently performed. As the description for the fifteenth aspect, the feature quantity (the second invariant feature quantity) of the pocket structure can be compared with the feature quantity (the first invariant feature quantity) of the compound, and the similarity can be calculated.

In order to achieve the above-described object, according to a seventeenth aspect of the present invention, there is provided a screening method of extracting a target compound which is bound to a target biopolymer other than a protein from a plurality of compounds, the method comprising: a storing step of storing a three-dimensional structure of a compound formed of a plurality of atoms and the third feature quantity of the three-dimensional structure of the compound calculated using the feature quantity calculating method according to the eleventh aspect in association with each other for each of the plurality of compounds; a feature quantity calculating step of calculating the third feature quantity of a binding compound that is a compound whose binding to the target biopolymer other than the protein has been confirmed; a similarity calculating step of calculating a similarity between the third feature quantity of the plurality of compounds and the third feature quantity of the binding compound; and a compound extracting step of extracting the target compound from the plurality of compounds based on the similarity. As the description for the eleventh aspect, according to the present invention, DNA or the like which is a target biopolymer other than a protein can be handled, and in a case where the target compound and the binding compound that is bound to the target biopolymer have similar third feature quantities, the drug efficacies of both the target compound and the binding compound are similar. Therefore, according to the seventeenth aspect, a target compound having drug efficacy similar to that of the binding compound is extracted based on the third feature quantity so that screening of a pharmaceutical candidate compound can be efficiently performed.

In addition, in the thirteenth to seventeenth aspects, a compound having a similarity greater than or equal to a threshold is extracted in the compound extracting step. The threshold can be set based on conditions, for example, the purpose and the accuracy of the screening and may be set based on a value designated by the user. Further, in the thirteenth to seventeenth aspects, compounds are extracted in a descending order of the similarity in the compound extracting step. With such an extraction, screening of a pharmaceutical candidate compound can be efficiently performed.

In order to achieve the above-described object, according to an eighteenth aspect of the present invention, there is provided a compound creating method of creating a three-dimensional structure of a target compound that is bound to a target protein from a plurality of compounds, the method comprising: a storing step of storing a three-dimensional structure of a compound formed of a plurality of atoms and the first feature quantity calculated using the feature quantity calculating method according to the fifth aspect in association with each other for each of the plurality of compounds; a creating feature quantity calculating step of calculating the first feature quantity of a ligand that is a compound whose binding to the target protein has been confirmed; a generator constructing step of constructing a generator through machine learning using the three-dimensional structure of the plurality of compounds as teacher data and the first feature quantity as an explanatory variable; and a compound three-dimensional structure generating step of generating a three-dimensional structure of the target compound from the first feature quantity of the ligand using the generator.

In the screening methods according to the thirteenth to seventeenth aspects described above, a compound that is compatible with a ligand or a target protein is found among a plurality of compounds whose structural formulae have already been determined (written down). Accordingly, after the feature quantity of the compound is calculated, a method of extracting the compound based on the similarity with the feature quantity of the separately calculated ligand or the pocket structure of the target protein, that is, a search method is employed. Therefore, in a case where the correspondence between the structural formula of the compound and the feature quantity thereof is recorded, a structural formula having a high similarity (greater than or equal to the threshold) can be found. Meanwhile, in the eighteenth aspect, a structural formula of a compound having a feature quantity similar to the feature quantity (the first feature quantity) of the ligand (accordingly, the drug efficacies are similar) is generated without performing search.

The generation of the structural formula in a case where the feature quantity has been provided can be performed using a generator constructed through machine learning. Specifically, in the eighteenth aspect, a generator is constructed through machine learning (the learning method is not particularly limited) using the three-dimensional structures of the compounds as teacher data and the first feature quantity as an explanatory variable, and a three-dimensional structure of the target compound is generated from the first feature quantity of the ligand using the generator. In the eighteenth aspect, since search is not performed, the three-dimensional structure of the compound can be generated even in a case of "no solution was found as the result of screening search", and thus the three-dimensional structure of the pharmaceutical candidate compound can be efficiently created.

Further, the three-dimensional structure to be generated in the eighteenth aspect is affected by the features of the compound provided as teacher data. Therefore, a compound having a three-dimensional structure with different features can be generated by selecting the features of the compound to be provided as teacher data. For example, a compound having a three-dimensional structure that is easily synthesized can be generated by providing a compound that is easily synthesized as teacher data.

In order to achieve the above-described object, according to a nineteenth aspect of the present invention, there is provided a compound creating method of creating a three-dimensional structure of a target compound that is bound to a target protein from a plurality of compounds, the method comprising: a storing step of storing a three-dimensional structure of a compound formed of a plurality of atoms and the first invariant feature quantity calculated using the feature quantity calculating method according to the sixth aspect in association with each other for each of the plurality of compounds; a creating feature quantity calculating step of calculating the first invariant feature quantity of a ligand that is a compound whose binding to the target protein has been confirmed; a generator constructing step of constructing a generator through machine learning using the three-dimensional structure of the plurality of compounds as teacher data and the first invariant feature quantity as an explanatory variable; and a compound three-dimensional structure generating step of generating a three-dimensional structure of the target compound from the first invariant feature quantity of the ligand using the generator. In the nineteenth aspect, similar to the eighteenth aspect, a structural formula of a compound having a feature quantity similar to the feature quantity (the first invariant feature quantity) of the ligand (accordingly, the drug efficacies are similar) is generated without performing search, and thus the three-dimensional structure of the pharmaceutical candidate compound can be efficiently created. Further, similar to the eighteenth aspect, a compound having a three-dimensional structure with different features can be generated by selecting the features of the compound to be provided as teacher data.

In order to achieve the object described above, according to a twentieth aspect of the present invention, there is provided a compound creating method of creating a three-dimensional structure of a target compound that is bound to a target protein from a plurality of compounds, the method comprising: a storing step of storing a three-dimensional structure of a compound formed of a plurality of atoms and the first feature quantity calculated using the feature quantity calculating method according to the fifth aspect in association with each other for each of the plurality of compounds; a creating feature quantity calculating step of calculating the second feature quantity of the pocket structure of the target protein using the feature quantity calculating method according to the eighth aspect; a generator constructing step of constructing a generator through machine learning using the three-dimensional structures of the plurality of compounds as teacher data and the first feature quantity as an explanatory variable; and a compound three-dimensional structure generating step of generating the three-dimensional structure of the target compound from the second feature quantity of the pocket structure using the generator. According to the twentieth aspect, similar to the eighteenth and nineteenth aspects, a structural formula of a compound having a feature quantity similar to the feature quantity (the second feature quantity) of the pocket structure (accordingly, the drug efficacies are similar) is generated without performing search, and thus the three-dimensional structure of the pharmaceutical candidate compound can be efficiently created. Similar to the eighteenth and nineteenth aspects, a compound having a three-dimensional structure with different features can be generated by selecting the features of the compound to be provided as teacher data.

In order to achieve the object described above, according to a twenty-first aspect of the present invention, there is provided a compound creating method of creating a three-dimensional structure of a target compound that is bound to a target protein from a plurality of compounds, the method comprising: a storing step of storing a three-dimensional structure of a compound formed of a plurality of atoms and the first invariant feature quantity calculated using the feature quantity calculating method according to the sixth aspect in association with each other for each of the plurality of compounds; a creating feature quantity calculating step of calculating the second invariant feature quantity of the pocket structure of the target protein using the feature quantity calculating method according to the ninth aspect; a generator constructing step of constructing a generator through machine learning using the three-dimensional structure of the plurality of compounds as teacher data and the first invariant feature quantity as an explanatory variable; and a compound three-dimensional structure generating step of generating a three-dimensional structure of the target compound from the second invariant feature quantity of the pocket structure using the generator. According to the twenty-first aspect, similar to the eighteenth to twentieth aspects, a structural formula of a compound having a feature quantity similar to the feature quantity (the second invariant feature quantity) of the pocket structure (accordingly, the drug efficacies are similar) is generated without performing search, and thus the three-dimensional structure of the pharmaceutical candidate compound can be efficiently created. Similar to the eighteenth to twentieth aspects, a compound having a three-dimensional structure with different features can be generated by selecting the features of the compound to be provided as teacher data.

In order to achieve the above-described object, according to a twenty-second aspect of the present invention, there is provided a compound creating method of creating a three-dimensional structure of a target compound that is bound to a target biopolymer other than a protein from a plurality of compounds, the method comprising: a storing step of storing a three-dimensional structure of a compound formed of a plurality of atoms and the third feature quantity calculated using the feature quantity calculating method according to the eleventh aspect in association with each other for each of the plurality of compounds; a creating feature quantity calculating step of calculating the third feature quantity of a binding compound that is a compound whose binding to the target biopolymer other than the protein has been confirmed; a generator constructing step of constructing a generator through machine learning using the three-dimensional structures of the plurality of compounds as teacher data and the third feature quantity as an explanatory variable; and a compound three-dimensional structure generating step of generating the three-dimensional structure of the target compound from the third feature quantity of the binding compound using the generator. According to the twenty-second aspect, similar to the eighteenth to twenty-first aspects, a structural formula of a compound having a feature quantity similar to the feature quantity (the third feature quantity) of the binding compound (accordingly, the drug efficacies are similar) is generated without performing search, and thus the three-dimensional structure of the pharmaceutical candidate compound can be efficiently created. Similar to the eighteenth to twenty-first aspects, a compound having a three-dimensional structure with different features can be generated by selecting the features of the compound to be provided as teacher data.

In order to achieve the above-described object, according to a twenty-third aspect of the present invention, there is provided a compound creating method of creating a three-dimensional structure of a target compound that is bound to a target protein, the method comprising: an input step of inputting a chemical structure of one or a plurality of compounds, the first feature quantity of the chemical structure calculated using the feature quantity calculating method according to the fifth aspect, and the first feature quantity of a ligand that is a compound whose binding to the target compound has been confirmed as a target value of the first feature quantity; a candidate structure acquiring step of changing the chemical structure to obtain a candidate structure; a creating feature quantity calculating step of calculating the first feature quantity of the candidate structure using the feature quantity calculating method according to the fifth aspect; a candidate structure adopting step of adopting or rejecting the candidate structure by performing a first adoption process of determining whether or not to adopt the candidate structure based on whether or not the first feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied.

In the compound creating method according to the twenty-third aspect, escape from the local minimum state is promoted based on the structural diversity, and thus the structure of the compound having a desired physical property value (target value of the first feature quantity) can be efficiently searched for. Further, since the search in the twenty-third aspect is not performed in the same manner as in the eighteenth aspect, the three-dimensional structure of the compound (compound having a feature quantity similar to the feature quantity (the first feature quantity) of the ligand, and accordingly, the drug efficacies are similar) can be generated even in a case of "no solution was found as the result of screening search", and thus the three-dimensional structure of the pharmaceutical candidate compound can be efficiently created.

In order to achieve the above-described object, according to a twenty-fourth aspect of the present invention, there is provided a compound creating method of creating a three-dimensional structure of a target compound that is bound to a target protein, the method comprising: an input step of inputting a chemical structure of one or a plurality of compounds, the first invariant feature quantity of the chemical structure calculated using the feature quantity calculating method according to the sixth aspect, and the first invariant feature quantity of a ligand that is a compound whose binding to the target compound has been confirmed as a target value of the first invariant feature quantity; a candidate structure acquiring step of changing the chemical structure to obtain a candidate structure; a creating feature quantity calculating step of calculating the first invariant feature quantity of the candidate structure using the feature quantity calculating method according to the sixth aspect; a candidate structure adopting step of adopting or rejecting the candidate structure by performing a first adoption process of determining whether or not to adopt the candidate structure based on whether or not the first invariant feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied. Even in the twenty-fourth aspect, similar to the twenty-third aspect, the structure of a compound having a desired physical property value (target value of the first invariant feature quantity) can be efficiently searched for, and the three-dimensional structure of the pharmaceutical candidate compound can be efficiently created.

In order to achieve the above-described object, according to a twenty-fifth aspect of the present invention, there is provided a compound creating method of creating a three-dimensional structure of a target compound that is bound to a target protein, the method comprising: an input step of inputting a chemical structure of one or a plurality of compounds, the second feature quantity of the chemical structure calculated using the feature quantity calculating method according to the eighth aspect, and the second feature quantity of a pocket structure whose binding to a pocket that is an active site of the target protein has been confirmed as a target value of the second feature quantity; a candidate structure acquiring step of changing the chemical structure to obtain a candidate structure; a creating feature quantity calculating step of calculating the second feature quantity of the candidate structure using the feature quantity calculating method according to the eighth aspect; a candidate structure adopting step of adopting or rejecting the candidate structure by performing a first adoption process of determining whether or not to adopt the candidate structure based on whether or not the second feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied. Even in the twenty-fifth aspect, similar to the twenty-third and twenty-fourth aspects, the structure of a compound having a desired physical property value (target value of the second feature quantity) can be efficiently searched for, and the three-dimensional structure of the pharmaceutical candidate compound can be efficiently created.

In order to achieve the above-described object, according to a twenty-sixth aspect of the present invention, there is provided a compound creating method of creating a three-dimensional structure of a target compound that is bound to a target protein, the method comprising: an input step of inputting a chemical structure of one or a plurality of compounds, the second invariant feature quantity of the chemical structure calculated using the feature quantity calculating method according to the ninth aspect, and the second invariant feature quantity of a pocket structure whose binding to a pocket that is an active site of the target protein has been confirmed as a target value of the second invariant feature quantity; a candidate structure acquiring step of changing the chemical structure to obtain a candidate structure; a creating feature quantity calculating step of calculating the second invariant feature quantity of the candidate structure using the feature quantity calculating method according to the ninth aspect; a candidate structure adopting step of adopting or rejecting the candidate structure by performing a first adoption process of determining whether or not to adopt the candidate structure based on whether or not the second invariant feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied. Even in the twenty-sixth aspect, similar to the twenty-third to twenty-fifth aspects, the structure of a compound having a desired physical property value (target value of the second invariant feature quantity) can be efficiently searched for, and the three-dimensional structure of the pharmaceutical candidate compound can be efficiently created.

In order to achieve the above-described object, according to a twenty-seventh aspect of the present invention, there is provided a compound creating method of creating a three-dimensional structure of a target compound that is bound to a target biopolymer other than a protein, the method comprising: an input step of inputting a chemical structure of one or a plurality of compounds, the third feature quantity of the chemical structure calculated using the feature quantity calculating method according to the eleventh aspect, and the third feature quantity of a binding compound that is a compound whose binding to the target biopolymer other than the protein has been confirmed as a target value of the third feature quantity; a candidate structure acquiring step of changing the chemical structure to obtain a candidate structure; a creating feature quantity calculating step of calculating the third feature quantity of the candidate structure using the feature quantity calculating method according to the eleventh aspect; a candidate structure adopting step of adopting or rejecting the candidate structure by performing a first adoption process of determining whether or not to adopt the candidate structure based on whether or not the third feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied. Even in the twenty-seventh aspect, similar to the twenty-third to twenty-sixth aspects, the structure of a compound having a desired physical property value (target value of the third feature quantity) can be efficiently searched for, and the three-dimensional structure of the pharmaceutical candidate compound can be efficiently created.

Further, in the twenty-third to twenty-sixth aspects, the concept "chemical structure" includes, in addition to a structure in an initial state (initial structure), a structure in which the initial structure is changed by repeating the process.

As described above, according to the feature quantity calculating method of the present invention, the feature quantity accurately showing the chemical properties of the target structure can be calculated. Further, according to the screening method of the present invention, screening of a pharmaceutical candidate compound can be efficiently performed. Further, according to the compound creating method of the present invention, the three-dimensional structure of a pharmaceutical candidate compound can be efficiently created.

BRIEF DESCRIPTION OF THE DRAWINGS

FIG. 6 is a flowchart showing a procedure for calculating an AAS descriptor for a compound.

FIGS. 12A and 12B are diagrams showing an example of ease of finding hits for various invariant AAS descriptors.

FIGS. 15A and 15B are tables showing an example of a screening result of ligand input.

FIGS. 17A and 17B are tables showing an example of a screening result of target protein input.

DESCRIPTION OF THE PREFERRED EMBODIMENTS

Hereinafter, embodiments of a feature quantity calculating method, a screening method, and a compound creating method of the present invention will be described in detail with reference to the accompanying drawings.

First Embodiment

Figure 1:
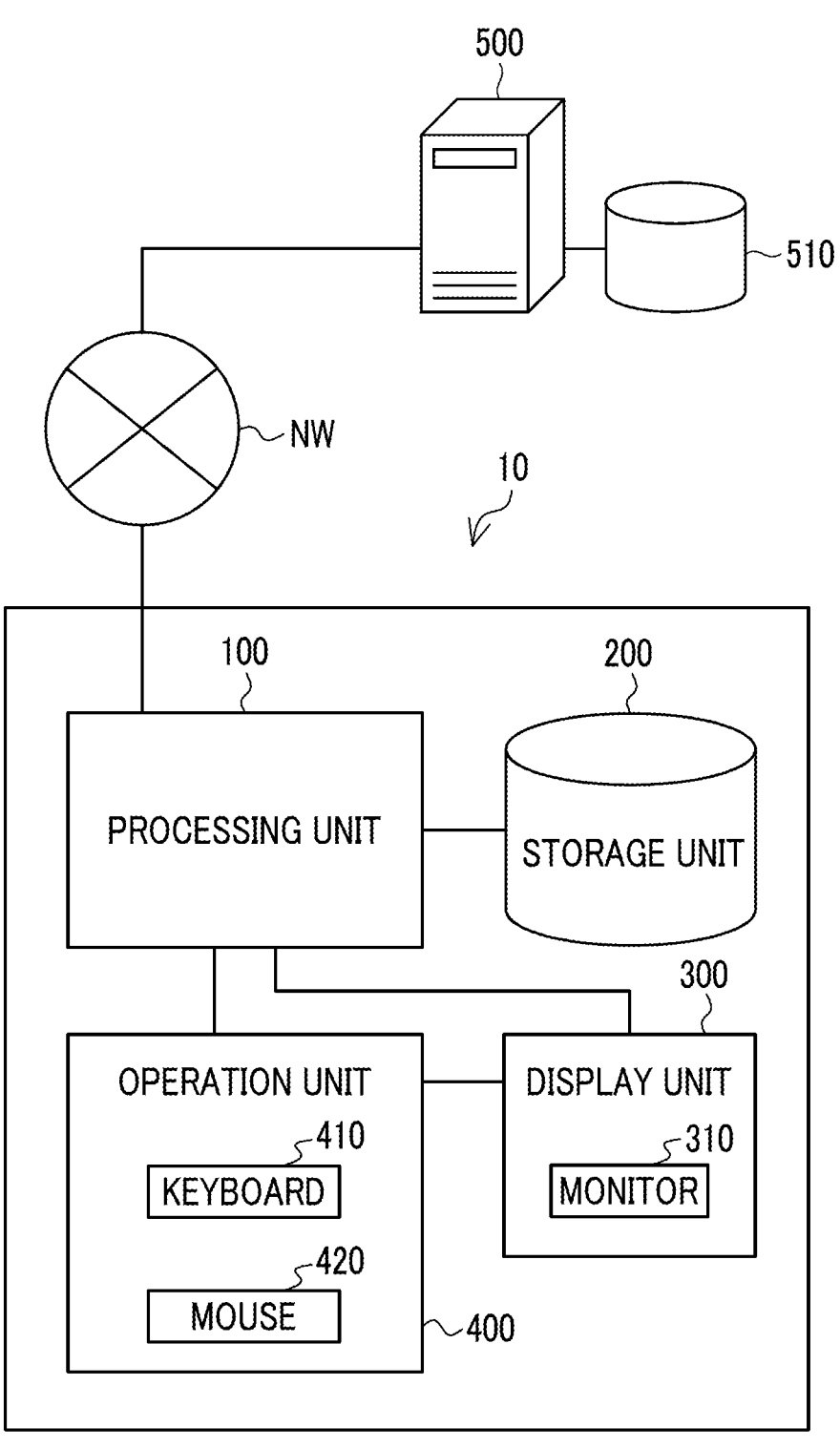
FIG. 1 is a block diagram showing a configuration of a screening device according to a first embodiment.

FIG. 1 is a block diagram showing a configuration of a screening device 10 (a feature quantity calculating device or a screening device) according to a first embodiment. The screening device 10 is a device that calculates a feature quantity of a compound (target structure) and/or a pocket structure (target structure) and extracts (screens) a target compound, and can be realized using a computer. As shown in FIG. 1, the screening device 10 includes a processing unit 100 (processor), a storage unit 200, a display unit 300, and an operation unit 400, and these units are connected to one another to transmit and receive necessary information. These constituent elements may be installed by adopting various installation forms. Respective constituent elements may be installed in one site (in one housing, one room, or the like) or may be installed in places separated from each other and connected via a network. Further, the screening device 10 is connected to an external server 500 and an external database 510 such as a Protein Data Bank (PDB) via a network NW such as the Internet, and information related to structural formulae of compounds and crystal structures of proteins can be obtained as necessary.

<Configuration of Processing Unit>

Figure 2:
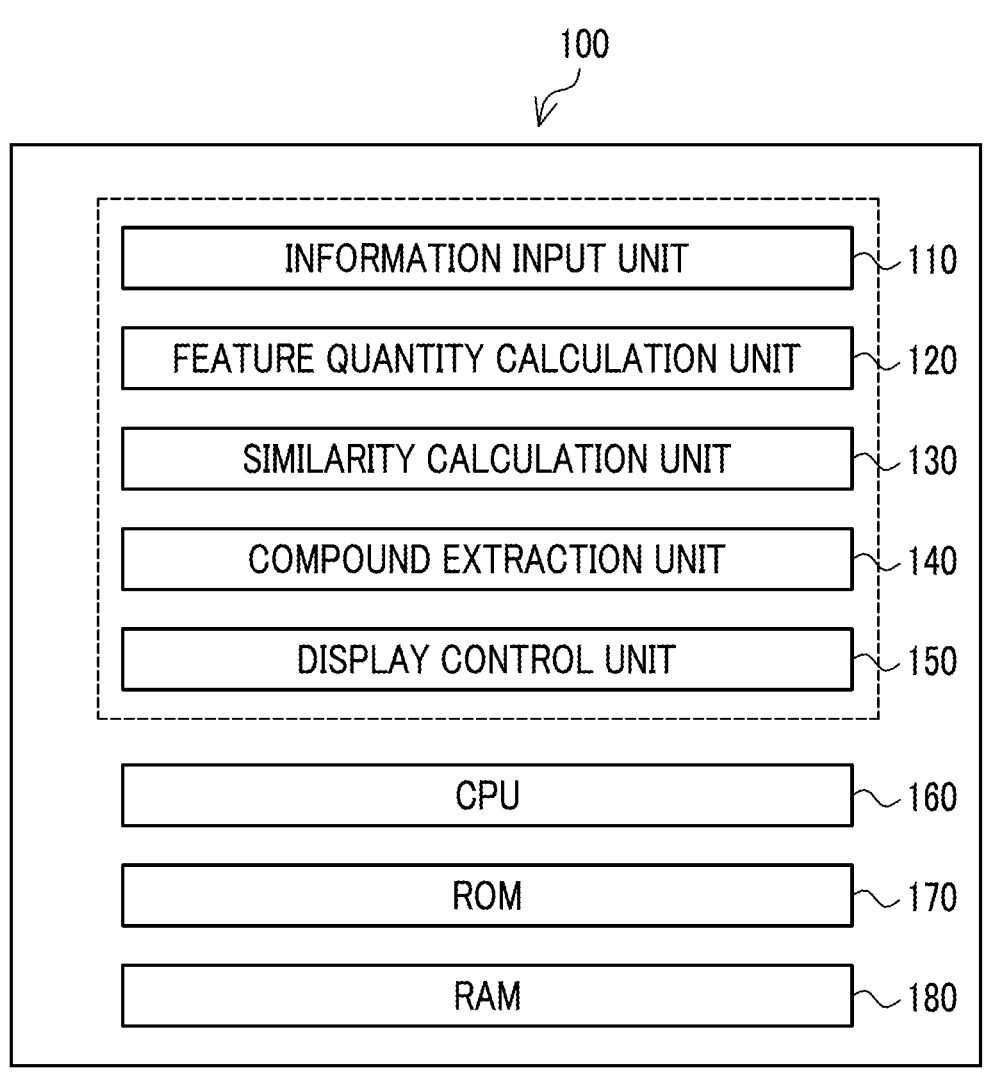
FIG. 2 is a block diagram showing a configuration of a processing unit.

FIG. 2 is a block diagram showing a configuration of the processing unit 100 (processor). The processing unit 100 includes an information input unit 110, a feature quantity calculation unit 120, a similarity calculation unit 130, a compound extraction unit 140, a display control unit 150, a CPU 160 (CPU: Central Processing Unit), a ROM 170 (ROM: Read Only Memory), and a RAM 180 (RAM: Random Access Memory).

The information input unit 110 inputs information related to a structural formula of a compound, an X crystal structure of a target protein, and a pocket position via a recording medium such as a magneto-optical disk (not shown) or a semiconductor memory and/or a network NW. The feature quantity calculation unit 120 (the target structure designation unit, the three-dimensional structure generation unit, and the feature quantity calculation unit) calculates feature quantities (a first feature quantity, a first invariant feature quantity, a second feature quantity, a second invariant feature quantity, a third feature quantity, and a third invariant feature quantity) according to the present invention. The similarity calculation unit 130 (the similarity calculation unit) calculates the similarity between the calculated feature quantities. The compound extraction unit 140 (the compound extraction unit) extracts a target compound from a plurality of compounds based on the similarity. The display control unit 150 controls input information and display of the process result on the monitor 310. The process of calculation of the feature quantity and screening of the target compound using these functions of the processing unit 100 will be described below in detail. Further, the process using these functions is performed under the control of the CPU 160.

The function of each unit of the processing unit 100 described above can be realized using various processors. Various processors include a CPU that is a general-purpose processor that executes software (program) to realize various functions. Further, the various processors described above include a programmable logic device (PLD) serving as a processor that can change the circuit configuration after manufacture of a field programmable gate array (FPGA). Further, the above-described various processors include an exclusive electric circuit serving as a processor having a circuit configuration designed exclusively for executing a specific process such as an application specific integrated circuit (ASIC).

The functions of the respective parts may be realized by one processor or a combination of a plurality of processors. Further, a plurality of functions may be realized by one processor. As an example in which a plurality of functions are configured by one processor, first, as represented by a computer such as a client or a server, a form of one processor which is configured by a combination of one or more CPUs and software and can be realized as a plurality of functions is exemplified. Second, as represented by a system-on-chip (SoC) or the like, there is a form in which a processor that realizes the functions of the entire system by one integrated circuit (IC) chip is used. As described above, various functions are configured using one or more of the above-described various processors as a hardware structure. Further, the hardware structure of these various processors is more specifically an electric circuit (circuitry) in which circuit elements such as semiconductor elements are combined.

In a case where the above-described processor or electric circuit executes software (program), a processor (computer)-readable code of the software to be executed is stored in a non-temporary recording medium such as a ROM 170 (see FIG. 2). The processor refers to the software. The software stored in the non-transitory recording medium includes the feature quantity calculating method, the screening method, and a program (a feature quantity calculating program, a screening program, and a compound creating program) for executing a compound creating method according to the embodiment of the present invention. The code may be recorded on non-transitory recording media such as various magneto-optical recording devices and semiconductor memories instead of the ROM 170. During the process using software, for example, the RAM 180 is used as a temporary storage area, and the data stored in, for example, an electronically erasable and programmable read only memory (EEPROM) (not shown) can also be referred to.

<Configuration of Storage Unit>

Figure 3:
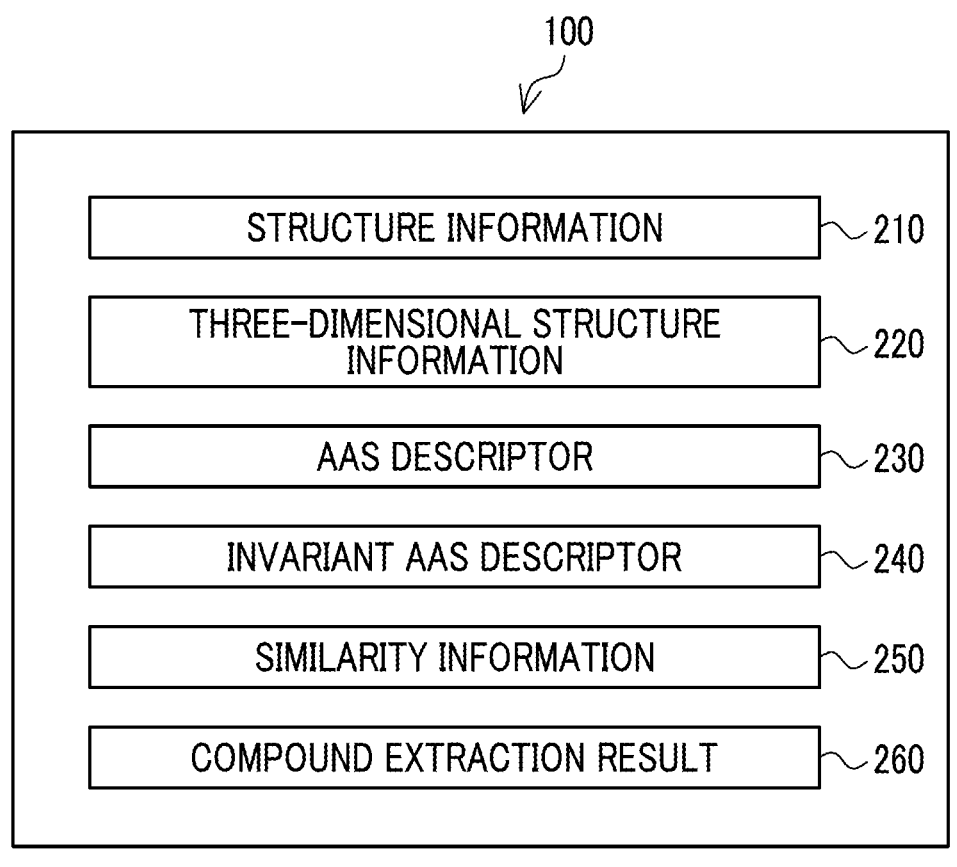
FIG. 3 is a diagram showing information stored in a storage unit.

The storage unit 200 is formed of non-transitory recording media such as a digital versatile disk (DVD), a hard disk, and various semiconductor memories and control units thereof and stores images and information shown in FIG. 3. Structure information 210 includes the structural formula of the compound, the three-dimensional structure of the target protein, and the position of the pocket. Three-dimensional structure information 220 is information related to the three-dimensional structure of the compound and/or the pocket structure, and may be generated from the structure information 210 or may be formed by inputting information that has already been three-dimensionalized. An AAS descriptor 230 (the first feature quantity, the second feature quantity, and the third feature quantity) is a feature quantity showing the cross-sectional area of one or more kinds of probes with respect to a target structure such as a compound or a pocket structure and is calculated by a feature quantity calculating method described below. An invariant AAS descriptor 240 (the first invariant feature quantity, he second invariant feature quantity, and the third invariant feature quantity) is a feature quantity obtained by converting the three-dimensional AAS descriptor 230 into an invariant with respect to rotation of the compound or the pocket structure. Similarity information 250 is information related to the similarity between the feature quantities, and a compound extraction result 260 is information related to the target compound extracted based on the similarity.

Figure 4:
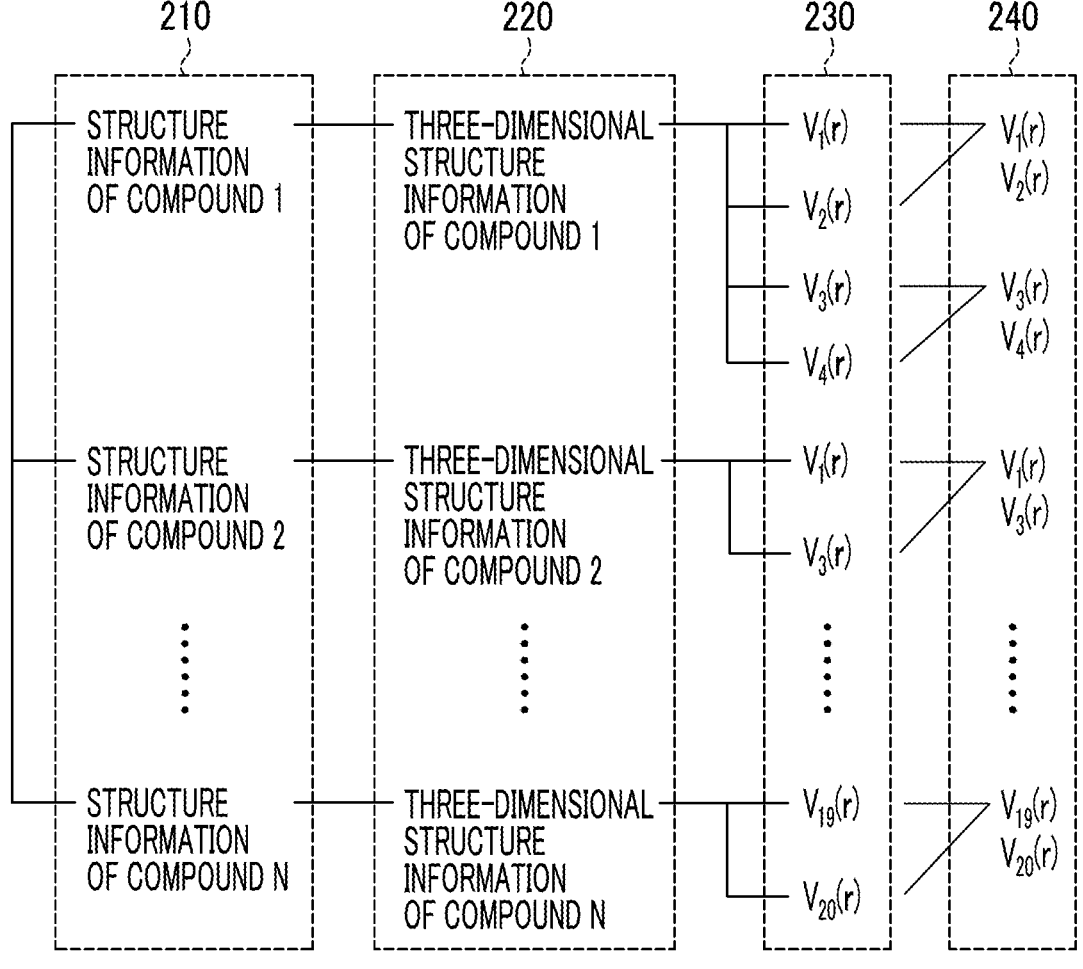
FIG. 4 is a diagram showing a state in which structure information of a compound and a feature quantity thereof are stored in association with each other.

FIG. 4 shows a state in which the structure information 210, the three-dimensional structure information 220, the AAS descriptor 230, and the invariant AAS descriptor 240 are associated with one another and stored in the storage unit 200 for N compounds (N represents an integer of 2 or greater). In FIG. 4, for example, a structural formula can be used as the structure information 210, and a three-dimensionalized structural formula (described below) can be used as the three-dimensional structure information 220. In FIG. 4, the AAS descriptor 230 (described as "$V_a(r)$"; a is a subscript indicating the kind of amino acid) and the invariant AAS descriptor 240 (described as "$V_a(r)$"; a is a subscript indicating the kind of amino acid, r=|r|; r represents an absolute value of the vector r) corresponding to the AAS descriptor 230 for each of twenty kinds of amino acids for each compound are stored in association with each other. Further, the AAS descriptor 230 and the invariant AAS descriptor 240 can be expressed in the form of the closest distance, the scattering angle, the differential scattering cross-sectional area, or the like as described below, but these expressions are collectively described as "$V_a(r)$" and "$V_a$ (r)" for convenience in FIG. 4. Further, the AAS descriptor 230 and the invariant AAS descriptor 240 may be stored not for all twenty kinds of amino acids but for some amino acids according to the number of descriptors used for screening.

A plurality of sets (libraries) of information as shown in FIG. 4 may be stored in the storage unit 200. FIG. 4 shows a state in which information related to compounds is stored, and information related to target proteins can be stored with the same configuration. Further, a method of calculating an AAS descriptor and/or an invariant AAS descriptor using such structure information and three-dimensional structure information will be described below.

<Configuration of Display Unit and Operation Unit>

The display unit 300 includes the monitor 310 (display device) and can display input images, images and information stored in the storage unit 200, results of the process carried out by the processing unit 100, and the like. The operation unit 400 includes a keyboard 410 and a mouse 420 as an input device and/or a pointing device, and execution of the feature quantity calculating method according to the embodiment of the present invention and the operation required for extraction of the target compounds can be performed by a user through these devices and the screen of the monitor 310 (described later). The operations that can be performed by the user include, for example, a processing mode, the kind of descriptor to be calculated, a descriptor used for screening, and designation of a threshold with respect to the similarity.

<Process in Screening Device>

In the screening device 10 with the above-described configuration, calculation of a feature quantity (descriptor) and/or extraction of a target compound can be performed according to the user's instruction via the operation unit 400. Hereinafter, the details of each process will be described.

<Calculation of Feature Quantity>

The screening device 10 is capable of calculating an AAS descriptor and/or an invariant AAS descriptor according to the user's instruction via the operation unit 400.

<Calculation of AAS Descriptor for Compound>

Figure 5:
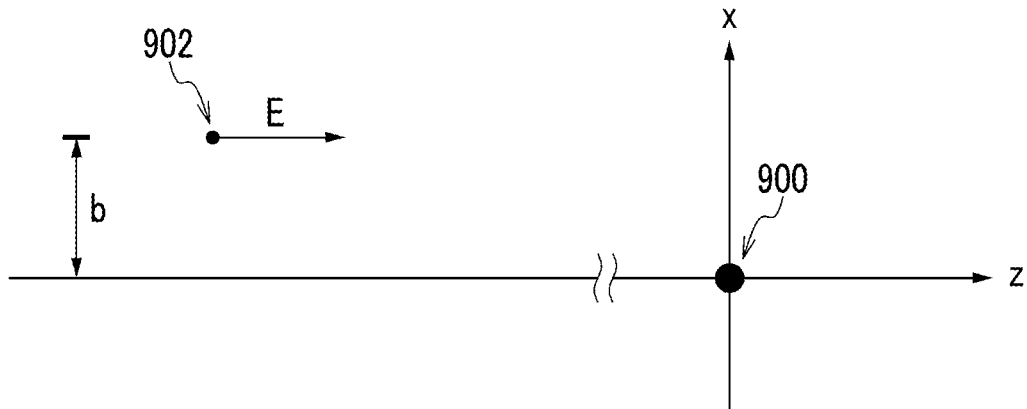
FIG. 5 is a diagram showing a state of acquiring a differential scattering cross-sectional area.

The AAS descriptor is a differential scattering cross-sectional area (the cross-sectional area and the scattering cross-sectional area) in a case where a probe such as an amino acid (twenty kinds such as alanine and valine) is made to collide with a compound (target structure) to be scattered. The differential scattering cross-sectional area can be calculated by performing simulation (execution of the feature quantity calculating method of the present invention) with the screening device 10. In the simulation, as shown in FIG. 5, a situation in which a probe 902 (probe) such as an amino acid collides with a compound 900 disposed at the origin of the coordinate system and is scattered is assumed.

The data (scalar quantity) obtained by the simulation, that is, the data obtained by Expression (1) is a target descriptor, and this descriptor is referred to as "amino acid scattering descriptor (AAS descriptor)" as described above. Further, the total energy (interaction energy+kinetic energy) of the probe such as an amino acid is positive due to the scattered state.

$$d\sigma/d\Omega(E,b,a) \tag{1}$$

Here, E represents an argument for specifying the incident energy of a probe, b represents an argument for specifying the impact parameter of a probe, and a represents an argument for specifying the kind of probe. Further, FIG. 5 shows a case where one amino acid is scattered with a compound, but a peptide in which two or more amino acids are linked may be a probe in the above-described simulation.

In this case, "a" in Expression (1) represents an argument for specifying the kind of peptide.

In order to facilitate handling, the $d\sigma/d\Omega$ (E, b, a) described above can be configured to be invariant to the operation of rotation of the compound, and the descriptor processed in such a manner is also referred to as "invariant amino acid scattering descriptor (invariant AAS descriptor)". For example, the amount obtained by averaging compounds at all angles and calculating $d\sigma/d\Omega$ (E, b, a) with respect to the averaged compound is an amount that is invariant with respect to the operation of rotation and is an expression of "invariant amino acid scattering descriptor (invariant AAS descriptor)". The conversion of the AAS descriptor into an invariant will be described below.

In regard to the AAS descriptor and the invariant AAS descriptor, the amino acid is an example of a probe, and another substance may be a probe as described below. Here, the probe is a structure in which a plurality of points having a real electric charge and generating a van der Waals force are disposed to be separated from each other. In the present invention, the feature quantity in a case where the range of the probe is extended to substances other than amino acids is also referred to as "AAS descriptor" or "invariant AAS descriptor".

FIG. 6 is a flowchart showing a procedure for calculating an AAS descriptor for a compound (target structure). In Step S100, the information input unit 110 (processor) inputs the structural formula of the compound according to the user's instruction via the operation unit 400 or the like. In this manner, the compound represented by the input chemical formula is designated as the target structure (target structure designating step).

Figures 7A, 7B:
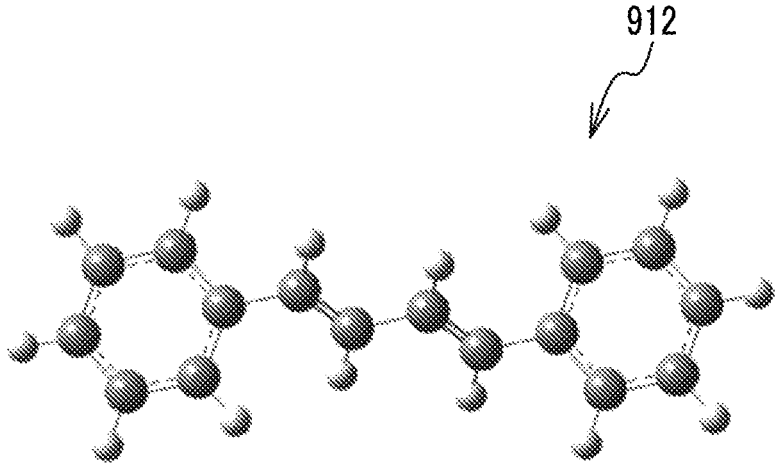
FIGS. 7A and 7B are diagrams showing an example of three-dimensionalization of a structural formula.

The feature quantity calculation unit 120 (processor) three-dimensionalizes the input structural formula to generate a three-dimensional structure of a compound formed of a plurality of atoms (a plurality of unit structures having chemical properties) (Step S102: a three-dimensional structure acquiring step). Various methods are known for three-dimensionalization of a structural formula, and the present invention is not particularly limited to the method used in Step S102. FIGS. 7A and 7B show an example of a three-dimensionalized structural formula. FIG. 7A shows an input structural formula and FIG. 7B shows a three-dimensionalized structural formula. Further, the three-dimensional structure that has already been three-dimensionalized may be acquired (input) instead of inputting the structural formula and three-dimensionalizing the structural formula in Steps S100 and S102 (three-dimensional structure acquiring step). The feature quantity calculation unit 120 sets the centroid of the three-dimensionalized structural formula at r(x, y, z)=0 (origin of the coordinate system) (Step S102: three-dimensional structure acquiring step).

The feature quantity calculation unit 120 calculates an interaction energy $V_{a\mu}(r)$ felt by each atom "$\mu$" of an amino acid "a" (a represents a number representing the kind of amino acid; 1 to 20) (Step S104; probe feature quantity calculating step). Further, "r" in $V_{a\mu}(r)$ represents a vector. As a method of calculating $V_{a\mu}(r)$, a molecular dynamics (MD) method can be adopted, but the present invention is not limited thereto. The amino acid for calculating $V_{a\mu}(r)$ may be a predetermined kind of amino acid or may be determined according to the user's instruction (one or more kinds of amino acids may be used, and a plurality of kinds of amino acids may also be used).

The feature quantity calculation unit 120 calculates the interaction energy $V_a(r)$ felt by the centroid of the amino acid from $V_{a\mu}(r)$ (Step S106: probe feature quantity calculating step) and calculates $V_a(r)$ by averaging the angles with r=0 ((x, y, z)=(0, 0, 0)) at the center with respect to $V_a(r)$ (Step S108: probe feature quantity calculating step). r=|r| (r represents the absolute value of the vector r), that is, r in $V_a(r)$ represents the absolute value of the vector r in $V_{a\mu}(r)$.

Further, the feature quantity calculation unit 120 calculates the closest distance $r_{min,a}$ and the scattering angle $\theta_a$ from $V_a(r)$ calculated in Step S106 as functions of the incident energy E and the impact parameter b described above (Step S110: probe feature quantity calculating step). The closest distance $r_{min,a}$ and the scattering angle $\theta_a$ are expressions of the AAS descriptor as described below. The feature quantity calculation unit 120 calculates the differential scattering cross-sectional area $d\sigma/d\Omega$ (E, b, a) from the closest distance $r_{min,a}$ and the scattering angle $\theta_a$ as functions of the incident energy E and the impact parameter b (Step S112: probe feature quantity calculating step). The differential scattering cross-sectional area $d\sigma/d\Omega$ (E, b, a) is also an expression of the AAS descriptor.

Figure 8A:
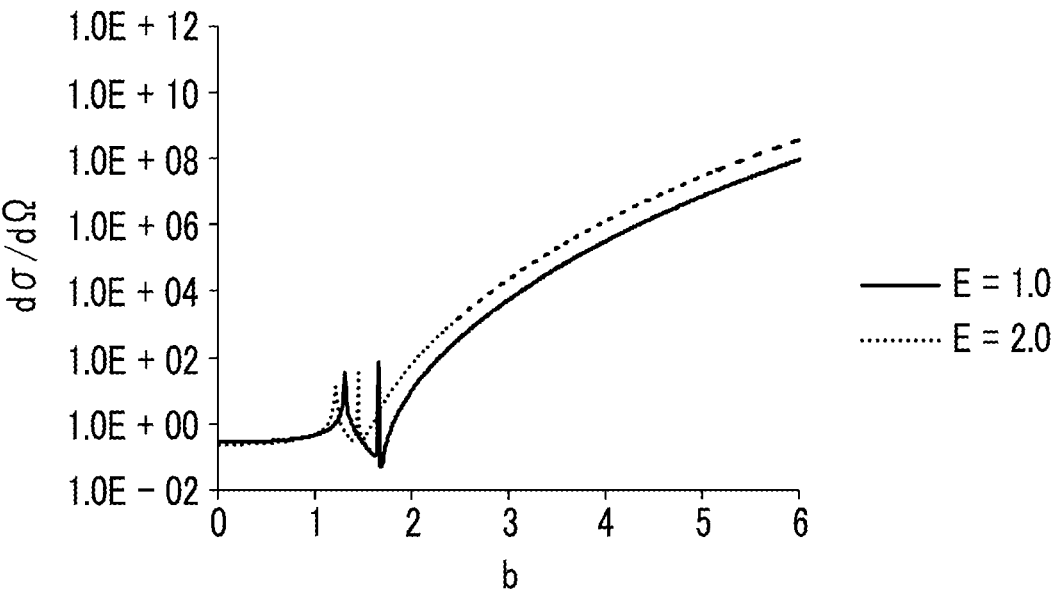
FIGS. 8A and 8B are diagrams showing an example of a differential scattering cross-sectional area.
Figure 8B:
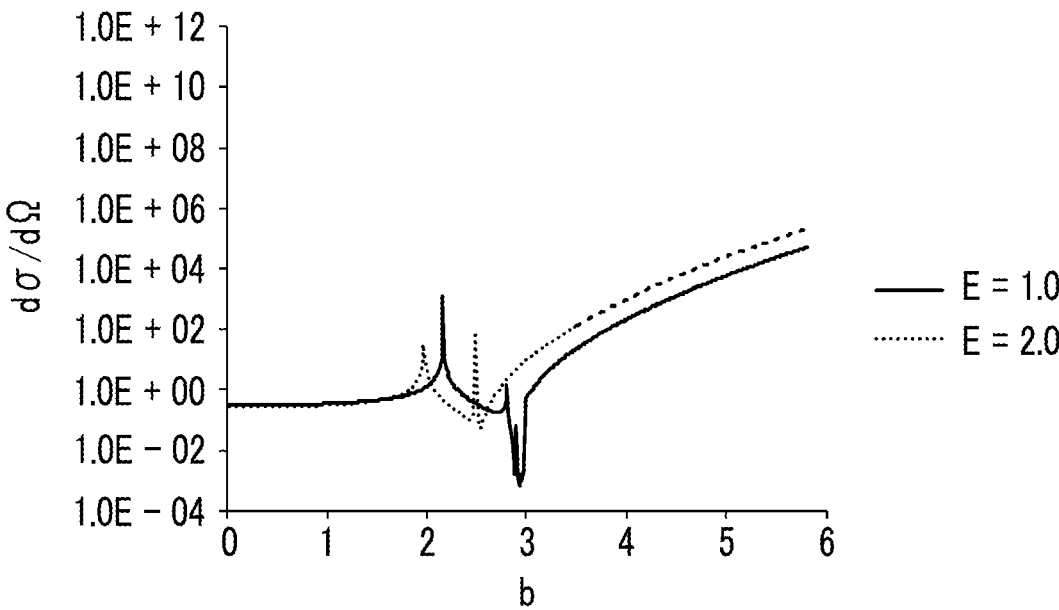
Figure 9A:
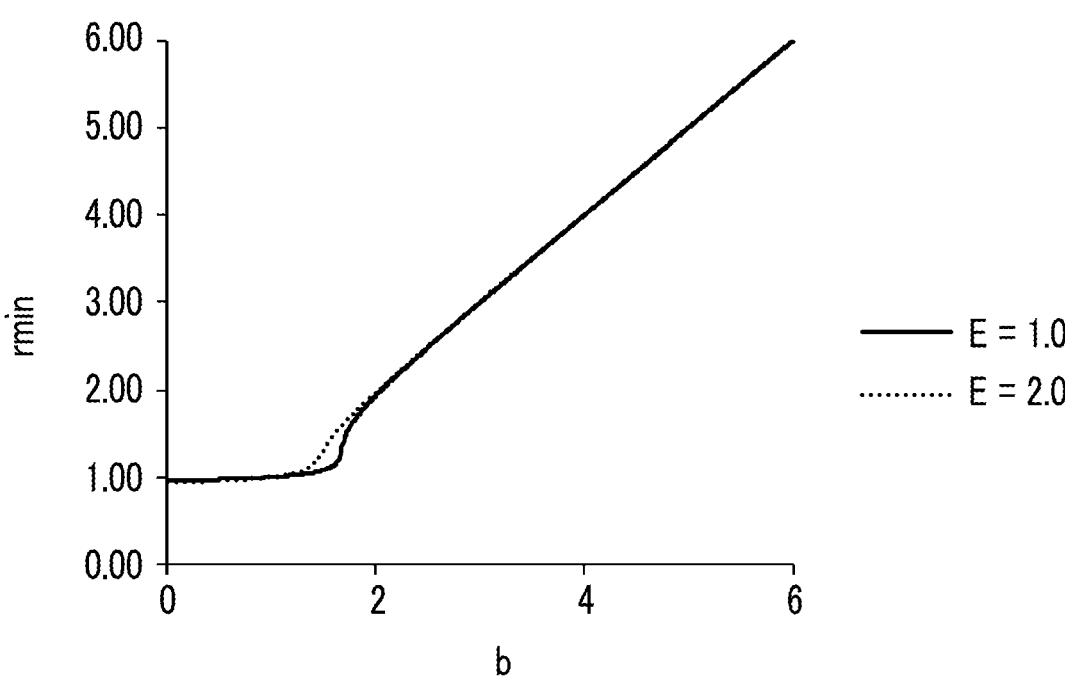
FIGS. 9A and 9B are other diagrams showing an example of a differential scattering cross-sectional area.
Figure 9B:
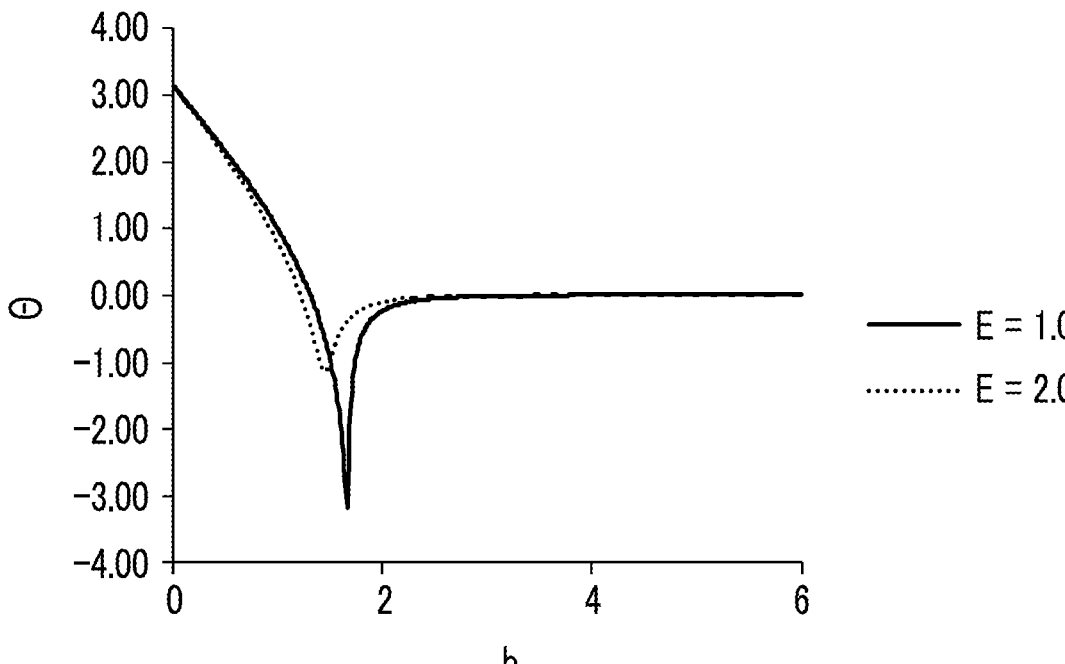

FIGS. 8A and 8B are diagrams showing the differential scattering cross-sectional area of the compound shown in FIGS. 7A and 7B. FIG. 8A is a graph showing the differential scattering cross-sectional area (the AAS descriptor and the first feature quantity) for alanine (amino acid), and FIG. 8B is a graph showing the differential scattering cross-sectional area (first feature quantity) for phenylalanine (amino acid). In addition, FIGS. 9A and 9B are graphs showing the feature quantity (probe is alanine) of the compound shown in FIGS. 7A and 7B in another form. Specifically, FIG. 9A is a graph showing the closest distance $r_{min,a}$ (first feature quantity), and FIG. 9B is a graph showing a scattering angle $\theta_a$.

<Calculation of AAS Descriptor for Pocket Structure>

Figure 10:
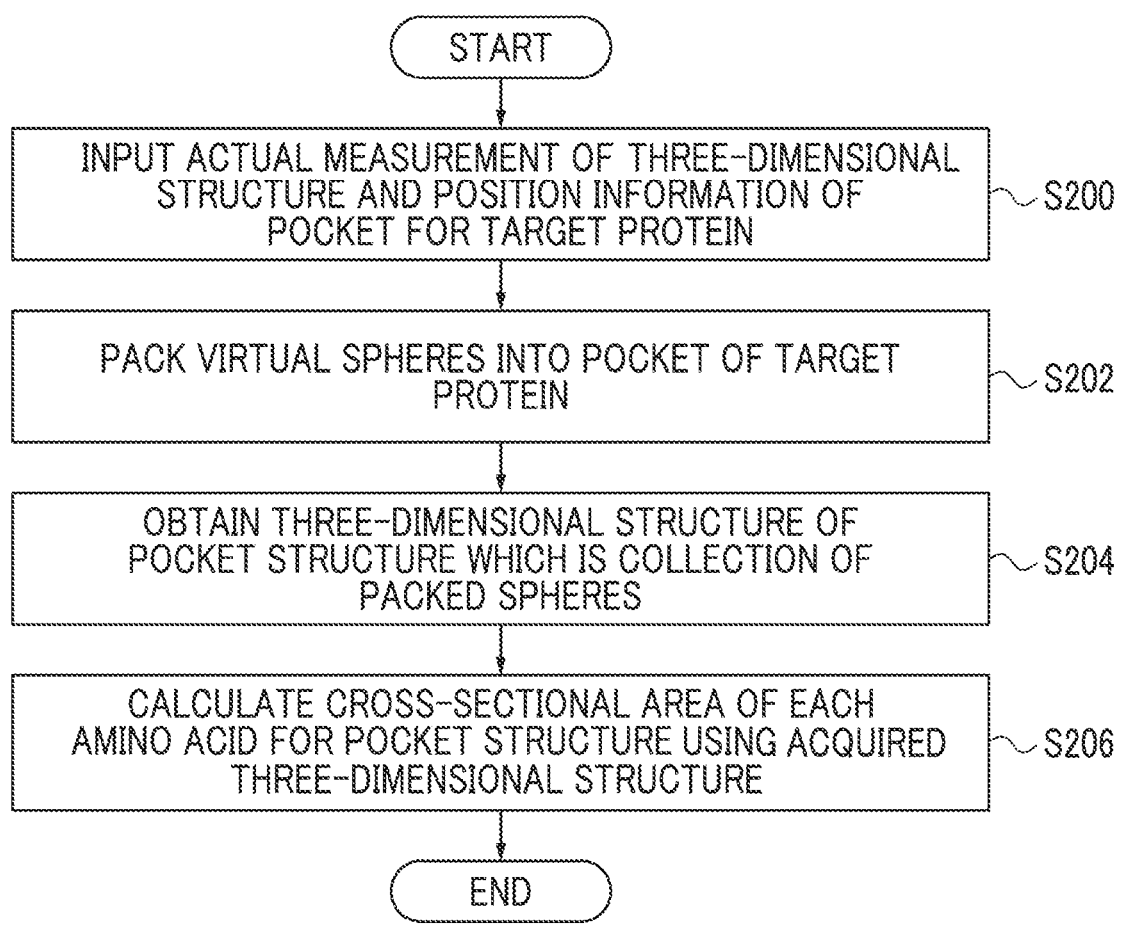
FIG. 10 is a flowchart showing a procedure for calculating an AAS descriptor for a pocket structure.
Figure 11A:
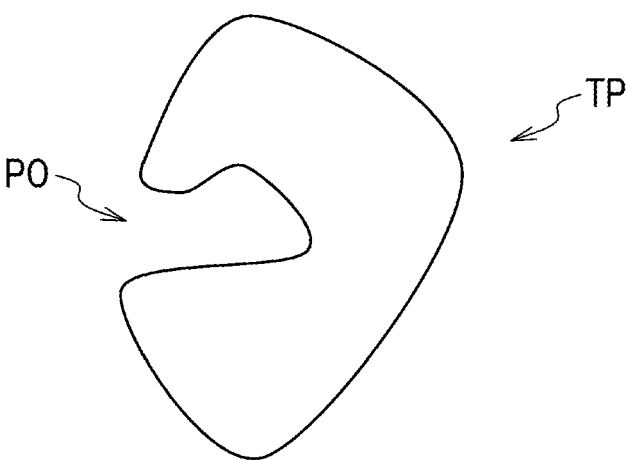
FIGS. 11A and 11B are conceptual diagrams showing a relationship between a target protein and a pocket structure.
Figure 11B:
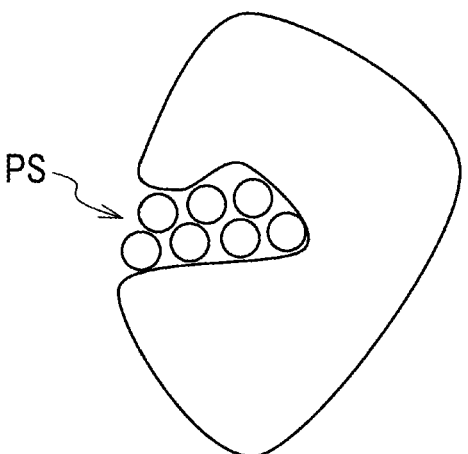

In the screening device 10, a pocket structure that is bound to a target protein is designated as a target structure, and the feature quantity (the AAS descriptor; the second feature quantity) of this pocket structure can also be calculated. The pocket structure is a target structure that is bound to a pocket, which is an active site of the target protein, and the term "active site" indicates a site where the activity of the target protein is promoted or suppressed by the binding of the pocket structure. FIG. 10 is a flowchart showing a procedure for calculating the AAS descriptor for the pocket structure, and FIGS. 11A and 11B are conceptual diagrams showing the relationship between the target protein and the pocket structure.

In the flowchart of FIG. 10, the information input unit 110 inputs the actual measurement of the three-dimensional structure of the target protein and the position information of the pocket (Step S200: target structure designating step). FIG. 11A shows a pocket PO in a target protein TP. The pocket structure is designated as the target structure by the process of Step S200.

The feature quantity calculation unit 120 packs a plurality of virtual spheres (a plurality of unit structures having chemical properties) into the pocket of the target protein (Step S202: the target structure designating step and the three-dimensional structure acquiring step). The term "virtual sphere" can be considered to have chemical properties such as a van der Waals radius and an electric charge, and "packing the virtual spheres" can be performed by simulation (for example, a molecular dynamics method). A collection of the packed virtual spheres (three-dimensional structure) can be obtained as a three-dimensional structure of the pocket structure (target structure) in Step S202 (Step S204:

three-dimensional structure generating step). FIG. 11B shows an example of a pocket structure PS for the target protein TP.

The feature quantity calculation unit 120 calculates the cross-sectional area (second feature quantity; an aspect of the AAS descriptor) of one or more kinds of amino acids for the pocket structure using the acquired three-dimensional structure (Step S206: probe feature quantity calculating step). The feature quantity calculation unit is capable of calculating how amino acids are scattered by the pocket structure. Further, the number of amino acids for calculating the second feature quantity may be one or more kinds (a plurality of kinds of amino acids may be used). Further, the second feature quantity may be calculated for a predetermined kind of amino acid or an amino acid set according to the user's operation. The feature quantity calculation unit 120 stores the calculated AAS descriptor in the storage unit 200 as the AAS descriptor 230 in association with the structure information (structure information 210) and the three-dimensional structure information (three-dimensional structure information 220) of the compound (see FIGS. 3 and 4; the storing step). In a case where the invariant AAS descriptor described below has been calculated, the feature quantity calculation unit 120 associates the AAS descriptor with the invariant AAS descriptor.

<Calculation of AAS Descriptor Using Nucleic Acid Base or the Like as Probe>

In the present invention, deoxyribonucleic acid (DNA), ribonucleic acid (RNA), cell membranes, and polysaccharides, which are biopolymers (compounds) other than proteins can be treated as the targets of drugs. In a case where the feature quantities (the third feature quantity; an aspect of the AAS descriptor) of these target compounds are calculated, and the probe is not an amino acid but another substance (a building block of each target). Specifically, in a case where the targets are DNA, RNA, cell membranes, and polysaccharides, the probes are respectively set as one or more kinds of nucleic acid bases, one or more kinds of lipid molecules, and one or more kinds of monosaccharide molecules. Further, water and one or more kinds of ions may be considered in a case where the feature quantity is calculated using these as probes. Since the drug efficacy of a compound (the binding force with respect to the target such as DNA) is locally exhibited as the result of an interaction between the compound and a nucleic acid base (probe) or the like, in a case where the feature quantities showing the cross-sectional areas of nucleic acid bases or the like are similar between compounds, the compounds have similar binding forces with respect to the targets. That is, compounds having similar third feature quantities exhibit similar drug efficacies. Therefore, the chemical properties of the compound can be accurately determined by the third feature quantity. Further, the third feature quantity can be calculated in the same manner as in a case of the first and second feature quantities (see FIGS. 5 and 6 and the description and the like related thereto).

<Conversion of AAS Descriptor into Invariant>

The above-described AAS descriptor shows the cross-sectional area of an amino acid or the like, but the value changes in a case of occurrence of rotation even with the same compound. Therefore, in the screening device 10 according to the first embodiment, the feature quantity calculation unit 120 (processor) can calculate "invariant AAS descriptor obtained by converting the AAS descriptor into an invariant with respect to rotation of the compound" (the first invariant feature quantity, the second invariant feature quantity, and the third invariant feature quantity) in addition to or in place of the AAS descriptor. Further, conversion into an invariant can be performed according to the same procedures in both cases of a compound and a pocket structure. In a case where an AAS descriptor (the first feature quantity and the third feature quantity) of a compound is used, an invariant AAS descriptor (the first invariant feature quantity and the third invariant feature quantity) of the compound is obtained. Further, in a case where an AAS descriptor (second feature quantity) of the pocket structure is used, an invariant AAS descriptor (second invariant feature quantity) of the pocket structure is obtained.

The closest distance $r_{min,a}$, the scattering angle $\theta_a$, and the differential scattering cross-sectional area $d\sigma/d\Omega$ (E, b, a) calculated from the above-described interaction energy $V_a(r)$ (see Step S106) are examples of the AAS descriptor before conversion into an invariant. The feature quantity calculation unit 120 can calculate the invariant AAS descriptor (the closest distance $r_{min,a}$, the scattering angle $\theta_a$, and the differential scattering cross-sectional area $d\sigma/d\Omega$ (E, b, a); first to third invariants) using $V_a(r)$ (r=|r|, r represents the absolute value of the vector r; see Step S108) obtained by averaging the angles of $V_a(r)$. Further, the AAS descriptor is an invariant with respect to translation from the beginning, and the target of conversion into an invariant is only rotation.

The feature quantity calculation unit 120 stores the calculated invariant AAS descriptor in the storage unit 200 as the invariant AAS descriptor 240 in association with the structure information (structure information 210), the three-dimensional structure information (three-dimensional structure information 220), and the original AAS descriptor 230 of the compound (see FIGS. 3 and 4; the storing step). In a case where the invariant AAS descriptor is calculated using the AAS descriptor of two different kinds of amino acids, a plurality of associations between the AAS descriptor and the invariant AAS descriptor may be present.

According to the invariant AAS descriptor described above, since compounds having similar descriptors exhibit similar drug efficacies (for example, binding to a target protein), the chemical properties of the target structure (a compound, a pocket structure, and a biopolymer) are accurately exhibited. According to the invariant AAS descriptor in which the AAS descriptor is converted into an invariant, the feature quantity is easily handled and the data capacity can be easily reduced while comparison (determination of the drug efficacy) of compounds based on the descriptor is accurately performed by performing conversion into an invariant using the AAS descriptor of two kinds of different amino acids. Further, according to the invariant AAS descriptor, hits can be easily found.

<Easiness of Finding Hits Using Invariant AAS Descriptor>

The easiness of finding hits using invariant AAS descriptors is evaluated according to the following procedures 1 to 5.

(Procedure 1) X hit compounds and Y non-hit compounds are mixed with a certain target (target protein or the like).

(Procedure 2) Invariant AAS descriptors of all (X+Y) compounds are calculated.

(Procedure 3) The similarity of each descriptor is calculated.

(Procedure 4) The (X+Y) compounds are divided into teams based on the similarities of the invariant AAS descriptors.

(Procedure 5) It is checked whether the teams in which hits are collected are mechanically generated.

FIGS. 12A and 12B show an example (result obtained from comparison with a case of random team division) of easiness of finding hits for each team (=expectation value; number of hits x hit content rate) in teams created for a protein ABL1 (kinase). Further, FIG. 12A shows expectation values of the number of hits for (1) an invariant AAS descriptor (probe is an amino acid; first invariant feature quantity), (2) invariant plural ions (both probes are $Na^+$ and $Cl^-$ which are monoatomic ions; third invariant feature quantity), (3) an invariant AAS descriptor and ions (probes are an amino acid and $Na^+$ and $Cl^-$; fourth invariant feature quantity), (4) an invariant dipole (probe is a dipole; fifth invariant feature quantity), (5) an invariant AAS descriptor and a dipole (probes are an amino acid and a dipole; sixth invariant feature quantity), (6) invariant plural ions and a dipole (probes are $Na^+$ and $Cl^-$, and a dipole; seventh invariant feature quantity), and (7) an invariant AAS descriptor, plural ions, and a dipole (probes are an amino acid, $Na^+$ and $Cl^-$, and a dipole; eighth invariant feature quantity). In addition, FIG. 12B shows expectation values of the number of hits for (1) an invariant AAS descriptor (probe is an amino acid; first invariant feature quantity, same as (1) in FIG. 12A), (8) an invariant monoatomic ion (probe is Nat; third invariant feature quantity), (9) an invariant AAS descriptor and a monoatomic ion (probes are an amino acid and Nat; fourth invariant feature quantity), (10) an invariant monoatomic ion and a dipole (probes are $Na^+$ and a dipole; seventh invariant feature quantity), and (11) an invariant AAS descriptor, a monoatomic ion, and a dipole (probes are an amino acid, $Na^+$, and a dipole; eighth invariant feature quantity).

As shown in the results of FIGS. 12A and 12B, it can be seen that teams having more hits are generated as compared to random team division in a case where the invariant AAS descriptor is used. In FIG. 12, the team numbers vary depending on the team division method (random, the invariant AAS descriptor), and thus the superiority of the team division is determined not by comparing the expectation values with the same team number but by verifying "whether teams with high expectation values (having more hits) are included or not".

<Invariant AAS Descriptor of Compound that is Bound to Target Protein/Compound that is not Bound to Target Protein>

Figure 13A:
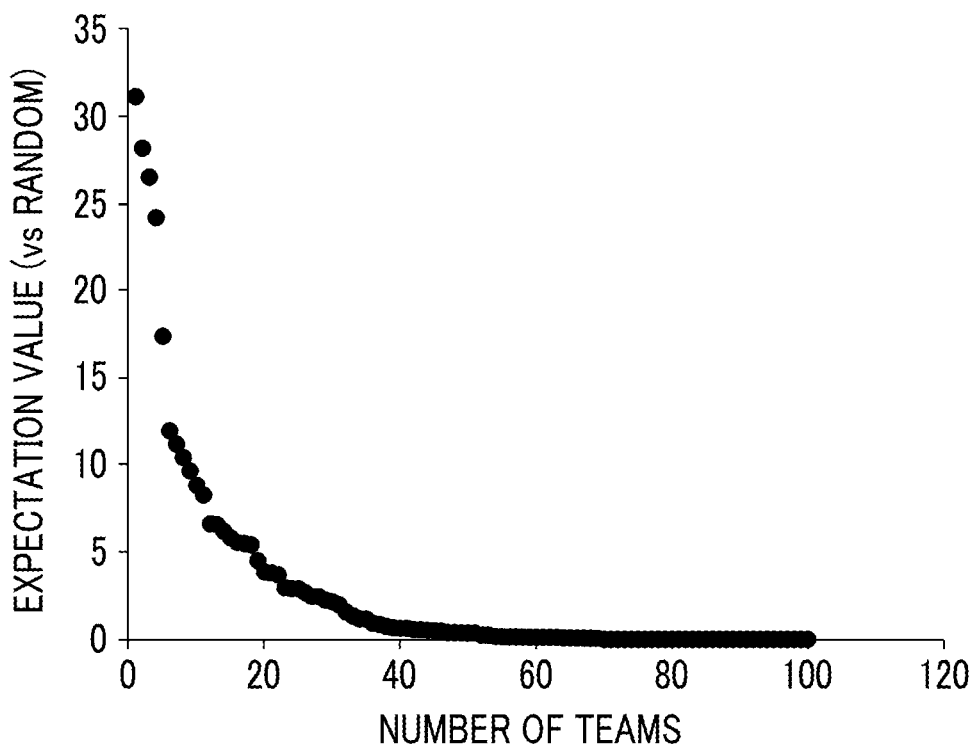
FIGS. 13A and 13B are diagrams showing ease of finding hits for a compound that is bound to a target protein and a compound that is not bound to the target protein.
Figure 13B:
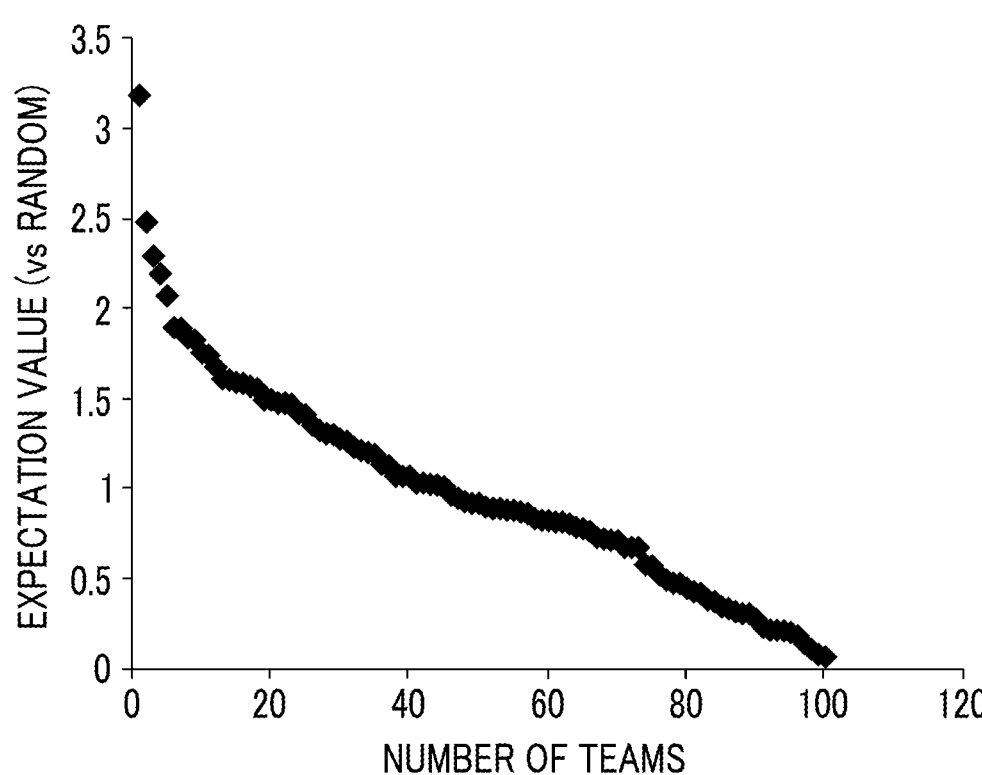

According to the feature quantities (the AAS descriptor, the invariant AAS descriptor, and the amino acid scattering descriptor) used in the present invention, for example, a target compound that is bound to a target protein can be extracted or created as described with reference to FIGS. 12A and 12B. However, in addition to this, for example, a target compound that is not bound to the target protein can be extracted or created. FIG. 13A shows an example (probe is an amino acid) of expectation values (compared with the case of random team division) of the number of hits of the compound (first target compound) that is bound to the target protein (the same protein ABL1 as in the example of FIGS. 12A and 12B) calculated based on the invariant AAS descriptor, and FIG. 13B shows an example of expectation values of the number of hits of the compound (second target compound) that is not bound to the target protein calculated based on the same invariant AAS descriptor as described above. As can be seen in FIGS. 13A and 13B, hits can be easily found for not only the compound (first target compound) that is bound to the target protein but also the compound (second target compound) that is not bound to the target protein by using the feature quantity according to the present invention. Here, the binding force can be measured with, for example, IC50 (half maximal (50%) inhibitory concentration; 50% inhibitory concentration). In this case, a value of approximately 100 to 1000 μM can be used as the threshold value of "bound to/not bound to", but indices or values different depending on the problem (which characteristic is to be evaluated) may also be used.

Further, since the expression "not bound to a specific protein" denotes that "effective for description of a compound having no toxicity (low toxicity)", a compound having no toxicity (low toxicity) can be searched for or created by using the similarity between the AAS descriptor and the invariant AAS descriptor.

<Effects of Feature Quantity Calculating Method>

As described above, the screening device 10 (the feature quantity calculating device and the screening device) according to the first embodiment is capable of calculating the feature quantity (the AAS descriptor and the invariant AAS descriptor) accurately showing the chemical properties of the target structure using the feature quantity calculating method according to the embodiment of the present invention and the program that executes the feature quantity calculating method (feature quantity calculating program).

<Extraction of Target Compound (Screening)>

Extraction of a target compound (pharmaceutical candidate compound) from a plurality of compounds using the AAS descriptor and the invariant AAS descriptor described above will be described. The target compound is extracted, for example, in a mode (first mode) of performing extraction based on a descriptor (the AAS descriptor and the invariant AAS descriptor) of a ligand, in a mode (second mode) of performing extraction based on a descriptor (the AAS descriptor and the invariant AAS descriptor) of a pocket structure of a target protein, or in a mode (third mode) of performing extraction based on a descriptor (the AAS descriptor and the invariant AAS descriptor) of a binding compound (compound whose binding to a target biopolymer other than a protein has been confirmed). The mode for extraction can be selected from the above-described modes according to the operation of the user via the operation unit 400.

<Screening of Ligand Input>

Figure 14:
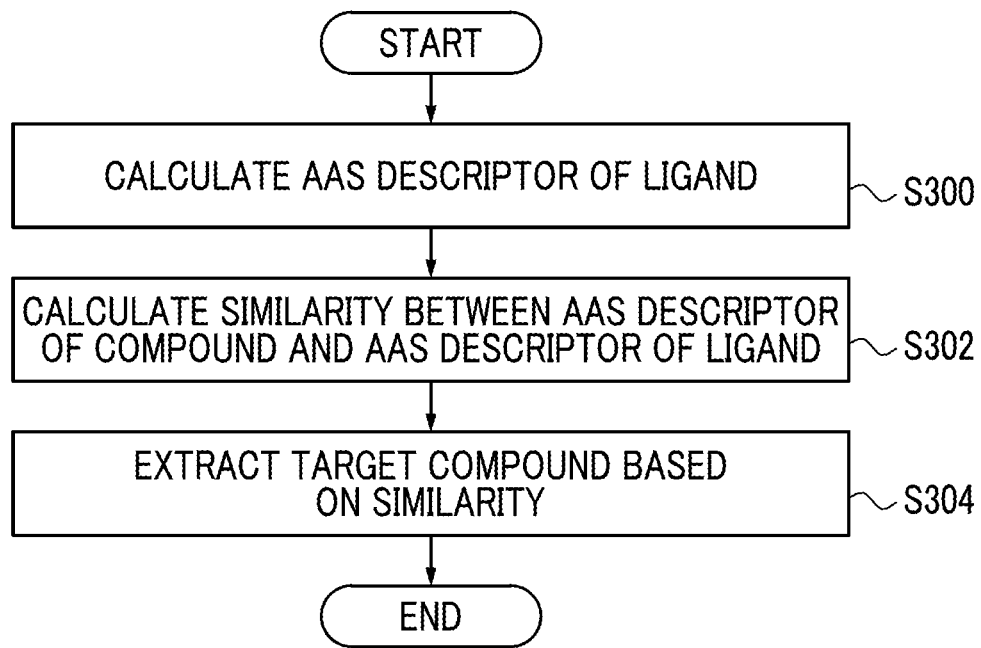
FIG. 14 is a flowchart showing a procedure for extracting a compound based on an AAS descriptor of a ligand.

FIG. 14 is a flowchart showing a procedure for screening (first mode) using an AAS descriptor of a ligand. After the start of the process, the feature quantity calculation unit 120 calculates an AAS descriptor of the ligand (Step S300: the screening feature quantity calculating step). Since the ligand is a compound whose binding to the target protein has been confirmed, the AAS descriptor in Step S300 can be calculated according to the procedure shown in the flowchart of FIG. 6.

As described above with reference to FIG. 4, in the screening device 10, the three-dimensional structure of the compound formed of a plurality of atoms and the AAS descriptor (the first feature quantity) corresponding to the three-dimensional structure are stored in the storage unit 200 in association with each other for each of the plurality of compounds. The similarity calculation unit 130 calculates the similarity between the AAS descriptor of the compound and the AAS descriptor of the ligand calculated in Step S400 (Step S302: the similarity calculating step). After the calculation of the similarity, the compound extraction unit 140 extracts the target compound based on the similarity (Step S304: the target compound extracting step). As described above, in a case where AAS descriptors are similar, since similar drug efficacies (binding to the target protein) are exhibited, a compound having drug efficacy similar to that of the ligand (that is, a target compound serving as a pharmaceutical candidate) can be extracted by using the similarity of the AAS descriptor. Further, the extraction of the target compound based on the similarity (Step S3404) can be specifically performed by "extracting a compound having a similarity greater than or equal to the threshold" or "extracting a compound in a descending order of the similarity".

FIG. 14 shows the procedure for screening using an AAS descriptor, but the screening using an invariant AAS descriptor can also be performed in the same procedure as described above. Specifically, the feature quantity calculation unit 120 calculates the invariant AAS descriptor (the first invariant feature quantity) of the ligand according to the procedure of FIG. 6 and Equations (2) and (3), and the similarity calculation unit 130 calculates the similarity between the compound stored in the storage unit 200 and the invariant AAS descriptor. After the calculation of the similarity, the compound extraction unit 140 extracts the target compound based on the similarity. Specifically, the target compound can be extracted based on the similarity in the same manner as the extraction of the AAS descriptor.

FIGS. 15A and 15B are tables showing an example of a screening result of ligand input. FIG. 15A shows the result in a case of "extraction of a compound having a similarity greater than or equal to the threshold" using an AAS descriptor, and FIG. 15B shows the result in a case of "extraction of a compound in a descending order of the similarity" using an invariant AAS descriptor. In FIG. 15A, the compound is extracted based on the AAS descriptor (various expressions are collectively described as "$V_a(r)$" as in the description of FIG. 4) for an amino acid 1, but the compound may be extracted based on the AAS descriptor (for example, $V_2(r)$) for other amino acids (amino acids 2 to 20). In addition, the similarities (the similarity between the values of $V_1(r)$ and the similarity between the values of $V_2(r)$) of a plurality of AAS descriptors (for example, $V_1(r)$ and $V_2(r)$) for different amino acids are respectively calculated, and compounds may be extracted based on the results. The number of kinds of the AAS descriptors used for extraction of a compound may be one, but extraction of a compound based on the similarity can be accurately performed using a plurality of kinds of AAS descriptors. Further, in a case where a plurality of kinds of AAS descriptors are used, the combination of amino acids among the descriptors is not particularly limited (for example, a combination of $V_1(r)$ and $V_2(r)$ or a combination of $V_3(r)$ and $V_4(r)$ may be used).

Similarly, in FIG. 15B, a compound is extracted based on an invariant AAS descriptor ($V_1(r)$ and $V_2(r)$) for the amino acids 1 and 2, but another combination of amino acids (for example, $V_3(r)$ and $V_4(r)$ with amino acids 3 and 4) may be used to calculate the invariant AAS descriptor. In addition, a compound may be extracted based on a plurality of invariant AAS descriptors (for example, the similarity between $V_1(r)$ and $V_2(r)$ and the similarity between $V_3(r)$ and $V_4(r)$ are used) with different combinations of amino acids (for example, $V_1(r)$ and $V_2(r)$ and $V_3(r)$ and $V_4(r)$. The number of kinds of the invariant AAS descriptors used for extraction of a compound may be one, but extraction of a compound based on the similarity can be accurately performed by using a plurality of kinds of invariant AAS descriptors. Further, in a case where a plurality of kinds of invariant AAS descriptors are used, the combination of amino acids between the descriptors is not particularly limited (for example, $V_1(r)$ and $V_2(r)$, and $V_3(r)$ and $V_4(r)$ may be used, or $V_1(r)$ and $V_2(r)$, and $V_1(r)$ and $V_3(r)$ may be used). The processing unit 100 (the feature quantity calculation unit 120, the similarity calculation unit 130, and the compound extraction unit 140) may determine which amino acid is to be used for calculation of the descriptor and the similarity according to the user's instruction via the operation unit 400, but the determination may be made by the processing unit 100 regardless of the user's instruction.

Further, the threshold of the similarity is set to 80% in FIG. 15A, and the number of times of extraction is set to 100 in FIG. 15B, but these values are merely examples. The threshold and the number of times of extraction can be set according to the conditions, for example, the accuracy of screening. The setting can be performed in response to a user input via the operation unit 400. Further, "compound is extracted in a descending order of the similarity" may be employed in a case where an AAS descriptor is used in contrast to FIGS. 15A and 15B, and "compound having a similarity greater than or equal to the threshold is extracted" may be employed in a case where an invariant AAS descriptor is used. The compound extraction unit 140 stores the extraction result as shown in FIGS. 15A and 15B in the storage unit 200 as the compound extraction result 260 (see FIG. 3).

<Screening of Target Protein Input>

Figure 16:
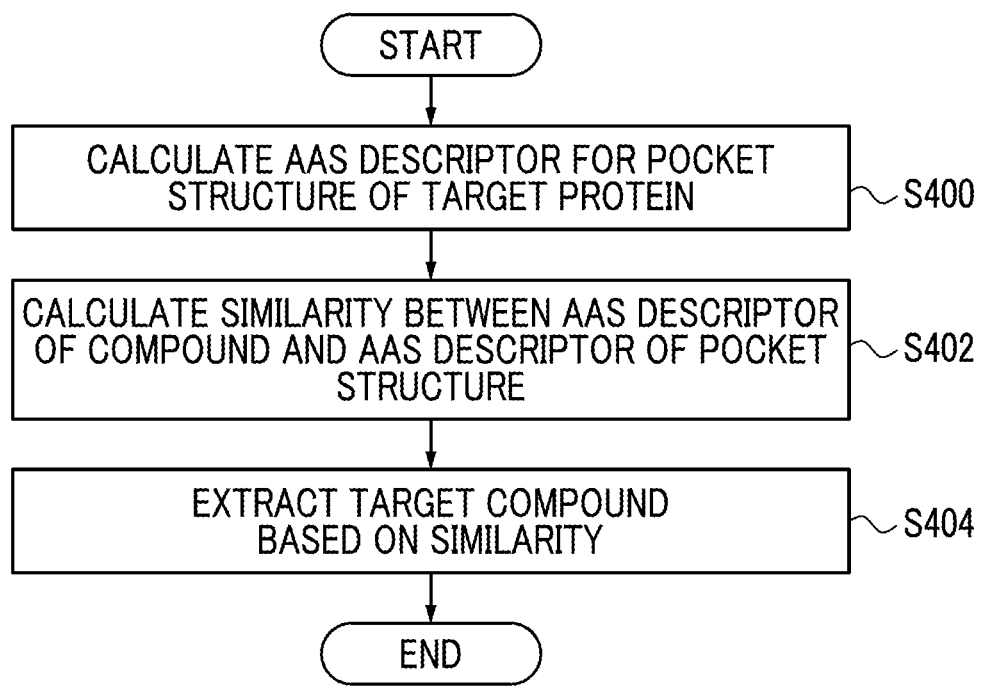
FIG. 16 is a flowchart showing a procedure for screening of a pocket structure using an AAS descriptor.

FIG. 16 is a flowchart showing a procedure for screening (second mode) of a pocket structure of a target protein using an AAS descriptor. After the start of the process, the feature quantity calculation unit 120 calculates an AAS descriptor for the pocket structure of the target protein (Step S400: the screening feature quantity calculating step). The AAS descriptor in Step S400 can be calculated according to the procedure shown in the flowchart of FIGS. 11A and 11B. The similarity calculation unit 130 calculates the similarity between the AAS descriptor of the compound and the AAS descriptor of the pocket structure calculated in Step S400 (Step S402: the similarity calculating step). After the calculation of the similarity, the compound extraction unit 140 extracts the target compound based on the similarity (Step S404: the compound extracting step). Similar to the case of the ligand input described above, the extraction of the target compound based on the similarity (Step S404) can be specifically performed by "extracting a compound having a similarity greater than or equal to the threshold" or "extracting a compound in a descending order of the similarity".

Even in a case of using the invariant AAS descriptor, a target compound can be extracted according to the same procedure as in the flowchart of FIG. 16.

FIGS. 17A and 17B are tables showing an example of a screening result of target protein input. FIG. 17A shows the result in a case of "extraction of a compound having a similarity greater than or equal to the threshold" using an AAS descriptor, and FIG. 17B shows the result in a case of "extraction of a compound in a descending order of the similarity" using an invariant AAS descriptor. The threshold of the similarity and the number of times of extraction can be set according to the conditions, for example, the accuracy of screening. The setting can be performed in response to a user input via the operation unit 400. Further, "compound is extracted in a descending order of the similarity" may be employed in a case where an AAS descriptor is used in contrast to FIGS. 17A and 17B, and "compound having a similarity greater than or equal to the threshold is extracted" may be employed in a case where an invariant AAS descriptor is used.

Even in a case of screening for the target protein input, the kind of amino acid may be changed in the same manner as in the case of screening for the ligand input (see FIGS. 14, 15A, and 15B and the description related thereto), or a plurality of descriptors of different amino acids (the AAS descriptor and the invariant AAS descriptor) may be used.

The number of kinds of the descriptors used for extraction of a compound may be one, but extraction of a compound based on the similarity can be accurately performed using a plurality of kinds of descriptors. Further, in a case where a plurality of kinds of descriptors are used, the combination of amino acids among the descriptors is not particularly limited. The processing unit 100 (the feature quantity calculation unit 120, the similarity calculation unit 130, and the compound extraction unit 140) may determine which amino acid is to be used for calculation of the descriptor and the similarity according to the user's instruction via the operation unit 400, but the determination may be made by the processing unit 100 regardless of the user's instruction.

The compound extraction unit 140 stores the extraction result as shown in FIGS. 17A and 17B in the storage unit 200 as the compound extraction result 260 (see FIG. 3).

<Screening for Input of Target Biopolymer Other than Protein>

The screening device 10 according to the first embodiment can also extract a target compound that is bound to a target biopolymer other than a protein. In this case, screening is performed using the third feature quantity in the same procedure as in the flowcharts of FIGS. 14 and 16 described above (third mode).

<Effect of Screening Device>

As described above, the screening device 10 according to the first embodiment is capable of efficiently screening a pharmaceutical candidate compound by the screening method (and the program causing a computer to execute the screening method) according to the embodiment of the present invention using the feature quantity (the AAS descriptor and the invariant AAS descriptor) calculated by the feature quantity calculating method (the program causing a computer to execute the feature quantity calculating method) according to the embodiment of the present invention.

Second Embodiment

Figure 18:
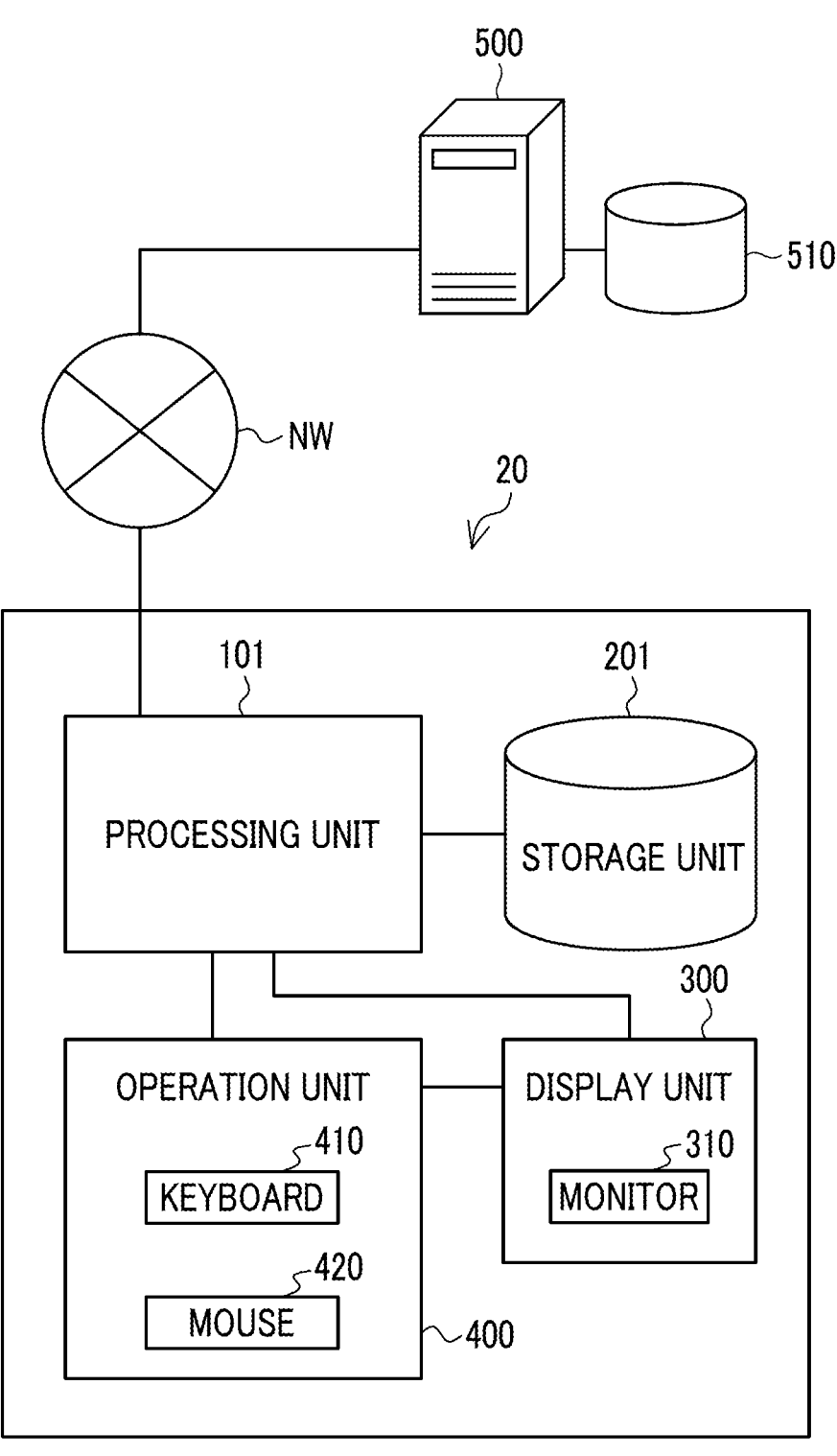
FIG. 18 is a block diagram showing a configuration of a compound creating device according to a second embodiment.

A compound creating device according to a second embodiment of the present invention will be described. FIG. 18 is a block diagram showing a configuration of a compound creating device 20 (a feature quantity calculating device and a compound creating device). Further, the same elements as those in the first embodiment are denoted by the same reference numerals, and detailed description thereof will not be provided.

Figure 19:
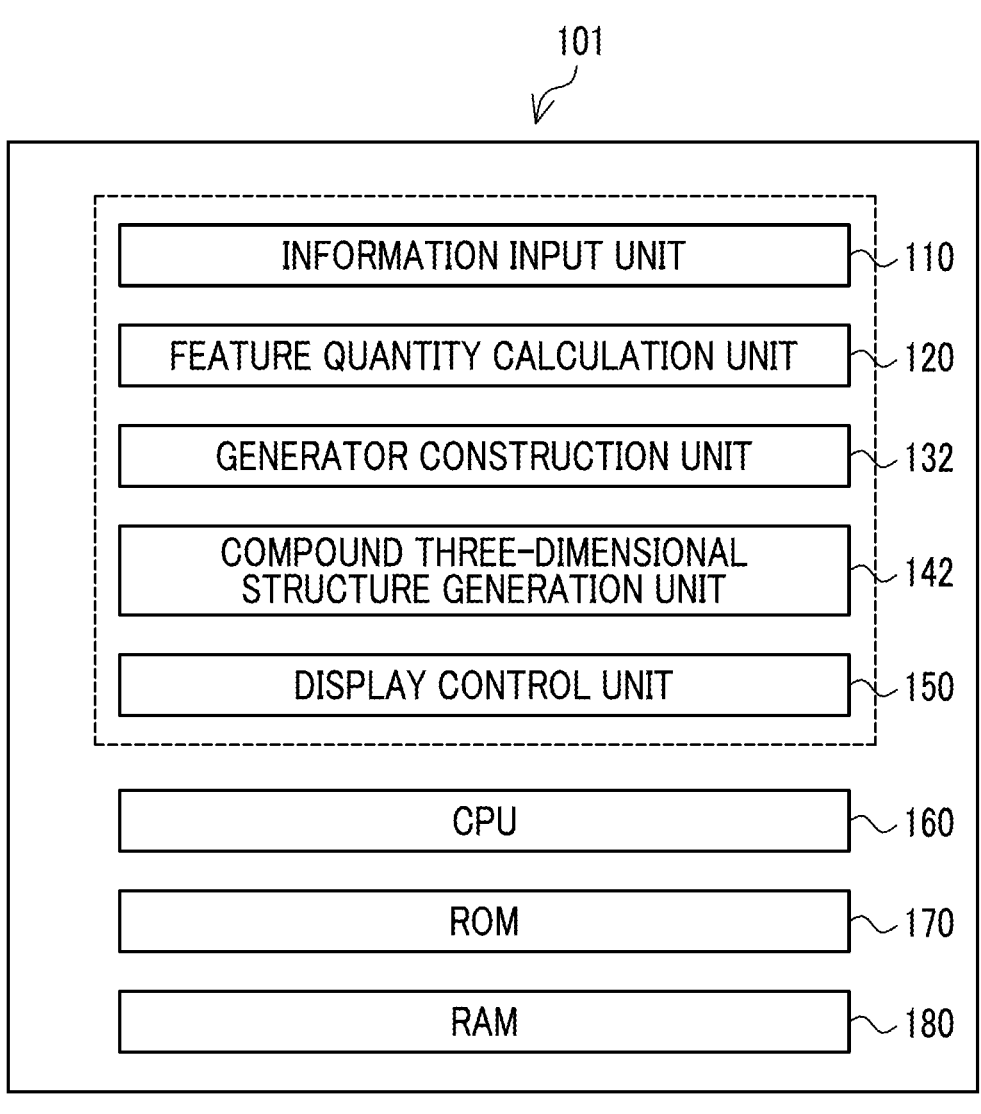
FIG. 19 is a diagram showing a configuration of a processing unit.

The compound creating device 20 includes a processing unit 101. The processing unit 101 is formed as shown in FIG. 19 and includes an information input unit 110, a feature quantity calculation unit 120 (creating feature quantity calculation unit), a generator construction unit 132 (generator construction unit), a compound three-dimensional structure generation unit 142 (compound three-dimensional structure generation unit), and a display control unit 150. The functions of the information input unit 110, the feature quantity calculation unit 120, and the display control unit 150 are respectively the same as the information input unit 110, the feature quantity calculation unit 120, and the display control unit 150 in the above-described screening device 10. The functions of these units can be realized using various processors in the same manner as described above in the section of the screening device 10.

Figure 20:
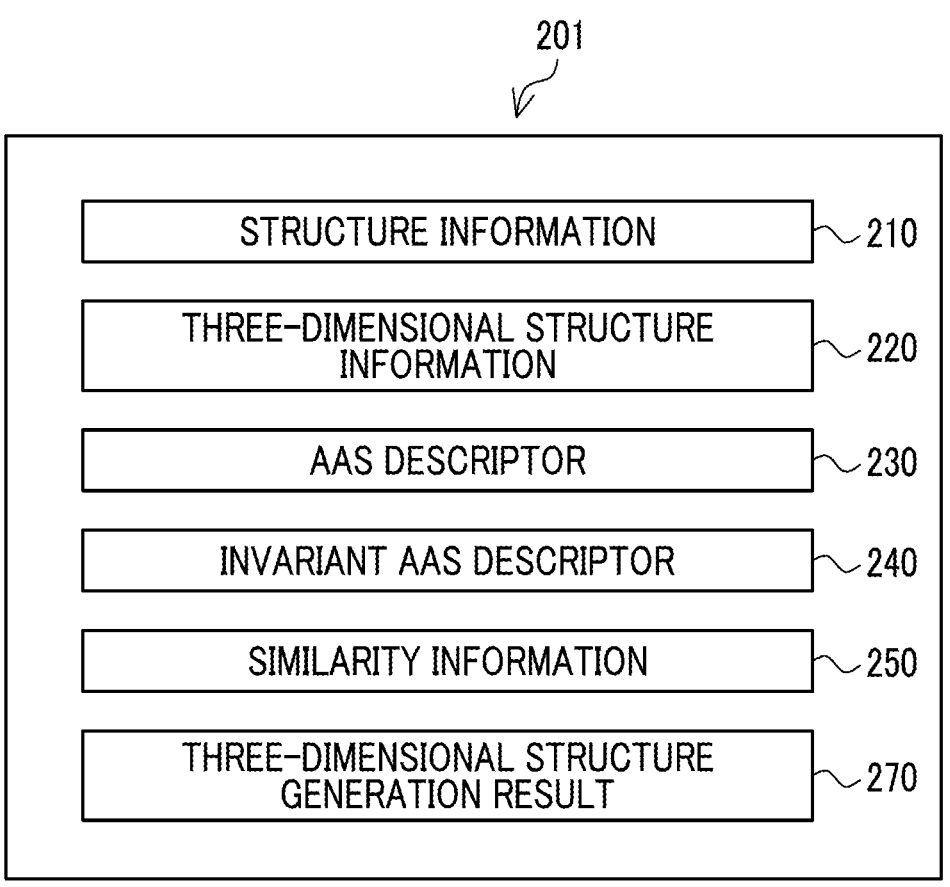
FIG. 20 is a diagram showing information stored in a storage unit.

FIG. 20 is a diagram showing information stored in the storage unit 201. The storage unit 201 stores a three-dimensional structure generation result 270 instead of the compound extraction result 260 in the screening device 10.

The information stored in the storage unit 201 is stored in association as described above with reference to FIG. 4.

<Generation of Three-Dimensional Structure of Target Compound>

Generation of a three-dimensional structure of a target compound (pharmaceutical candidate compound) using the AAS descriptor and the invariant AAS descriptor described above will be described. Since search is not performed in the generation of a three-dimensional structure of a target compound using the compound creating device 20, the three-dimensional structure of the compound can be generated even in a case of "no solution was found as the result of screening search", and thus the three-dimensional structure of the pharmaceutical candidate compound can be efficiently created. The three-dimensional structure is generated, for example, in a mode (first mode) based on a descriptor (the AAS descriptor and the invariant AAS descriptor) of a ligand, in a mode (second mode) based on a descriptor (the AAS descriptor and the invariant AAS descriptor) of a pocket structure of a target protein, or in a mode (third mode) based on a descriptor (the AAS descriptor and the invariant AAS descriptor) of a binding compound. The mode for generation of a three-dimensional structure can be selected from the above-described modes according to the operation of the user via the operation unit 400.

<Generation of Three-Dimensional Structure in Case of Ligand Input>

Figure 21:
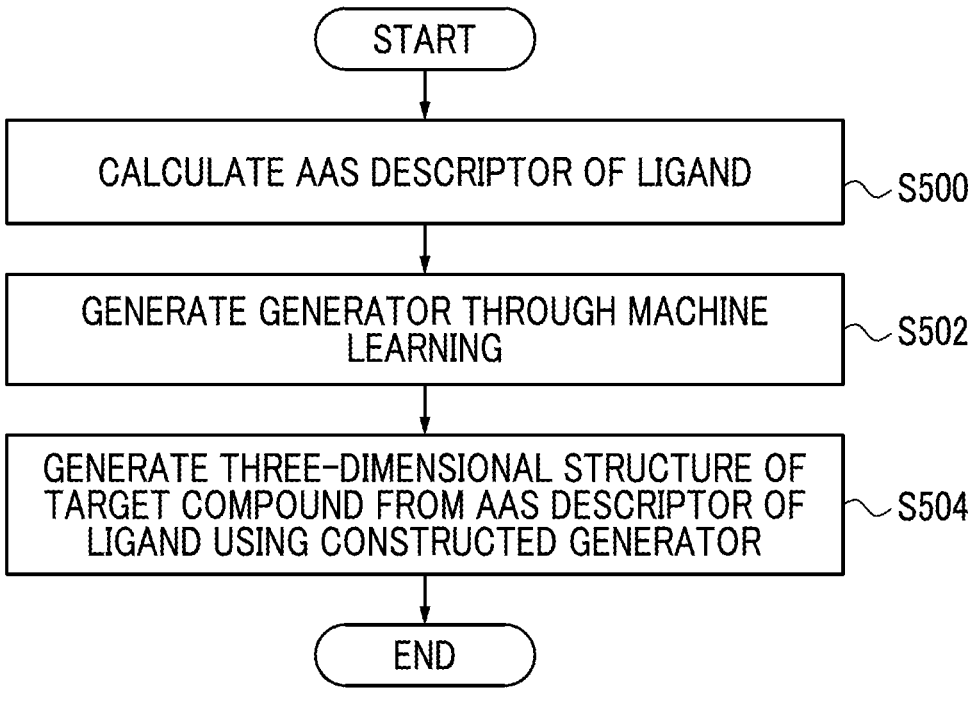
FIG. 21 is a flowchart showing a procedure for generating a three-dimensional structure in a case of ligand input.

FIG. 21 is a flowchart showing a procedure for generating a three-dimensional structure in a case of ligand input. After the start of the process, the feature quantity calculation unit 120 calculates a descriptor (an AAS descriptor) of a ligand (Step S500: the target structure designating step, the three-dimensional structure generating step, and the creating feature quantity calculating step). The process of Step S500 can be performed using the feature quantity calculating method (and the program causing a computer to execute the feature quantity calculating method) according to the embodiment of the present invention in the same manner as in the first embodiment (see FIGS. 6 to 9 and the description related to these drawings).

In Step S502, the generator construction unit 132 constructs a generator through machine learning (a generator constructing step). Hereinafter, the process of Step S502 will be described with reference to FIGS. 22A and 22B.

Figures 22A, 22B:
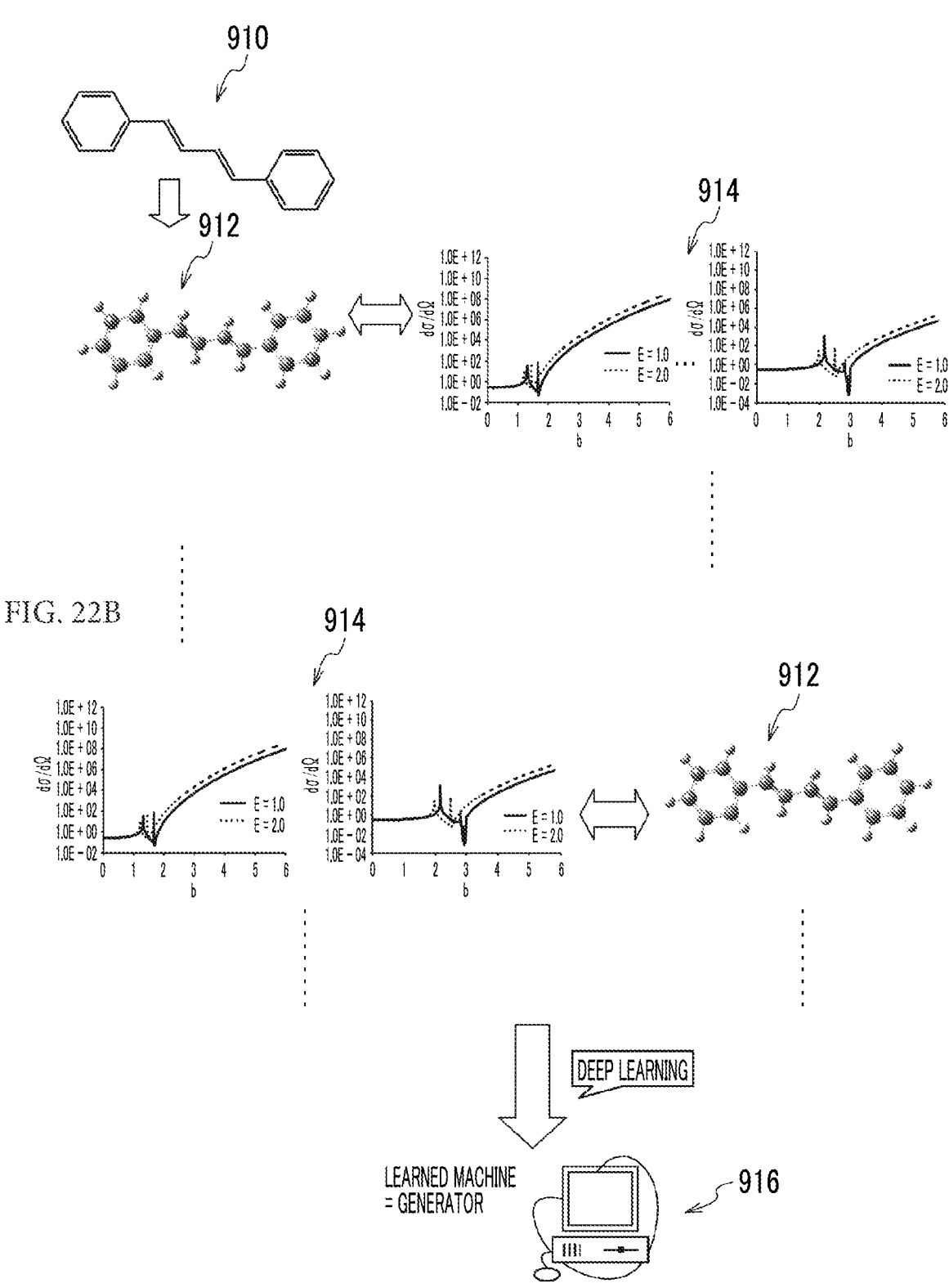
FIGS. 22A and 22B are conceptual diagrams showing a state of constructing a generator using machine learning.

(Step 1) As shown in FIG. 22A, the feature quantity calculation unit 120 calculates the AAS descriptor (first feature quantity) using an amino acid as a probe for a plurality of compounds and creates a pair of a structural formula 912 obtained by three-dimensionalizing the structural formula of a compound 910 and an AAS descriptor 914.

(Step 2) As shown in FIG. 22B, the generator construction unit 132 constructs a generator 916 through machine learning such as deep learning using the three-dimensional structure (structural formula 912) of the compound as teacher data and the AAS descriptor 914 as an explanatory variable. The method of machine learning is not limited to a specific method, and examples thereof include a simple fully binding neural net, a convolutional neural network (CNN), and a generative adversarial network (GAN). However, since the generation accuracy of the three-dimensional structure depends on the learning method to be used, it is preferable to select a learning method according to the condition for generating the three-dimensional structure and the condition such as the required accuracy.

After the completion of the processes of Steps 1 and 2 described above, the process returns to the flowchart of FIG.

21. The compound three-dimensional structure generation unit 142 generates a three-dimensional structure (three-dimensionalized structural formula) of the target compound (hit) from the AAS descriptor of the ligand using the constructed generator (Step S504: the compound three-dimensional structure generating step). In this manner, the three-dimensional structure of a compound having drug efficacy (binding to a target protein) similar to that of a ligand, that is, a pharmaceutical candidate compound can be obtained. Further, a plurality of three-dimensional structures that provide the same AAS descriptor may be present. The compound three-dimensional structure generation unit 142 stores the generated three-dimensional structure in the storage unit 201 in association with the AAS descriptor (the AAS descriptor 230) as the three-dimensional structure generation result 270. The display control unit 150 may display the generated three-dimensional structure on the monitor 310 in response to the user's instruction via the operation unit 400.

Further, in the procedure described above, the number of kinds of amino acids for calculating the AAS descriptor used to construct a generator may be one or plural. Here, the accuracy of the generated three-dimensional structure can be improved by calculating the AAS descriptor for a plurality of kinds of amino acids and providing the result for learning (construction of the generator). Further, in a case where a plurality of AAS descriptors having different kinds of amino acids are used, the combination of amino acids among the descriptors is not particularly limited. The processing unit 100 (the feature quantity calculation unit 120, the similarity calculation unit 130, and the compound extraction unit 140) may determine which amino acid is to be used for calculation of the AAS descriptor and for provision for learning according to the user's instruction via the operation unit 400, but the determination may be made by the processing unit 100 regardless of the user's instruction.

Example of Generation of Three-Dimensional Structure

Figure 23A:
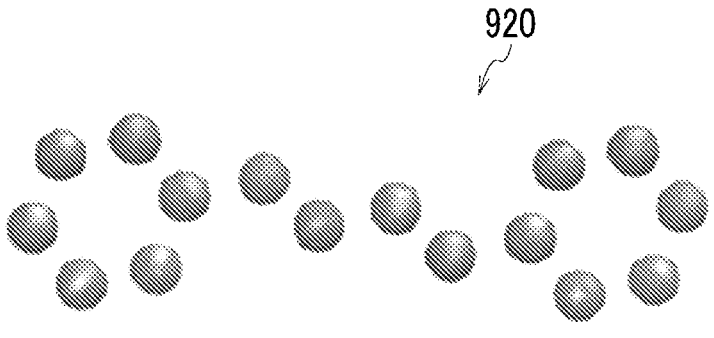
FIGS. 23A and 23B are diagrams showing an example of generating a three-dimensional structure using a generator.
Figure 23B:
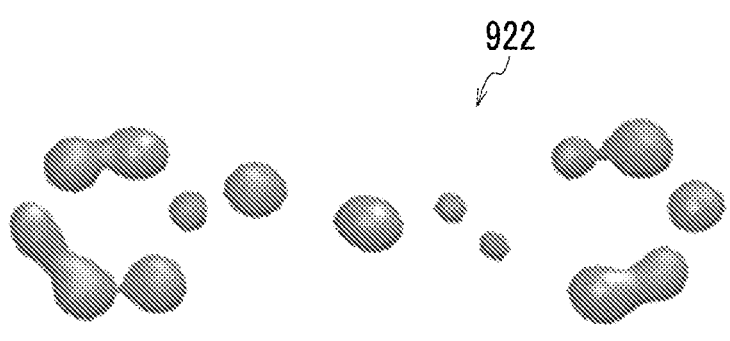

FIGS. 23A and 23B describe an example of a three-dimensional structure generated using a generator constructed through machine learning. FIG. 23A shows correct answer data of the three-dimensional structure, and FIG. 23B shows an example of the three-dimensional structure generated by using the generator. Further, the compound which is a target for creation in FIG. 23 is the compound 910 in FIGS. 7A, 7B, 22A, and 22B.

<Relationship Between Features of Teacher Data and Generated Three-Dimensional Structure>

The three-dimensional structure generated according to the above-described procedure is affected by the features of the compound provided as teacher data. Therefore, a compound having a three-dimensional structure with different features can be generated by selecting the features of the compound to be provided as teacher data. For example, a compound having drug efficacy similar to that of a ligand and having a three-dimensional structure that is easy to synthesize can be generated by providing, as teacher data, an AAS descriptor of a compound having a three-dimensional structure that is easy to synthesize. It is possible to select which compound to be provided for the AAS descriptor as the teacher data according to the features of the compound intended to be generated.

<Generation of Three-Dimensional Structure Using Invariant AAS Descriptor>

In FIGS. 22A to 23B, the generation of the three-dimensional structure using the AAS descriptor (first feature quantity) has been described. Meanwhile, similarly to the case of using the AAS descriptor, the three-dimensional structure of the target compound can be generated through machine learning (deep learning) using the invariant AAS descriptor as teacher data and the three-dimensional structure (three-dimensionalized structural formula) as an explanatory variable even in a case of using the invariant AAS descriptor (first invariant feature quantity).

<Generation of Three-Dimensional Structure in Case of Target Protein Input>

The compound creating device 20 is capable of generating a three-dimensional structure of a target compound by setting a target protein as an input, in addition to the generation of the three-dimensional structure by ligand input. Even in this case, similarly to the case of ligand input, generation of a three-dimensional structure can be performed using an AAS descriptor (second feature quantity) and generation of a three-dimensional structure can be performed using an invariant AAS descriptor (second invariant feature quantity).

Figure 24:
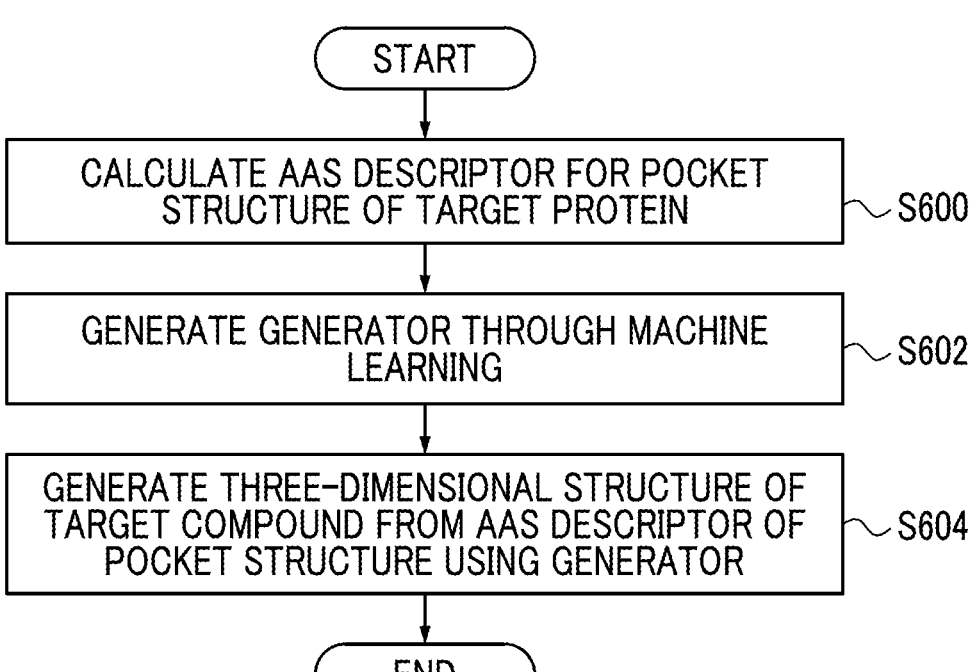
FIG. 24 is a flowchart showing a procedure for generating a three-dimensional structure in a case of target protein input.

FIG. 24 is a flowchart showing a procedure for generating a three-dimensional structure in a case of setting a target protein as an input (an AAS descriptor is set to be used). After the start of the process, the feature quantity calculation unit 120 calculates the AAS descriptor (second feature quantity) for the pocket structure of the target protein (Step S600: the target structure designating step, the three-dimensional structure generating step, and the creating feature quantity calculating step). The process of Step S600 can be performed using the feature quantity calculating method according to the embodiment of the present invention, similarly to the first embodiment (see FIGS. 9A and 9B and the description related to these drawings).

In Step S602, the generator construction unit 132 constructs a generator through machine learning (deep learning) similar to the case of ligand input (the generator constructing step). The construction of the generator can be performed in the same manner as in Steps 1 and 2 described above. Specifically, the feature quantity calculation unit 120 calculates the AAS descriptor (second feature quantity) using an amino acid as a probe for a pocket structure and creates a pair of the three-dimensional structure of the pocket structure and the AAS descriptor. The generator construction unit 132 constructs a generator using the AAS descriptor as an explanatory variable and the three-dimensional structure of the pocket structure as teacher data. The compound three-dimensional structure generation unit 142 generates a three-dimensional structure (three-dimensionalized structural formula) of the target compound (hit) from the AAS descriptor of the pocket structure using the constructed generator (Step S604: the compound three-dimensional structure generating step). In this manner, the three-dimensional structure of a compound having drug efficacy (binding to a target protein) similar to that of the pocket structure, that is, a pharmaceutical candidate compound can be obtained. Further, a plurality of three-dimensional structures that provide the same AAS descriptor may be present. The compound three-dimensional structure generation unit 142 stores the generated three-dimensional structure in the storage unit 201 in association with the AAS descriptor (AAS descriptor 230) as the three-dimensional structure generation result 270 (see FIG. 20). The display control unit 150 may display the generated three-dimensional structure on the monitor 310 in response to the user's instruction via the operation unit 400.

Further, the three-dimensional structure can be generated in the same manner as described above even in a case where the second invariant feature quantity (invariant AAS descriptor) is used.

<Generation of Three-Dimensional Structure in Case where Target Biopolymer Other than Protein is Input>

In addition to the above-described aspect, the compound creating device 20 is capable of generating a three-dimensional structure of a target compound by setting a target biopolymer other than the protein as an input. Even in this case, similarly to the above-described aspect, generation of a three-dimensional structure can be performed using an AAS descriptor (third feature quantity) and generation of a three-dimensional structure can be performed using an invariant AAS descriptor (third invariant feature quantity).

<Creation of Compounds Based on Structural Diversity>

In the above-described aspect, a three-dimensional structure of a pharmaceutical candidate compound is generated using the generator constructed by machine learning. However, as described below, a three-dimensional structure of a compound can also be generated based on the structural diversity.

<Additional Configurations of Compound Creating Method>

The compound creating method described below corresponds to the twenty-third to twenty-seventh aspects of the present invention described above, but the following configurations (hereinafter, referred to as "additional configurations") are appropriately added to the twenty-third to twenty-seventh aspects (hereinafter, referred to as "basic configurations").

(First Additional Configuration)

In the basic configuration, in the candidate structure adopting step, a process of adopting the candidate structure is performed in a case where the absolute value of the difference between the physical property value of the candidate structure and the target value of the physical property value is less than or equal to the absolute value of the difference between the physical property value of the chemical structure and the target value of the physical property value, and a process of calculating a first adoption probability using a first function based on the difference between the physical property value of the candidate structure and the target value of the physical property value and adopting the candidate structure with the first adoption probability in a case where the absolute value of the difference between the physical property value of the candidate structure and the target value of the physical property value is greater than the absolute value of the difference between the physical property value of the chemical structure and the target value of the physical property value, as the first adoption process.

(Second Additional Configuration)

In the first additional configuration, the first function is a monotone decreasing function with respect to a difference between the absolute value of the difference between the physical property value of the candidate structure and the target value of the physical property value and the absolute value of the difference between the physical property value of the chemical structure and the target value of the physical property value.

(Third Additional Configuration)

In the basic configuration and any one of the first or second additional configuration, in the candidate structure adopting step, a process of calculating an increase/decrease amount of the structural diversity of the structure group, calculating a second adoption probability with a second function based on the increase/decrease amount, and adopting the candidate structure with the second adoption probability is performed as the second adoption process.

(Fourth Additional Configuration)

In the third additional configuration, the second function is a monotonous increasing function with respect to the increase/decrease amount of the structural diversity.

(Fifth Additional Configuration)

In the basic configuration and any one of the first to fourth additional configurations, in the candidate structure acquiring step, an atom or an atomic group is added or deleted from the chemical structure to generate a target structure, and the target structure is designated as a candidate structure.

(Sixth Additional Configuration)

In the basic configuration and any one of the first to fifth additional configurations 1 to 5, in the control step, in a case where the number of times the chemical structure is changed reaches a designated number of times and/or the physical property value of the candidate structure reaches a target value, it is determined that the termination conditions are satisfied, and the processes of the input step, the candidate structure acquiring step, the physical property value calculating step, and the candidate structure adopting step are finished.

<Configuration of Compound Creating Device>

Figure 25:
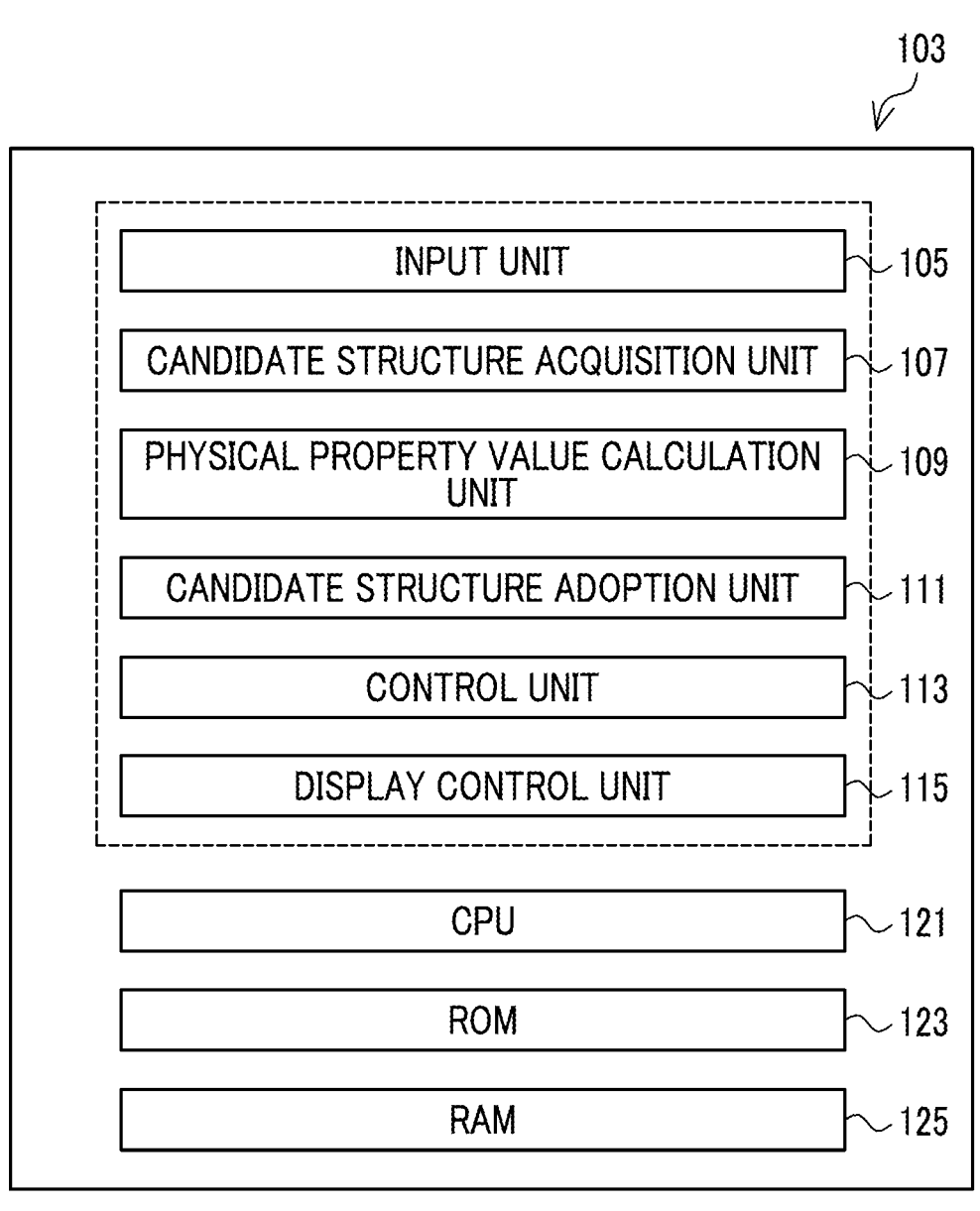
FIG. 25 is a diagram showing a configuration of a compound creating device in a case where a three-dimensional structure of a compound is created based on structural diversity.

FIG. 25 is a diagram showing a configuration of a compound creating device in a case where a three-dimensional structure of a compound is created based on the structural diversity. In this aspect, the compound creating device 20 includes a processing unit 103 (processor) in place of the processing unit 101 shown in FIGS. 18 and 19. The processing unit 103 includes an input unit 105, a candidate structure acquisition unit 107, a physical property value calculation unit 109, a candidate structure adoption unit 111, a control unit 113, a display control unit 115, a CPU 121, a ROM 123, and a RAM 125. Other configurations are the same as those in FIG. 18. In addition, the creation of the compound with a generator and the creation of the compound based on the structural diversity may be executed by using a processing unit having a configuration of the processing unit 103 in addition to the configuration of the processing unit 101.

<Procedure of Compound Creating Method>

Figure 26:
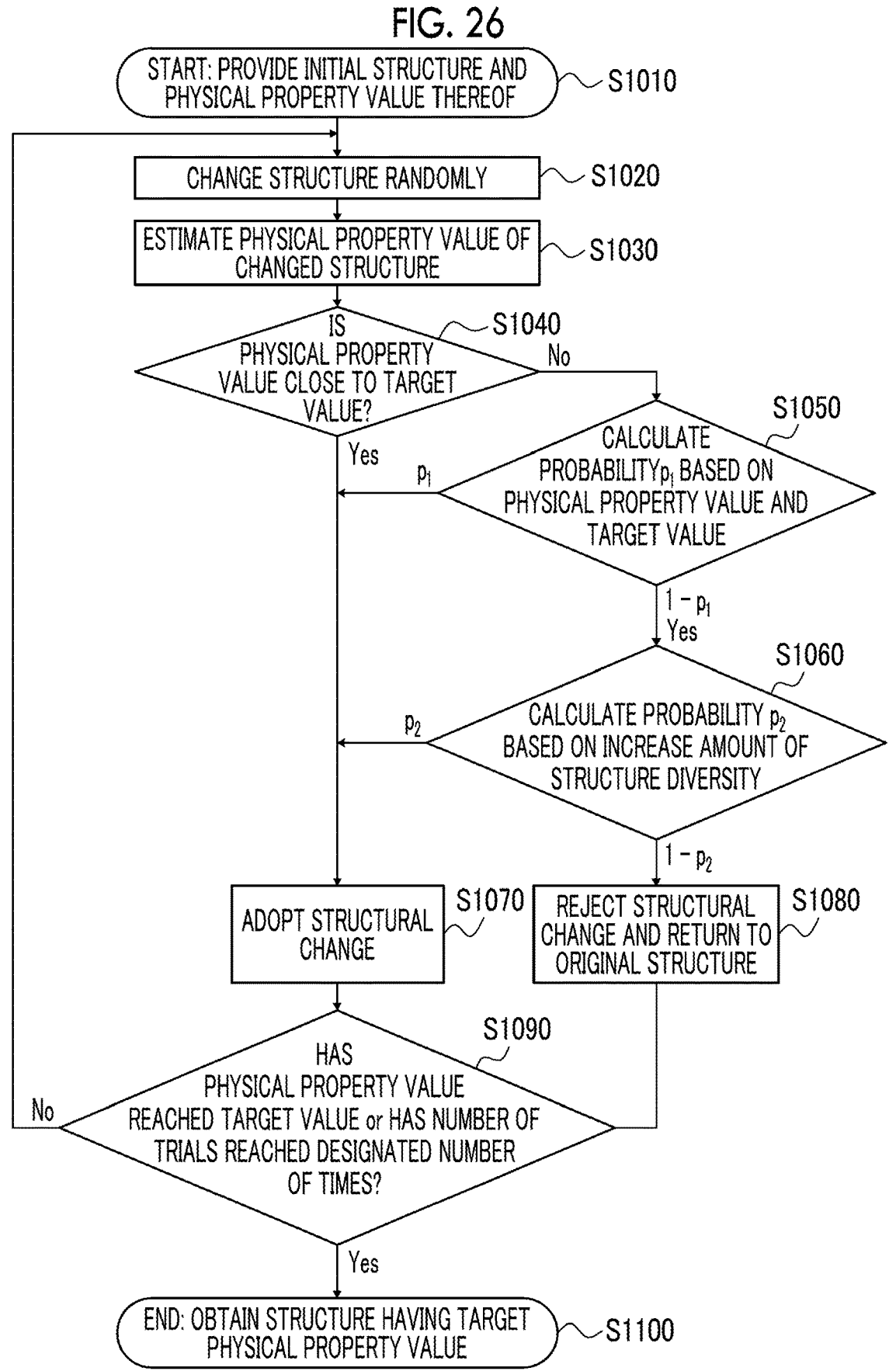
FIG. 26 is a flowchart showing a procedure of a three-dimensional structure generation process based on structural diversity.

FIG. 26 is a flowchart showing a procedure of the compound creating method based on the structural diversity.

<Data Input>

The input unit 105 inputs a chemical structure (initial structure) of one or a plurality of compounds, one or a plurality of physical property values in the chemical structure (initial structure), and the target values of the physical property values (Step S1010: input step). As the data, the data stored in the storage unit 201 may be used or the data may be acquired from the external server 500 and the external database 510 via the network NW. The type of data to be input may be determined according to the user's instruction input via the operation unit 400. The number of initial structures may be one or plural. Further, the number of physical property values may be one or plural.

<Physical Property Value and Target Value>

In the creation of compounds based on the structural diversity, the values of the AAS descriptor (first to third feature quantities) and the invariant AAS descriptor (first to third invariant feature quantities) can be referred to as "physical property values", and these physical property values can be calculated by the feature quantity calculating method of the present invention. In addition, the values of the AAS descriptor or the invariant AAS descriptor for the ligand, the pocket structure, the binding compound, and the like can be defined as "target values" of the physical property values. Specific examples will be described below.

<Acquisition of Candidate Structure>

The candidate structure acquisition unit 107 randomly changes the chemical structure to obtain a candidate structure (Step S1020: candidate structure acquiring step). Here, any method that enables the chemical structure to be changed may be used. For example, a method of adding or deleting an atom or an atomic group to a chemical structure to generate a target structure and using the target structure as a candidate structure can be used. Specifically, this method is a method of generating a compound structure including (A) a step of preparing a compound database as a reference for evaluating synthetic suitability and a compound structure (chemical structure), (B) a step of selecting any of addition of an atom or an atomic group to the compound structure or deletion of an atom from the compound structure, (C) a step of binding a new atom to an atom selected from the atoms of the compound structure in a case of selecting addition of an atom to the compound structure or deleting an atom selected from the atoms of the compound structure to obtain a modified compound structure in a case of selecting deletion of an atom from the compound structure, (D) a step of determining the synthetic suitability of the modified compound structure based on information in the compound database, (E) a step of probabilistically allowing the modification in a case where the modified compound structure has the synthetic suitability or probabilistically rejecting the modification in a case where the modified compound structure does not have the synthetic suitability, and (F) a step of repeating the steps (B) to (E) until the compound structure after completion of the step (E) satisfies the termination conditions. Further, the generated candidate structure may be displayed on the monitor 310 (display device) by the display control unit 115. Further, in a case where the process is returned to Step S1020 from Step S1090 as described below, one or a plurality of structures having physical property values close to the target values among the structures generated at the previous time can be added to the compound database for evaluating the synthetic suitability so that structures having physical property values close to the target values are gradually easily generated in Step S1020.

<Evaluation of Physical Property Value>

The physical property value calculation unit 109 calculates the physical property value of the candidate structure (the structure changed in Step S1020) (Step S1030: the physical property value calculating step and the creating feature quantity calculating step). It is preferable that the same method as in a case of estimating the physical property value of the initial structure is used for the calculation of the physical property value.

<First Adoption Process>

The candidate structure adoption unit 111 determines whether or not the physical property value is close to the target value (Step S1040: candidate structure adopting step). Specifically, in a case where the physical property value before the structural change is defined as f0, the physical property value after the structural change is defined as f1, the target value of the physical property value is defined as F, and |F−f1|≤|F−f0| is satisfied (a case where the absolute value of the difference (first difference) between the physical property value of the candidate structure and the target value of the physical property value is less than or equal to the absolute value of the difference (second difference) between the physical property value of the chemical structure and the target value of the physical property value), since the physical property value is close to (not far away from) the target value, the process proceeds to Step S1070 and the structural change is adopted (first adoption process). Meanwhile, in a case where |F−f1|>|F−f0| is satisfied (a case where the absolute value of the difference (first difference) between the physical property value of the candidate structure and the target value of the physical property value is greater than the absolute value of the difference (second difference) between the physical property value of the chemical structure and the target value of the physical property value), the process proceeds to Step S1050.

In Step S1050 (candidate structure adopting step), the candidate structure adoption unit 111 calculates a first adoption probability with the first function based on the difference between the physical property value of the candidate structure and the target value of the physical property value (first adoption process). Specifically, the candidate structure adoption unit 111 provides a monotone decreasing function P1(d) of d=|F−f1|−|F−f0| and estimates a probability p1=P1 (d). The monotone decreasing function P1(d) corresponds to "first function" in the present invention (the monotone decreasing function with respect to a difference between the absolute value of the difference between the physical property value of the candidate structure and the target value of the physical property value and the absolute value of the difference between the physical property value of the chemical structure and the target value of the physical property value), and the probability p1 corresponds to "first adoption probability" in the present invention.

Various functions can be used as the monotone decreasing function P1(d), and for example, a function represented by Equation (2) can be used. $\sigma$ is a hyperparameter, and the monotone decreasing degree can be adjusted by changing the value of $\sigma$. The value of the parameter may be changed by inputting the user's instruction via the operation unit 400.

$$P_1(d) = \exp[-d/\sigma] \tag{2}$$

In a case of n objectives (the number of physical property values input in Step S1010 is n), for example, the functions represented by Equations (3) and (4) can be used by setting an index representing each objective as i.

$$w_i = \exp[-d_i/\sigma_i] \tag{3}$$

$$P_1(\{d_i\}) = \begin{cases} 1 & (\exists\ \text{is.}t.w_i > 1) \\ \displaystyle\prod_{i=1}^{n} & (\text{otherwise}) \end{cases} \tag{4}$$

The functions represented by Equations (3) and (4) are based on the standard that "in a case where even one physical property value approaching the target is present, the structural change is adopted", but various other functions may be used. In addition, more simply, a method of estimating d=|FF−ff1|−|FF−ff0| from the Euclidean distance |FF−ff| and solving the problem as a single objective (assuming that ff, ff0, ff1, and FF are vectors) by considering the physical property value of n objectives as n-dimensional vectors ff and FF. In a case of adopting this method, it is desirable that the average and the dispersion of each physical property value are calculated from the existing data, standardization is carried out, and the distance is calculated.

In a case where the probability p1 is acquired, the candidate structure adoption unit 111 proceeds to Step S1070 with the probability p1 to adopt the structural change using an appropriately generated random number and proceeds to Step S1055 with a probability (1−p1). That is, the candidate structure adoption unit 111 adopts the candidate structure with a first adoption probability (first adoption process). The reason why the probabilistic process is performed as described above (the structural change is adopted with the probability p1 even in a case where the physical property value is far from the target value) is to prevent a drop into the local minimum state. The local minimum state is "state in which the physical property value is far from the target value regardless of how the structure is changed", and the physical property value is required to undergo a structural change in which the physical property value is far from the target value in order to escape from the local minimum state and reach the global minimum state. Such a path can be ensured by the above-described probabilistic process.

<Second Adoption Process>

In a case where the candidate structure is not adopted as a result of the first adoption process in Step S1050 (probability (1−p1)), the candidate structure adoption unit 111 performs the second adoption process of determining whether or not to adopt the candidate structure based on "whether or not the structural diversity of the structure group formed of the chemical structure and the candidate structure is increased" (Steps S1055, S1060, and S1070). The second adoption process will be described below. Further, the index representing the structure is defined as j, and the structure group is defined as S={sj}. A function that provides the structural diversity of the structure group S is expressed as V(S). It is assumed that the value of V(S) increases as the structural diversity increases.

<Case where Plurality of Initial Structures are Provided>

In a case where N (>1) initial structures are provided, it is assumed that the structural change of the k-th chemical structure among N chemical structures is considered to be adopted or rejected. In the m-th trial, from a structure group Sm−1={s(m−1)j} before the structural change (m−1st) and a structure group Sm={smj} after the change (m-th), a structure group Sk={s(m−1)0, s(m−1)1, . . . , smk, . . . , s(m−1)N} after the structural change of the k-th chemical structure is defined and dv=V(Sk−V(Sm−1) is estimated. That is, dv represents an increase/decrease amount of the structural diversity due to the structural change. In a case of dv≥0 (case where the diversity is improved due to the k-th structural change; Yes in Step S1055), a monotone increasing function P2(dv) with respect to dv (increase/decrease amount of the structural diversity) is provided, and a probability p2=P2(dv) is calculated (Step S1060: second adoption process). Thereafter, the process proceeds to Step S1070 (adopting the structural change; second adoption process) with the probability p2 using an appropriately generated random number and proceeds to Step S1080 (rejecting the structural change and returning to the original structure; rejection process) with the probability (1−p2). The monotone increasing function P2(dv) corresponds to "second function" in the present invention, and the probability p2 corresponds to "second adoption probability" in the present invention.

The reason why the above-described probabilistic process (calculating the candidate structure with the probability p2 calculated by the monotone increasing function P2(dv)) is performed in a case where the structural diversity increases is because the structural change is adopted extremely frequently even though the physical property value is far from the target value in a case of "structural change is adopted without exception in a case where the structural diversity increases" and as a result, the convergence of the physical property value to the target value may be delayed. The convergence of the physical property values is accelerated and the structure of the compound can be efficiently searched for by performing the above-described probabilistic process.

Further, in a case where dv<0 calculated in Step S1060 (case where the diversity decreases; No in Step S1055) is satisfied, the process proceeds to Step S1080 (rejecting the structural change and returning to the original structure; rejection process).

<Case where One Initial Structure is Provided>

In a case where the number of initial structures is one, an index representing the trial is defined as t, dv=V(Scurr)−V(Sprev) is calculated, and the probability p2 may be calculated by the monotone increasing function P2(dv) in the same manner as in the case where a plurality of initial structures are present (Step S1060: second adoption process) in consideration of a structure group Sprev={st−1, st−2, st-m} obtained in the past m trials and a structure group Scurr=st, st−1, . . . , {st-(m−1)} to which the structure st that is considered to be adopted or rejected is added.

<Function that Provides Structural Diversity of Structure Group>

As "function that provides the structural diversity of the structure group" described above, for example, the following definition can be considered based on the Tanimoto coefficient (one of the indices indicating the similarity of compounds) (various other definitions are possible). Specifically, the structure s is represented by a fingerprint of a bit string (a number string of 0 or 1) (which is converted into a fixed-length vector according to a certain rule of a compound, and various generation methods are known) and is defined as Fs, the definition of the Tanimoto coefficient is represented by Equation (5).

$$T_{s,s'} = T(F_s, F_{s'}) = \frac{|F_s \cap F_{s'}|}{|F_s| + |F_{s'}| - |F_s \cap F_{s'}|} \tag{5}$$

Here, |Fs| represents the number of bits of 1 in Fs, and |Fs∩Fs'| represents the number of bits of 1 in common to Fs and Fs'. Ts,s' represents 1 in a case where Fs and Fs' completely match each other and represents 0 in a case where Fs and Fs' do not match at all. Therefore, Ts,s' is an index indicating the similarity between the structure s and the structure s'. Since it is the dissimilarity that is desired to be acquired, the dissimilarity vs,s' of the structure s and the structure s' is defined by Equation (6).

$$v_{s,s'} = 1 - T_{s,s'} \tag{6}$$

The dissimilarity of the structure group S (that is, the structural diversity of the structure group) can be defined by Equation (7) using the dissimilarity vs,s'.

$$V(S) = \frac{2}{N(N-1)} \sum_{s \in S, s' \in S, s \neq s'} v_{s,s'}^2. \tag{7}$$

V(S) represents a value from 0 to 1, and the structural diversity of the structure group increases as the value increases.

In addition, as the monotone increasing function P2(dv) with respect to the increase/decrease amount dv of the structural diversity, for example, a function represented by Equation (8) can be used. σy and Cv are hyperparameters, and the degree of monotonic increase can be adjusted by changing the values. The values of the parameters may be changed by inputting the user's instruction via the operation unit 400.

$$P_2(d_v) = C_v(1 - \exp[-d_v/\sigma_v]) \qquad (8)$$

P2 is Cv at the limit of dv→∞ clearly than the functional form. Therefore, Cv means "probability that the structural change is adopted in a case of the structural change in which the diversity is sufficiently improved".

<Repeating Process>

The first adoption process, the second adoption process, and the rejection process described above are performed for each of the provided initial structures, and one trial ends in a case where the above-described processes for all the chemical structures are completed.

In a case where the candidate structure is adopted or rejected as a result of the first adoption process, the second adoption process, and the rejection process described above, the control unit 113 determines whether or not the termination conditions are satisfied (Step S1090: control step). For example, in a case where the number of times the chemical structure is changed (number of trials) reaches a designated number of times and/or in a case where the physical property value of the candidate structure reaches the target value, the control unit 113 can determine that "the termination conditions are satisfied". In a case where a plurality of chemical structures and/or physical property values have been calculated, "the calculation is terminated in a case where at least one chemical structure and/or physical property value that has reached the target value is present" or "the trial is repeated until all structures and/or physical property values reach the target" may be selected. The control unit 113 repeats the processes (the input step, the candidate structure acquiring step, the physical property value calculating step, and the candidate structure adopting step) from Step S1020 to Step S1080 until the termination conditions are satisfied (No in Step S1090), and the process of the compound creating method is finished (Step S1100) in a case where the termination conditions are satisfied (Yes in Step S1090).

<Effect of Creating Three-Dimensional Structure Based on Structural Diversity>

As described above, according to the compound creating method of creating a three-dimensional structure based on the structural diversity, escape from the local minimum state can be promoted and convergence of the physical property values can be accelerated, and thus a structure of a compound having desired physical property values can be efficiently searched for.

<Specific Physical Property Values, Feature Quantities, and the Like>

Specific physical property values and feature quantities in the three-dimensional structure creation (compound creation) based on the structural diversity according to the above-described aspects will be described.

In a case of creating a three-dimensional structure of a target compound that is bound to the target protein (twenty-third aspect), the feature quantity calculated by using the feature quantity calculating method according to the fifth aspect (the first feature quantity and the AAS descriptor) is "physical property value", and the first feature quantity of the ligand is "target value of the physical property value".

In a case of creating a three-dimensional structure of a target compound that is bound to the target protein (twenty-fourth aspect), the feature quantity calculated by using the feature quantity calculating method according to the sixth aspect (the first invariant feature quantity and the invariant AAS descriptor) is "physical property value", and the first invariant feature quantity of the ligand is "target value of the physical property value".

In a case of creating a three-dimensional structure of a target compound that is bound to the target protein (twenty-fifth aspect), the feature quantity calculated by using the feature quantity calculating method according to the eighth aspect (the second feature quantity and the AAS descriptor) is "physical property value", and the second feature quantity of the pocket structure whose binding to the pocket which is an active site of the target protein has been confirmed is "target value of the physical property value".

In a case of creating a three-dimensional structure of a target compound that is bound to the target protein (twenty-sixth aspect), the feature quantity calculated by using the feature quantity calculating method according to the ninth aspect (the second invariant feature quantity and the invariant AAS descriptor) is "physical property value", and the second invariant feature quantity of the pocket structure whose binding to the pocket which is an active site of the target protein has been confirmed is "target value of the physical property value".

In a case of creating a three-dimensional structure of a target compound that is bound to the target biopolymer other than the protein (twenty-seventh aspect), the feature quantity calculated by using the feature quantity calculating method according to the eleventh aspect (the third feature quantity and the AAS descriptor) is "physical property value", and the third feature quantity of the binding compound whose binding to the target biopolymer other than the protein has been confirmed is "target value of the physical property value".

<Effects of Compound Creating Device>

As described above, the compound creating device 20 according to the second embodiment efficiently creates a three-dimensional structure of a pharmaceutical candidate compound using the feature quantity (the AAS descriptor and the invariant AAS descriptor) calculated by the feature quantity calculating method according to the embodiment of the present invention and the compound creating method (and the compound creating program causing the computer to execute the method) according to the embodiment of the present invention.

Third Embodiment

Figure 27:
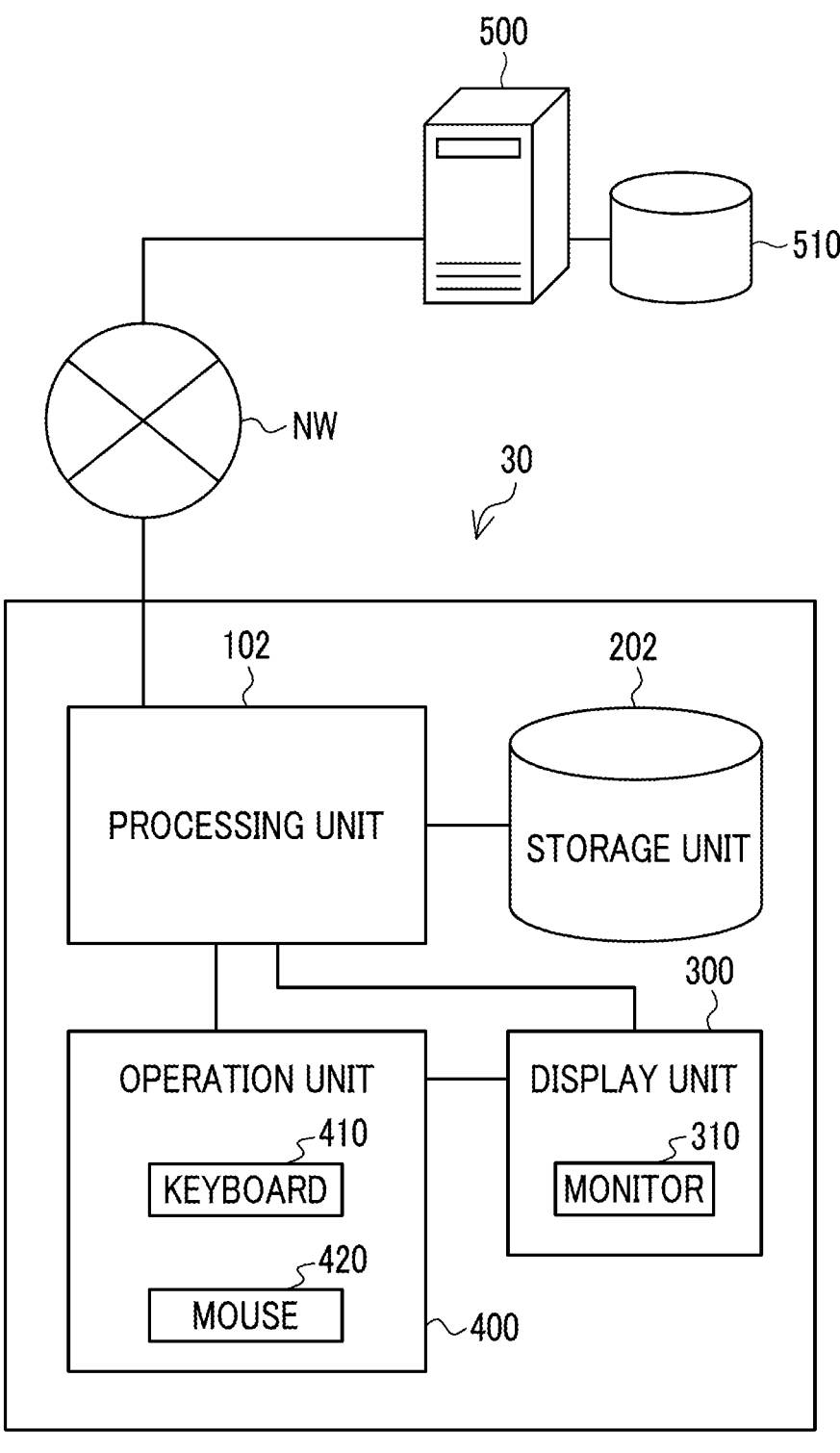
FIG. 27 is a block diagram showing a configuration of a pharmaceutical candidate compound search device according to a third embodiment.
Figure 28:
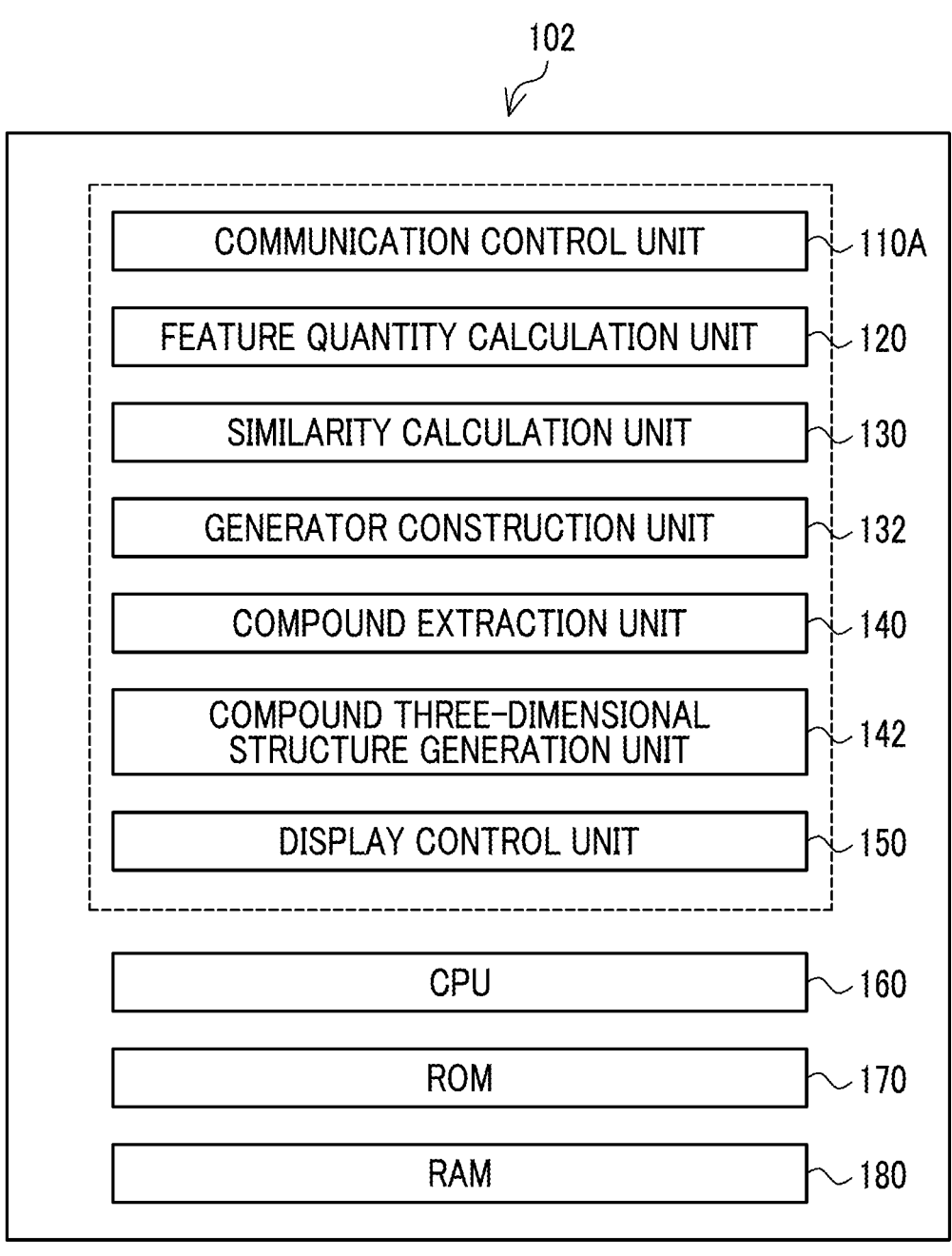
FIG. 28 is a diagram showing a configuration of a processing unit.
Figure 29:
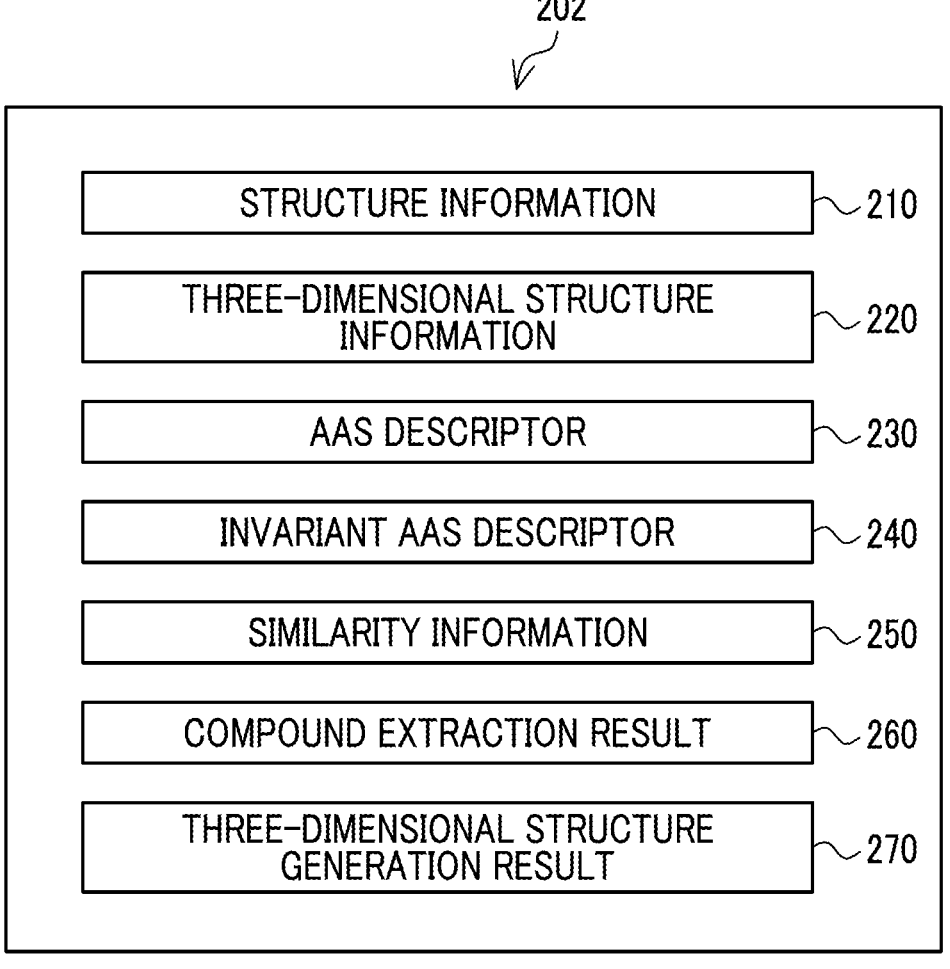
FIG. 29 is a diagram showing information stored in a storage unit.

The first embodiment described above is an aspect in which the calculation of the feature quantity and screening based on the calculation are performed, and the second embodiment is an aspect in which the calculation of the feature quantity and creation of the three-dimensional structure of the target compound based on the calculation are performed. In addition to the calculation of the feature quantity, both the screening and the creation of a three-dimensional structure of the target compound may be performed. Therefore, a pharmaceutical candidate compound search device 30 (the feature quantity calculating device, the screening device, and the compound creating device; see FIG. 27) according to the third embodiment includes a processing unit 102 shown in FIG. 27 in place of the processing unit 100 of the screening device 10 shown in FIG. 1, the processing unit 101 of the compound creating device 20 shown in FIG. 18, or the processing unit 103 shown in FIG. 25. As shown in FIG. 28, the processing unit 102 includes a communication control unit 110A (communication control unit), a feature quantity calculation unit 120 (feature quantity calculation unit), a similarity calculation unit 130 (similarity calculation unit), a generator construction unit 132 (generator construction unit), a compound extraction unit 140 (compound extraction unit), a compound three-dimensional structure generation unit 142 (compound three-dimensional structure generation unit), a display control unit 150 (display control unit), a CPU 160, a ROM 170, and a RAM 180 and can perform calculation of a feature quantity, screening, and creation of a three-dimensional structure of a compound. In addition, the pharmaceutical candidate compound search device 30 stores information necessary for the processes, the results of the processes, and the like in the storage unit 202. Specifically, as shown in FIG. 29, the information (see FIGS. 3 and 20) stored in the storage unit 200 and the information stored in the storage unit 201 are collectively stored in the storage unit 202.

Since other elements are the same as those of the screening device 10 shown in FIG. 1 and the compound creating device 20 shown in FIG. 18, the elements are denoted by the same reference numerals and the detailed description thereof will not be provided. Further, in a case where a compound is created based on the structural diversity, the processing unit 102 has each unit corresponding to the processing unit 103 (see FIG. 25), and information (physical property values, target values, created three-dimensional structures, and the like) corresponding to the creation of the compound 202 based on the structural diversity is stored in the storage unit 202.

With the above-described configuration, also in the pharmaceutical candidate compound search device 30 according to the third embodiment, the feature quantity accurately showing the chemical properties of the target structure is calculated, screening of a pharmaceutical candidate compound is efficiently performed, and a three-dimensional structure of the pharmaceutical candidate compound can be efficiently created, similarly to the screening device 10 and the compound creating device 20.

Hereinbefore, the embodiments of the present invention have been described above, but the present invention is not limited to the above-described aspects, and various modifications can be made as described below.

<Target of Drug that can be Treated>

In the present invention, deoxyribonucleic acid (DNA), ribonucleic acid (RNA), cell membranes, and polysaccharides can be treated in addition to proteins as the targets of drugs. Here, it is necessary to change the probe (amino acid) in a case of the protein to another kind of probe. Specifically, an amino acid is changed to a nucleic acid base in a case of DNA, an amino acid is changed to a nucleic acid base in a case of RNA, an amino acid is changed to a lipid molecule in a case of cell membranes, and an amino acid is changed to a monosaccharide molecule in a case of polysaccharides. In the description below, the reason why DNA, RNA, cell membranes, and polysaccharides can be treated with this change in the present invention will be described.

Proteins, DNA, RNA, cell membranes, and polysaccharides are collectively referred to as biopolymers and are made up of unique building blocks. Specifically, the building block of proteins is an amino acid, the building block of DNA is a nucleic acid base, the building block of RNA is similarly a nucleic acid base, the building block of cell membranes is a lipid molecule, and the building block of polysaccharides is a monosaccharide molecule. Since DNA, RNA, cell membranes, and polysaccharides have pockets that are active sites similarly to the proteins, even in a case where a drug target is DNA, RNA, cell membranes, and polysaccharides, the present invention can deal with this by changing amino acids to the building blocks of the targets in the embodiments shown in the case of proteins. Further, water can be considered at the time of quantifying the degree of accumulation of amino acids, nucleic acid bases, lipid molecules, and monosaccharide molecules in the periphery of a compound or a pocket structure.

<Activities that can be Treated>

In the present invention, in addition to the typical activity which is "activity of a target biomolecule alone by a compound", "activity of a cell, which is a composite formed of other biomolecules in addition to the target biomolecule by a compound" can also be treated.

EXPLANATION OF REFERENCES

10: screening device
20: compound creating device
30: pharmaceutical candidate compound search device
100: processing unit
101: processing unit
102: processing unit
103: processing unit
105: input unit
107: candidate structure acquisition unit
109: physical property value calculation unit
110: information input unit
110A: communication control unit
111: candidate structure adoption unit
113: control unit
115: display control unit
120: feature quantity calculation unit
121: CPU
123: ROM
125: RAM
130: similarity calculation unit
132: generator construction unit
140: compound extraction unit
142: compound three-dimensional structure generation unit
150: display control unit
160: CPU
170: ROM
180: RAM
200: storage unit
201: storage unit
202: storage unit
210: structure information
220: three-dimensional structure information
230: AAS descriptor
240: invariant AAS descriptor
250: similarity information
260: compound extraction result
270: three-dimensional structure generation result
300: display unit
310: monitor
400: operation unit
410: keyboard
420: mouse
500: external server
510: external database
900: compound
902: probe
910: compound
912: structural formula
914: AAS descriptor
916: generator
NW: network
PO: pocket PS: pocket structure S100~S112: each step of feature quantity calculating method S200~S206: step of feature quantity calculating method S300~S304: each step of compound extracting method S400~S404: each step of compound extracting method S500~S504: each step of compound creating method S600~S604: each step of compound creating method S1010~S1100: each step of compound creating method TP: target protein b: impact parameter $r_{min}$: closest distance $\theta_a$: scattering angle

What is claimed is:

1. A feature quantity calculating method comprising:

a target structure designating step of designating a target structure formed of a plurality of unit structures having chemical properties;

a three-dimensional structure acquiring step of acquiring a three-dimensional structure from the plurality of unit structures for the target structure;

a probe feature quantity calculating step of calculating a feature quantity showing a cross-sectional area of one or more kinds of probes for the target structure, wherein the probe is a structure in which a plurality of points having a real electric charge and generating a van der Waals force are disposed to be separated from each other; and an invariant conversion step of converting the first feature quantity into an invariant with respect to rotation of the compound to calculate a first invariant feature quantity, wherein a compound is designated as the target structure in the target structure designating step, a three-dimensional structure of the compound formed of a plurality of atoms as the plurality of unit structures is acquired in the three-dimensional structure acquiring step, a first feature quantity of the compound acquired in the three-dimensional structure acquiring step is calculated using an amino acid as the probe in the probe feature quantity calculating step, and data capacity is reduced by the conversion into the invariant.

2. The feature quantity calculating method according to claim 1, wherein a cross-sectional area, a closest distance, and a scattering angle are calculated as the feature quantity in the probe feature quantity calculating step.

3. The feature quantity calculating method according to claim 1, wherein the feature quantity depending on a kind, a number, a combination, an impact parameter, and incident energy of the probe is calculated as the feature quantity in the probe feature quantity calculating step.

4. The feature quantity calculating method according to claim 1, wherein the three-dimensional structure is acquired by generating a three-dimensional structure of a designated target structure in the three-dimensional structure acquiring step.

5. The feature quantity calculating method according to claim 1, wherein the first feature quantity of two different kinds of amino acids is calculated in the probe feature quantity calculating step, and the first invariant feature quantity is calculated using the first feature quantity of the two different kinds of amino acids in the invariant conversion step.

6. The feature quantity calculating method according to claim 1, wherein a pocket structure bound to a pocket that is an active site of a target protein is designated as the target structure in the target structure designating step, a three-dimensional structure of the pocket structure is acquired with a plurality of virtual spheres in the three-dimensional structure acquiring step, and a second feature quantity of the pocket structure acquired in the three-dimensional structure acquiring step is calculated using an amino acid as a probe in the probe feature quantity calculating step.

7. The feature quantity calculating method according to claim 1, wherein a compound is designated as the target structure in the target structure designating step, a three-dimensional structure of the compound formed of a plurality of atoms is generated in the three-dimensional structure acquiring step, and a third feature quantity of the three-dimensional structure of the compound acquired in the three-dimensional structure acquiring step is calculated using one or more among one or more kinds of nucleic acid bases, one or more kinds of lipid molecules, one or more kinds of monosaccharide molecules, water, and one or more kinds of ions, as the probes in the probe feature quantity calculating step.

8. A screening method of extracting a first target compound which is bound to a target protein and/or a second target compound which is not bound to the target protein, from a plurality of compounds, the method comprising:

a storing step of storing a three-dimensional structure of a compound formed of a plurality of atoms and the first feature quantity of the three-dimensional structure of the compound which is calculated using the feature quantity calculating method according to claim 1 in association with each other for each of the plurality of compounds;

a screening feature quantity calculating step of calculating the first feature quantity of a ligand that is a compound whose binding to the target protein has been confirmed;

a similarity calculating step of calculating a similarity between the first feature quantity of the plurality of compounds and the first feature quantity of the ligand; and a compound extracting step of extracting the first target compound and the second target compound from the plurality of compounds based on the similarity, wherein at least one of storing information showing the extracted first target compound and/or the extracted second target compound in a non-transitory recording medium and displaying the information on a display device is performed, in response to instruction by a user via an operation unit.

9. A screening method of extracting a first target compound which is bound to a target protein and/or a second target compound which is not bound to the target protein, from a plurality of compounds, the method comprising:

a storing step of storing a three-dimensional structure of a compound formed of a plurality of atoms and the first invariant feature quantity of the three-dimensional structure of the compound calculated using the feature quantity calculating method according to claim 1 in association with each other for each of the plurality of compounds;

a screening feature quantity calculating step of calculating the first invariant feature quantity of a ligand that is a compound whose binding to the target protein has been confirmed;

a similarity calculating step of calculating a similarity between the first invariant feature quantity of the plurality of compounds and the first invariant feature quantity of the ligand; and a compound extracting step of extracting the first target compound and the second target compound from the plurality of compounds based on the similarity, wherein at least one of storing information showing the extracted first target compound and/or the extracted second target compound in a non-transitory recording medium and displaying the information on a display device is performed, in response to instruction by a user via an operation unit.

10. A screening method of extracting a target compound which is bound to a target biopolymer other than a protein from a plurality of compounds, the method comprising:

a storing step of storing a three-dimensional structure of a compound formed of a plurality of atoms and the third feature quantity of the three-dimensional structure of the compound calculated using the feature quantity calculating method according to claim 7 in association with each other for each of the plurality of compounds;

a feature quantity calculating step of calculating the third feature quantity of a binding compound that is a compound whose binding to the target biopolymer other than the protein has been confirmed;

a similarity calculating step of calculating a similarity between the third feature quantity of the plurality of compounds and the third feature quantity of the binding compound; and a compound extracting step of extracting the first target compound and the second target compound from the plurality of compounds based on the similarity, wherein at least one of storing information showing the extracted first target compound and/or the extracted second target compound in a non-transitory recording medium and displaying the information on a display device is performed, in response to instruction by a user via an operation unit.

11. A compound creating method of creating a three-dimensional structure of a target compound that is bound to a target protein from a plurality of compounds, the method comprising:

a storing step of storing a three-dimensional structure of a compound formed of a plurality of atoms and the first feature quantity calculated using the feature quantity calculating method according to claim 1 in association with each other for each of the plurality of compounds;

a creating feature quantity calculating step of calculating the first feature quantity of a ligand that is a compound whose binding to the target protein has been confirmed;

a generator constructing step of constructing a generator through machine learning using the three-dimensional structures of the plurality of compounds as teacher data and the first feature quantity as an explanatory variable; and a compound three-dimensional structure generating step of generating the three-dimensional structure of the target compound from the first feature quantity of the ligand using the generator, wherein at least one of storing information showing the created target compound in a non-transitory recording medium and displaying the information on a display device is performed, in response to instruction by a user via an operation unit.

12. A compound creating method of creating a three-dimensional structure of a target compound that is bound to a target biopolymer other than a protein from a plurality of compounds, the method comprising:

a storing step of storing a three-dimensional structure of a compound formed of a plurality of atoms and the third feature quantity calculated using the feature quantity calculating method according to claim 7 in association with each other for each of the plurality of compounds;

a creating feature quantity calculating step of calculating the third feature quantity of a binding compound that is a compound whose binding to the target biopolymer other than the protein has been confirmed;

a generator constructing step of constructing a generator through machine learning using the three-dimensional structures of the plurality of compounds as teacher data and the third feature quantity as an explanatory variable; and a compound three-dimensional structure generating step of generating the three-dimensional structure of the target compound from the third feature quantity of the binding compound using the generator, wherein at least one of storing information showing the created target compound in a non-transitory recording medium and displaying the information on a display device is performed, in response to instruction by a user via an operation unit.

13. A compound creating method of creating a three-dimensional structure of a target compound that is bound to a target protein, the method comprising:

an input step of inputting a chemical structure of one or a plurality of compounds, the first feature quantity of the chemical structure calculated using the feature quantity calculating method according to claim 1, and the first feature quantity of a ligand that is a compound whose binding to the target compound has been confirmed as a target value of the first feature quantity;

a candidate structure acquiring step of changing the chemical structure to obtain a candidate structure;

a creating feature quantity calculating step of calculating the first feature quantity of the candidate structure using the feature quantity calculating method according to claim 1;

a candidate structure adopting step of adopting or rejecting the candidate structure by performing a first adoption process of determining whether or not to adopt the candidate structure based on whether or not the first feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied, wherein at least one of storing information showing the created target compound in a non-transitory recording medium and displaying the information on a display device is performed, in response to instruction by a user via an operation unit.

14. A compound creating method of creating a three-dimensional structure of a target compound that is bound to a target protein, the method comprising:

an input step of inputting a chemical structure of one or a plurality of compounds, the second feature quantity of the chemical structure calculated using the feature quantity calculating method according to claim 6, and the second feature quantity of a pocket structure whose binding to a pocket that is an active site of the target protein has been confirmed as a target value of the second feature quantity;

a candidate structure acquiring step of changing the chemical structure to obtain a candidate structure;

a creating feature quantity calculating step of calculating the second feature quantity of the candidate structure using the feature quantity calculating method according to claim 6;

a candidate structure adopting step of adopting or rejecting the candidate structure by performing a first adoption process of determining whether or not to adopt the candidate structure based on whether or not the second feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied, wherein at least one of storing information showing the created target compound in a non-transitory recording medium and displaying the information on a display device is performed, in response to instruction by a user via an operation unit.

15. A compound creating method of creating a three-dimensional structure of a target compound that is bound to a target biopolymer other than a protein, the method comprising:

an input step of inputting a chemical structure of one or a plurality of compounds, the third feature quantity of the chemical structure calculated using the feature quantity calculating method according to claim 7, and the third feature quantity of a binding compound that is a compound whose binding to the target biopolymer other than the protein has been confirmed as a target value of the third feature quantity;

a candidate structure acquiring step of changing the chemical structure to obtain a candidate structure;

a creating feature quantity calculating step of calculating the third feature quantity of the candidate structure using the feature quantity calculating method according to claim 7;

a candidate structure adopting step of adopting or rejecting the candidate structure by performing a first adoption process of determining whether or not to adopt the candidate structure based on whether or not the third feature quantity of the candidate structure approaches the target value due to the change of the chemical structure, performing a second adoption process of determining whether or not to adopt the candidate structure in a case where the candidate structure has not been adopted by the first adoption process, based on whether or not structural diversity of a structure group formed of the chemical structure and the candidate structure is increased due to the change of the chemical structure, and performing a rejection process of rejecting the change of the chemical structure in a case where the candidate structure has not been adopted by the first adoption process and the second adoption process, to return the chemical structure before the change; and a control step of repeating the input step, the candidate structure acquiring step, the creating feature quantity calculating step, and the processes in the candidate structure adopting step until termination conditions are satisfied, wherein at least one of storing information showing the created target compound in a non-transitory recording medium and displaying the information on a display device is performed, in response to instruction by a user via an operation unit.

16. The screening method according to claim 8, wherein the operation unit includes a keyboard and a mouse as an input device and/or a pointing device.

17. The screening method according to claim 8, wherein the display device is a monitor display device.

18. The screening method according to claim 8, the recording medium is one of a magneto-optical disk or a semiconductor memory.

19. The compound creating method according to claim 11, wherein the operation unit includes a keyboard and a mouse as an input device and/or a pointing device.

20. The compound creating method according to claim 11, wherein the display device is a monitor display device.

21. The compound creating method according to claim 11, the recording medium is one of a magneto-optical disk or a semiconductor memory.

22. The feature quantity calculating method according to claim 6, further comprising:

an invariant conversion step of converting the second feature quantity into an invariant with respect to rotation of the pocket structure to calculate a second invariant feature quantity.

23. The feature quantity calculating method according to claim 7, further comprising:

an invariant conversion step of converting the third feature quantity into an invariant with respect to rotation of the compound to calculate a third invariant feature quantity.

24. A feature quantity calculating method comprising:

a target structure designating step of designating a target structure formed of a plurality of unit structures having chemical properties;

a three-dimensional structure acquiring step of acquiring a three-dimensional structure from the plurality of unit structures for the target structure;

a probe feature quantity calculating step of calculating a feature quantity showing a cross-sectional area of one or more kinds of probes for the target structure, wherein the probe is a structure in which a plurality of points having a real electric charge and generating a van der Waals force are disposed to be separated from each other and an invariant conversion step of converting the second feature quantity into an invariant with respect to rotation of the pocket structure to calculate a second invariant feature quantity, wherein a pocket structure bound to a pocket that is an active site of a target protein is designated as the target structure in the target structure designating step, a three-dimensional structure of the pocket structure is acquired with a plurality of virtual spheres in the three-dimensional structure acquiring step, a second feature quantity of the pocket structure acquired in the three-dimensional structure acquiring step is calculated using an amino acid as a probe in the probe feature quantity calculating step, and data capacity is reduced by the conversion into the invariant.

25. The feature quantity calculating method according to claim 24, wherein the second feature quantity of two different kinds of amino acids is calculated in the probe feature quantity calculating step, and the second invariant feature quantity is calculated using the second feature quantity of the two different kinds of amino acids in the invariant conversion step.

26. A feature quantity calculating method comprising:

a target structure designating step of designating a target structure formed of a plurality of unit structures having chemical properties; and a three-dimensional structure acquiring step of acquiring a three-dimensional structure from the plurality of unit structures for the target structure; and a probe feature quantity calculating step of calculating a feature quantity showing a cross-sectional area of one or more kinds of probes for the target structure, wherein the probe is a structure in which a plurality of points having a real electric charge and generating a van der Waals force are disposed to be separated from each other, and an invariant conversion step of converting the third feature quantity into an invariant with respect to rotation of the compound to calculate a third invariant feature quantity, wherein a compound is designated as the target structure in the target structure designating step, a three-dimensional structure of the compound formed of a plurality of atoms is generated in the three-dimensional structure acquiring step, a third feature quantity of the three-dimensional structure of the compound acquired in the three-dimensional structure acquiring step is calculated using one or more among one or more kinds of nucleic acid bases, one or more kinds of lipid molecules, one or more kinds of monosaccharide molecules, water, and one or more kinds of ions, as the probes in the probe feature quantity calculating step, and data capacity is reduced by the conversion into the invariant.

* * * * *